United States Patent
Zalev et al.

(10) Patent No.: US 10,309,936 B2
(45) Date of Patent: Jun. 4, 2019

(54) SYSTEMS AND METHODS FOR COMPONENT SEPARATION IN MEDICAL IMAGING

(71) Applicant: Seno Medical Instruments, Inc., San Antonio, TX (US)

(72) Inventors: Jason Zalev, Thornhill (CA); Bryan Clingman, San Antonio, TX (US); Donald G. Herzog, Collingswood, NJ (US)

(73) Assignee: Seno Medical Instruments, Inc., San Antonio, TX (US)

( * ) Notice: Subject to any disclaimer, the term of this patent is extended or adjusted under 35 U.S.C. 154(b) by 1268 days.

(21) Appl. No.: 14/512,896

(22) Filed: Oct. 13, 2014

(65) Prior Publication Data
US 2015/0101411 A1  Apr. 16, 2015

Related U.S. Application Data

(60) Provisional application No. 61/889,585, filed on Oct. 11, 2013.

(51) Int. Cl.
*G01N 29/24* (2006.01)
*G01N 29/04* (2006.01)
(Continued)

(52) U.S. Cl.
CPC ....... *G01N 29/2418* (2013.01); *A61B 5/0095* (2013.01); *A61B 5/7203* (2013.01);
(Continued)

(58) Field of Classification Search
CPC ........ A61B 2560/0223; A61B 2576/00; A61B 5/0095; A61B 5/7703; A61B 8/4281;
(Continued)

(56) References Cited

U.S. PATENT DOCUMENTS 4,163,205 A * 7/1979 Barron ................... G01V 1/375
181/115
4,267,732 A 5/1981 Quate
(Continued)

FOREIGN PATENT DOCUMENTS

| EP | 0282234 A1 | 9/1988 |
|---|---|---|
| WO | 90/10866 A1 | 9/1990 |

(Continued)

OTHER PUBLICATIONS

Hamilton, James D., et al. "High frequency optoacoustic arrays using etalon detection." IEEE transactions on ultrasonics, ferroelectrics, and frequency control 47.1 (2000): 160-169.
(Continued)

*Primary Examiner* — Baisakhi Roy
(74) *Attorney, Agent, or Firm* — Dean D. Small; The Small Patent Law Group, LLC

(57) ABSTRACT

A system is provided for component separation. In an embodiment, a light source or other source of electromagnetic energy delivers energy to a volume of tissue. A transducer array or other sensor receives a resulting acoustic signal, and a processing subsystem processes the acoustic signal to separate a direct acoustic return component from a secondary acoustic return component of the acoustic signal. An output and/or storage device presents and/or stores information about the direct acoustic return component, the secondary acoustic return component, or both. Other embodiments include a coded probe, a probe having an isolator that produces a wavefront, a sensor for measuring intensity of an acoustic wave produced by absorbed photons, and a system that receives acoustic signals from surface targets to determine an optical parameter of the volume.

49 Claims, 17 Drawing Sheets

(51) Int. Cl.
- *A61B 8/00* (2006.01)
- *G01N 29/06* (2006.01)
- *A61B 5/00* (2006.01)

(52) U.S. Cl.
CPC ....... *A61B 8/4281* (2013.01); *G01N 29/0654* (2013.01); *A61B 5/0035* (2013.01); *A61B 5/0066* (2013.01); *A61B 8/4416* (2013.01); *A61B 2560/0223* (2013.01); *A61B 2576/00* (2013.01); *G01N 2291/023* (2013.01); *G01N 2291/02475* (2013.01); *H01L 2924/0002* (2013.01)

(58) Field of Classification Search
CPC ... A61B 5/0035; A61B 5/0066; A61B 8/4416; H01L 2924/0002
See application file for complete search history.

(56) References Cited

U.S. PATENT DOCUMENTS

| | | |
|---|---|---|
| 5,504,281 A | 4/1996 | Whitney et al. |
| 5,713,356 A | 2/1998 | Kruger |
| 5,723,870 A * | 3/1998 | Crowne ............... B64D 37/00 250/221 |
| 5,840,023 A | 11/1998 | Oraevsky et al. |
| 5,929,893 A * | 7/1999 | Son ..................... G02F 1/11 347/239 |
| 5,977,538 A | 11/1999 | Unger et al. |
| 6,263,094 B1 | 7/2001 | Rosich et al. |
| 6,751,490 B2 | 6/2004 | Esenaliev et al. |
| 7,972,272 B2 | 7/2011 | Munce et al. |
| 8,016,419 B2 | 9/2011 | Zhang et al. |
| 8,025,406 B2 | 9/2011 | Zhang et al. |
| 8,144,327 B2 | 3/2012 | Nakajima et al. |
| 8,214,010 B2 | 7/2012 | Courtney et al. |
| 8,298,144 B2 | 10/2012 | Burcher |
| 8,300,224 B2 | 10/2012 | Nakajima et al. |
| 8,353,830 B2 | 1/2013 | Kanayama et al. |
| 8,353,833 B2 | 1/2013 | Dogra et al. |
| 8,460,195 B2 | 6/2013 | Courtney et al. |
| 8,480,584 B2 | 7/2013 | Kanayama et al. |
| 8,712,506 B2 | 4/2014 | Courtney et al. |
| 8,784,321 B2 | 7/2014 | Courtney et al. |
| 8,870,770 B2 | 10/2014 | Dogra et al. |
| 8,876,717 B2 | 11/2014 | Tokita et al. |
| 9,357,923 B2 | 6/2016 | Courtney et al. |
| 9,375,147 B2 | 6/2016 | Courtney et al. |
| 9,700,214 B2 | 7/2017 | Ichihara et al. |
| 2001/0021807 A1 * | 9/2001 | Saito ..................... B06B 1/067 600/437 |
| 2001/0022657 A1 | 9/2001 | Autrey et al. |
| 2004/0061799 A1 * | 4/2004 | Atarashi ............... G02B 7/022 348/340 |
| 2005/0004458 A1 | 1/2005 | Kanayama et al. |
| 2006/0241572 A1 | 10/2006 | Zhou |
| 2007/0110294 A1 * | 5/2007 | Schaap ................. G06K 9/40 382/131 |
| 2008/0071172 A1 | 3/2008 | Bruck et al. |
| 2008/0177183 A1 | 7/2008 | Courtney et al. |
| 2009/0227992 A1 * | 9/2009 | Nir ........................ A61B 18/26 606/7 |
| 2010/0049044 A1 | 2/2010 | Burcher |
| 2010/0094134 A1 * | 4/2010 | Zhu ...................... A61B 5/0073 600/473 |
| 2010/0249562 A1 | 9/2010 | Zhang et al. |
| 2010/0249570 A1 * | 9/2010 | Carson ................ A61B 5/0059 600/407 |
| 2010/0256489 A1 | 10/2010 | Pedersen et al. |
| 2010/0298688 A1 | 11/2010 | Dogra et al. |
| 2011/0054292 A1 | 3/2011 | Hirson et al. |
| 2011/0125014 A1 | 5/2011 | Derode et al. |
| 2011/0201914 A1 | 8/2011 | Wang et al. |
| 2011/0288411 A1 | 11/2011 | Cerwin et al. |
| 2011/0303015 A1 | 12/2011 | Ichihara et al. |
| 2011/0306857 A1 | 12/2011 | Razansky et al. |
| 2011/0319743 A1 | 12/2011 | Satoh |
| 2012/0165677 A1 | 6/2012 | Li et al. |
| 2013/0116538 A1 | 5/2013 | Herzog et al. |
| 2013/0190591 A1 | 7/2013 | Hirson et al. |
| 2013/0190595 A1 | 7/2013 | Oraevsky et al. |
| 2013/0231549 A1 | 9/2013 | Yamamoto et al. |
| 2013/0335441 A1 | 12/2013 | Zalev et al. |
| 2014/0007690 A1 | 1/2014 | Hirota |
| 2014/0051969 A1 | 2/2014 | Suzuki |
| 2014/0126784 A1 * | 5/2014 | Hsieh ................... G06T 11/005 382/128 |
| 2014/0187902 A1 | 7/2014 | Sato et al. |
| 2014/0198606 A1 | 7/2014 | Morscher et al. |
| 2014/0221810 A1 | 8/2014 | Kacprowicz |
| 2014/0274212 A1 * | 9/2014 | Zurek ................. H04M 1/6041 455/563 |
| 2014/0303476 A1 | 10/2014 | Dogra et al. |
| 2014/0323860 A1 | 10/2014 | Courtney et al. |
| 2015/0112188 A1 * | 4/2015 | Stigall ................. A61B 17/064 600/424 |
| 2015/0182122 A1 * | 7/2015 | Bamber .............. A61B 5/0095 600/438 |
| 2016/0249812 A1 | 9/2016 | Wang et al. |
| 2016/0302763 A1 | 10/2016 | Courtney et al. |
| 2017/0112474 A1 | 4/2017 | Burcher |

FOREIGN PATENT DOCUMENTS

| | | |
|---|---|---|
| WO | 2013067419 A1 | 5/2013 |
| WO | 2013112626 A1 | 8/2013 |

OTHER PUBLICATIONS

Ermilov, Sergey A., et al. "Laser optoacoustic imaging system for detection of breast cancer." Journal of biomedical optics 14.2 (2009): 024007-024007.

* cited by examiner

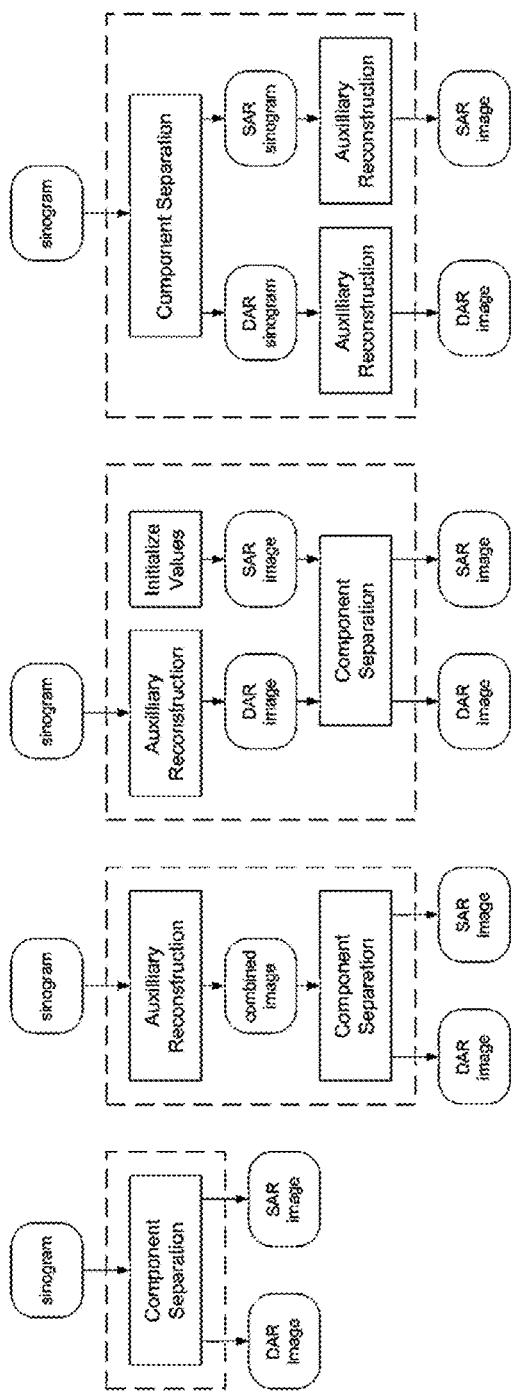

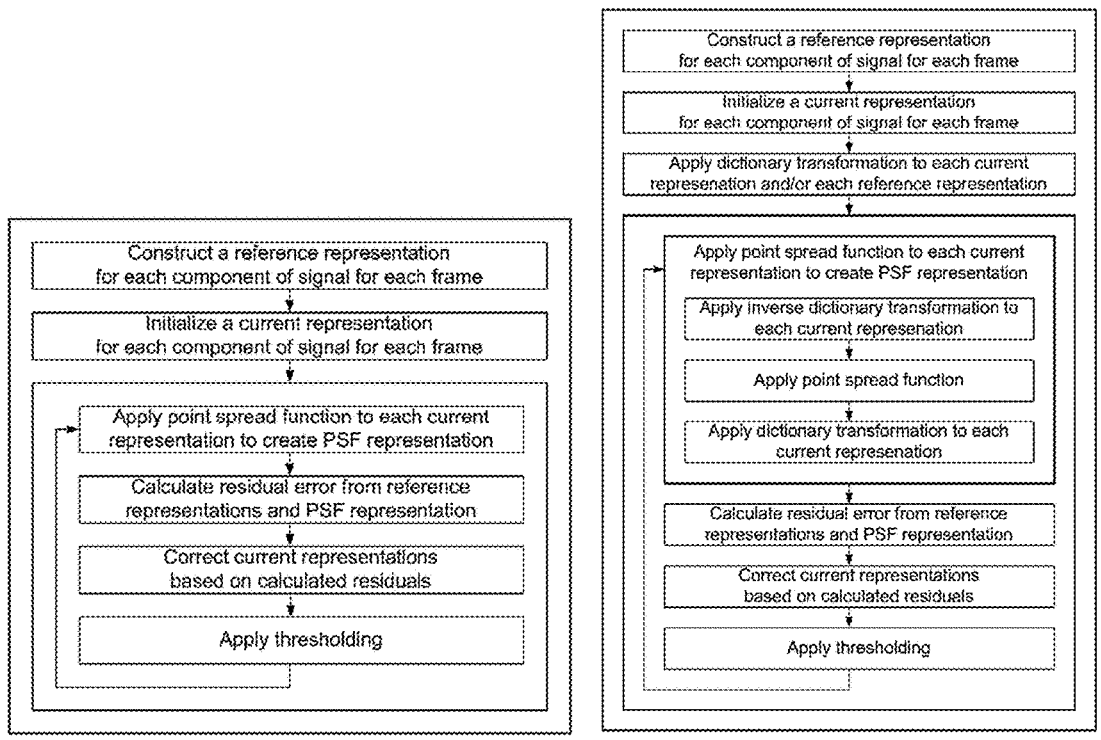
FIG. 9A
FIG. 9B
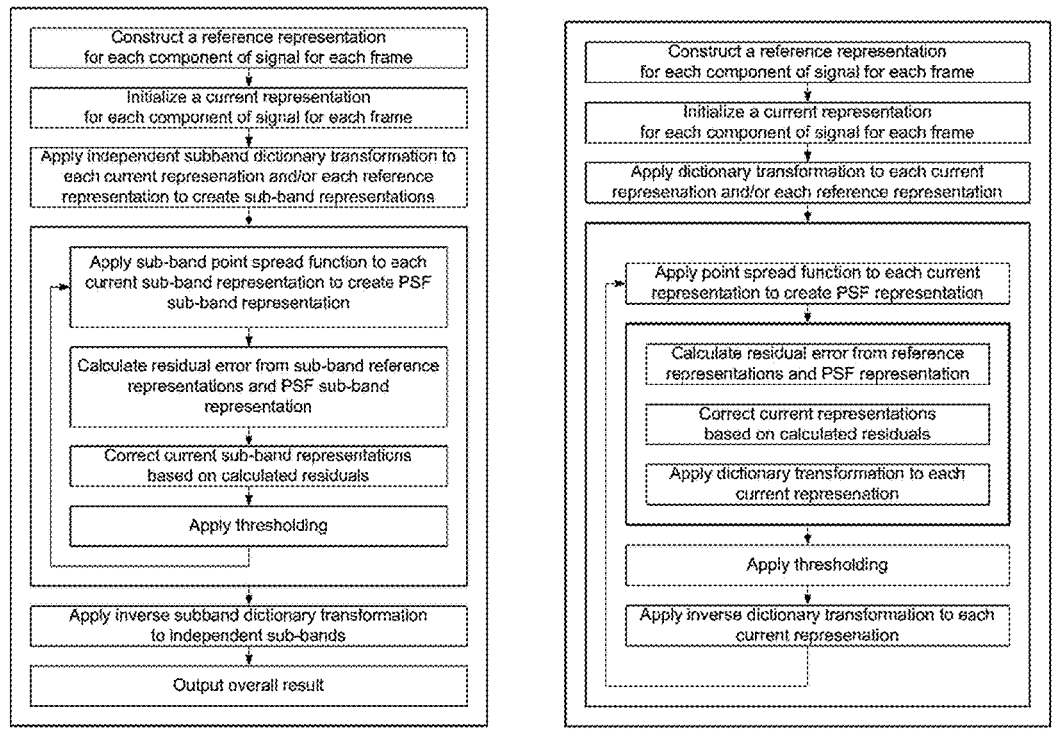
FIG. 9C
FIG. 9D

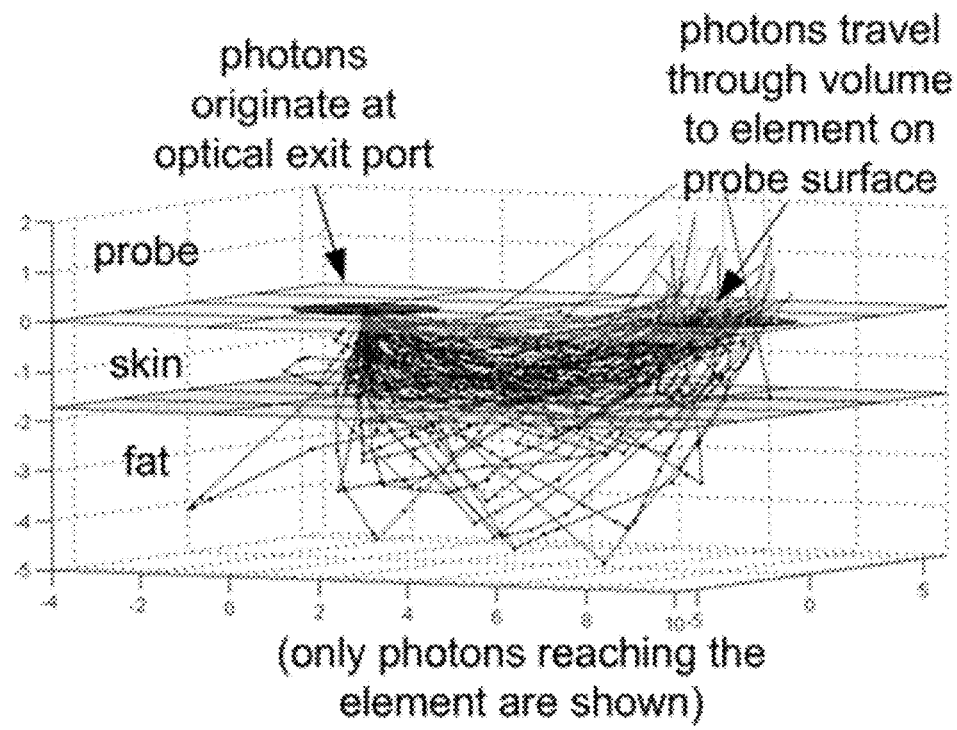
FIG. 17
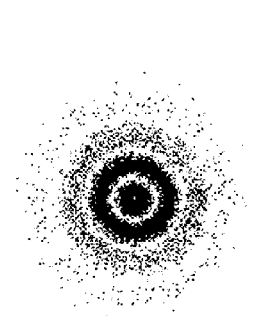 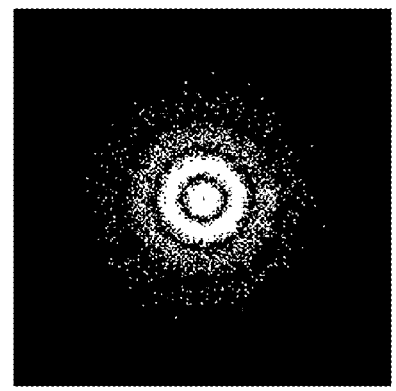
FIG. 18A    FIG. 18B

SYSTEMS AND METHODS FOR COMPONENT SEPARATION IN MEDICAL IMAGING

This application is a non-provisional of, and claims priority to, U.S. Provisional Patent Application No. 61/889,585 filed Oct. 11, 2013, the entire disclosure of which is incorporated herein by reference.

FIELD

The present invention relates in general to the field of medical imaging, and in particular to a medical imaging system which includes a processing subsystem that separates a Direct Acoustic Return (DAR) component from a Secondary Acoustic Return (SAR) component.

BRIEF DESCRIPTION OF THE DRAWINGS

Objects, features, and advantages of the invention will be apparent from the following more particular description of preferred embodiments as illustrated in the accompanying drawings, in which reference characters refer to the same parts throughout the various views. The drawings are not necessarily to scale, emphasis instead being placed upon illustrating principles of the invention.

FIGS. 4A through 4D show examples of applications of reconstruction with component separation.

FIGS. 9A through 9D are block-level flow diagrams showing illustrative embodiments for using sparse representations in component separation.

FIG. 17 is a three-dimensional graph illustrating the trajectory of photons starting from an optical exit position and travelling through the volume to reach a point on the face of the probe before being absorbed.

FIGS. 18A and 18B show an example of a dithered wavelet pattern that can be used to produce a customized initial pressure profile for an ultrasound beam.

DETAILED DESCRIPTION

Figure 1:
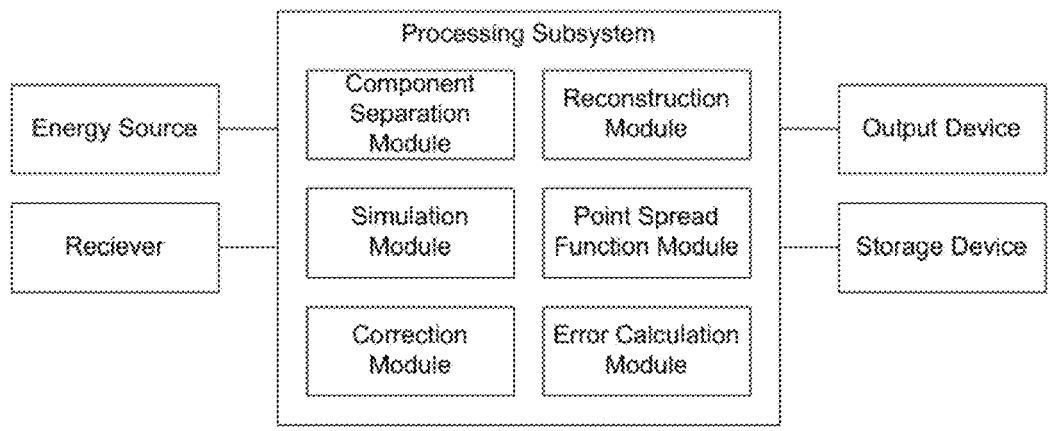
FIG. 1 shows a block diagram of an embodiment of a Component Separation System.

The following description and drawings are illustrative and are not to be construed as limiting. Numerous specific details are described to provide a thorough understanding. Yet, in certain instances, well-known or conventional details are not described in order to avoid obscuring the description. References to one or an embodiment in the present disclosure are not necessarily references to the same embodiment; and, such references mean at least one.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

As used in this description and in the following claims, "a" or "an" means "at least one" or "one or more" unless otherwise indicated. In addition, the singular forms "a," "an," and "the" include plural referents unless the content clearly dictates otherwise. Thus, for example, reference to a composition containing "a compound" includes a mixture of two or more compounds.

As used in this specification and the appended claims, the term "or" is generally employed in its sense including "and/or" (that is, both the conjunctive and the subjunctive) unless the context clearly dictates otherwise.

The recitation herein of numerical ranges by endpoints includes all numbers subsumed within that range (e.g., 1 to 5 includes 1, 1.5, 2, 2.75, 3, 3.80, 4, and 5).

Unless otherwise indicated, all numbers expressing quantities of ingredients, measurement of properties and so forth used in the specification and claims are to be understood as being modified in all instances by the term "about," unless the context clearly dictates otherwise. Accordingly, unless indicated to the contrary, the numerical parameters set forth in the foregoing specification and attached claims are approximations that can vary depending upon the desired properties sought to be obtained by those skilled in the art utilizing the teachings of the present invention. At the very least, and not as an attempt to limit the scope of the claims, each numerical parameter should at least be construed in light of the number of reported significant digits and by applying ordinary rounding techniques. Any numerical value, however, inherently contains certain errors necessarily resulting from the standard deviations found in their respective testing measurements.

The systems and methods are described below with reference to, among other things, block diagrams, operational illustrations and algorithms of methods and devices to process imaging data. It is understood that each block of the block diagrams, operational illustrations and algorithms and combinations of blocks in the block diagrams, operational illustrations and algorithms, can be implemented by means of analog or digital hardware and computer program instructions.

These computer program instructions can be provided to a processor of a general purpose computer, special purpose computer, ASIC, or other programmable data processing apparatus, such that the instructions, which execute via the processor of the computer or other programmable data processing apparatus, implements the functions/acts specified in the block diagrams, operational block or blocks and or algorithms.

Furthermore, the embodiments of methods presented and described as flowcharts in this disclosure are provided by way of example in order to provide a more complete understanding of the technology. The disclosed methods are not limited to the operations and logical flow presented herein. Alternative embodiments are contemplated in which the order of the various operations is altered and in which sub-operations described as being part of a larger operation are performed independently.

In some cases frequency domain based algorithms require zero or symmetric padding for performance. This padding is not essential to describe the embodiment of the algorithm so it is sometimes omitted from the description of the processing steps. In some cases, where padding is disclosed in the steps, the algorithm may still be carried out without the padding. In some cases padding is essential, however, and cannot be removed without corrupting the data.

In some alternate implementations, the functions/acts noted in the blocks can occur out of the order noted in the operational illustrations. For example, two blocks shown in succession can in fact be executed substantially concurrently or the blocks can sometimes be executed in the reverse order, depending upon the functionality/acts involved.

In some cases, block diagrams that illustrate processes with repeated steps (e.g. loops or iterations) do not indicate a criterion for exiting a sequence. This is not intended to imply that such a loop will never exit. It will be apparent to one skilled in the art that a suitable exit criterion can be used (e.g. termination after a fixed number of iterations, termination after a suitable fitness is achieved, etc.).

In some cases, terms such as minimize, maximize, optimize or best-fit are used. This is intended to indicate that a strategy for finding a solution using such terms yields a good solution, but does not generally imply that an absolute optimal solution must be achieved.

Opto-Acoustic Systems

As is known in the art, opto-acoustic systems may take many forms. Generally, an opto-acoustic (or photoacoustic) system acquires an acoustic signal that is created as a result of electromagnetic energy being absorbed by a material. While other types of electromagnetic energy may be used, opto-acoustics is generally associated with the use of electromagnetic energy in the form of light, which light may be in the visible or near infrared spectrum. Thus, an opto-acoustic system has at least one source of electromagnetic energy and a receiver that acquires an acoustic signal that is created as a result of electromagnetic energy being absorbed by a material.

Certain embodiments of an opto-acoustic system are discussed in U.S. patent application Ser. No. 13/842,323 filed Mar. 15, 2013, entitled "Noise Suppression in an Optoacoustic System," the entirety of which is incorporated herein by this reference. The identified patent application describes an embodiment of an opto-acoustic system comprising a plurality of light sources that are an opto-acoustic system capable of outputting pulses of light (at differing predominant wavelengths) to a probe via a light path. Light exits the probe through one or more optical exit ports at the distal end, and the one or more ports may have an optical window across the port. A receiver also at the distal end of the probe is used to sample an acoustic signal. In an embodiment, the receiver may be a multi-channel transducer array which may be used to sample an opto-acoustic return signal at a sampling rate. In an embodiment, the receiver may sample at 31.25 Mhz for a duration of about 65 µs. The samples are stored as a sinogram. In operation, after the distal end of the probe is brought into proximity with a volume to be imaged, the opto-acoustic system as described above may pulse one of its light sources and then sample an acoustic signal. Generally, as discussed in the prior patent application, the predominant wavelengths of the light sources may be selected to be compatible (i.e., highly absorbed) by the features sought to be identified by opto-acoustic imaging.

Although the foregoing describes specific embodiments of an opto-acoustic system, it is presented for illustration only, and the discussion below is not so limited. As discussed in more detail below, portions of the disclosure herein are applicable to an opto-acoustic system having fewer or more light sources, e.g., one light source, or three or more light sources, each of which may have a different predominant wavelength. As will also be apparent, it is also applicable to an opto-acoustic system having multiple light sources capable of producing a pulse at the same wavelength in close succession, or to having one or more light sources (each operating at a different wavelength), and one or more of them being capable of producing pulses in close succession to each other. Moreover, although the foregoing describes embodiments of an opto-acoustic system having transducers capable of outputting ultrasound energy, as discussed in more detail below, such transducers may be unnecessary, and in an embodiment, acoustic receivers will suffice in their stead.

As used herein, the term sinogram refers to sampled data (or processed sampled data) corresponding to a specific time period which may closely follow after one or more light events, or may coincide with one or more light events, or both. Where sinograms are referred to as long sinograms or short sinograms, these generally refer to a sampled acoustic signal from two different light events, each corresponding to a different wavelength of light, the term short sinogram thus refers to the sinogram corresponding to the shorter wavelength of light generating a light event, and the term long sinogram refers to the sinogram corresponding to the longer wavelength of light generating a light event. Because fewer or more than two wavelengths may be used, the use of the terms short and long wavelength are intended to embody the extended context of a system with an arbitrary number of wavelengths.

For illustration throughout, but not by way of limitation, and except where the context reveals otherwise, a sinogram represents a finite length sample of acoustic signal, sampled from an array of receivers. As an example, in an embodiment, a sinogram may represent a sample of 128 channels of a receiver for 65 µs at 31.25 Mhz. While the discussion below may relate to this example sinogram, the specific length, resolution or channel count are flexible, and substantial variation will be apparent to one of skill in the art without departing from the spirit or scope of the present disclosure. Moreover, the examples discussed below generally reflect a linear array of acoustic receivers, however, neither the organization of the receivers nor its number of channels are meant by way of limitation, and substantial variation will be apparent to one of skill in the art without departing from the spirit or scope of the present disclosure.

Sinogram Components

As discussed above, a sinogram may contain, essentially, a sampled recording of acoustic activity occurring over a period of time. Generally speaking, the sinogram is recorded to capture acoustic activity that occurs in response to one or more light events, although, as noted above, the light event(s) may occur shortly before, or during the sampling period, or both. The acoustic activity captured (or intended to be captured) in the sinogram includes the opto-acoustic response, that is, the acoustic signal that is created as a result of electromagnetic energy being absorbed by a material.

For the purposes of discussion of the basic principals involved, as an illustration, a probe-type opto-acoustic system such as described above may be used. The probe is brought in close proximity with a volume of tissue (which is not particularly homogenous), and a sinogram may be created by sampling the opto-acoustic response to one or more light events (from one or more light sources) occurring either shortly before or during the sampling period. Thus, the resulting sinogram contains a record of the acoustic activity during the sampling period. The acoustic activity during the sampling period, however, may contain information that is not related to the one or more light events created for the purpose of making the sinogram. Such information will be referred to as noise for the purposes of this section. Thus, for these purposes, the sinogram comprises noise and opto-acoustic response.

The opto-acoustic response includes acoustic signals that result from the release of thermo-elastic stress confinement—such acoustic signals may originate from one or more optical targets within the volume in response to the light event(s). Some of the opto-acoustic response in the sinogram propagated through the volume essentially directly to the receivers, while some is reflected or otherwise scattered within the volume before arriving at the receivers. The portion of the opto-acoustic response in the sinogram which propagates through the volume essentially directly to the receivers—that is, without substantial reflection or scattering off an acoustic target—is referred to herein as the "Direct Acoustic Return" or "DAR." In addition to noise and DAR, other acoustic signals that reach the receiver and originate in the volume may be caused by a variety of phenomena. The portion of the opto-acoustic response in the sinogram which propagated through the volume but were substantially reflected or scattered before arriving at the receiver—including signals that reach the receiver and originate in the volume, but are the reflected or scattered portions of the wavefronts causing the DAR signal—are referred to herein as the "Secondary Acoustic Return" or "SAR." Since an entire volume is susceptible to some level of opto-acoustic response, all discontinuities in the system (which for the purpose of this section includes the volume and the probe) may create reflections or secondary scattering that occur at the boundaries. For the purposes herein, these scattered and reflected signals, to the extent they reach the receiver, are also deemed SAR. In addition to DAR, SAR and noise, the sinogram may comprise other signals, including, without limitation, surface waves, shear waves and other signals that may be caused by the light event(s) originating within or external to the volume.

In some circumstances, acoustic targets in the volume may slightly deflect an acoustic wave originating from an optical target such that most of the energy of the wave continues to propagate along a slightly deflected path. In these circumstances, the wave originating from the optical target may still be considered DAR (especially where the path deviation is small or signal arrival time deviations are accounted for). This is to say that in some circumstances, e.g., in non-homogenous media, the direct acoustic response may follow a curve rather than a straight line, or the acoustic wave may travel a path that is deflected at certain acoustic boundaries within the volume or coupling medium. In other circumstances, for example, where the speed of sound of the volume or surroundings is not constant or homogenous, a DAR wavefront travelling from an optical target to two acoustic receivers each positioned equal distances away from the target may be reached by portions of the wavefront at different times. Using these general guidelines and the discussion presented below, the difference between DAR and SAR will be apparent to one skilled in the art.

The present disclosure contains three main sections: Component Separation, Coded Probe and Optical Tomography. In the Component Separation section, are disclosed novel methods and apparatus for processing opto-acoustic data to identify, separate or remove unwanted components from the sinogram, and thereby improve the clarity of an opto-acoustic image based thereon. For example, there is a discussion concerning a novel means of removing SAR components that are commonly referred to as backscatter. Also present in the Component Separation section is a disclosure of a novel method and system to identify, separate and remove the effect of surface waves from the sinogram. The Component Separation section also discusses novel methods and apparatus to separate information from multiple light events (at different predominant wavelengths) that are present in the sinogram. The Component Separation section also discusses novel processes and systems to improve the signal-to-noise ratio, among other things, using information from multiple light events (at a single predominant wavelength) that are present in the sinogram. And the Component Separation section discusses a novel method and device for using separated SAR components as functional information and potentially to create functional imagery. Certain embodiments of an opto-acoustic probe that has features which may be useful for application in component separation are discussed in U.S. patent application Ser. No. 13/507,217 filed Jun. 13, 2012 entitled "System and Method for Acquiring Optoacoustic Data and Producing Parametric Maps Thereof," including the CD-ROM Appendix thereto, the entirety of which is incorporated herein by this reference.

The next main section of this disclosure entitled Coded Probe expands on the discussion of removing SAR components, by using the natural path of the photons emitted by a light event to illuminate specific targets external to the volume, and thereby can create known, or expected, SAR components, and/or amplify the existing SAR. It also includes providing specific features and/or properties of the probe itself that can create known, or expected, SAR components, and/or amplify the exiting SAR. The thus-injected SAR components can be used to aid in identification and removal of SAR components, and may further enhance the ability to separate SAR components for use as functional information. The specific targets external to the volume can be encoded to produce specific responses, including differing amplitude and/or frequency responses, and may further be designed to be more or less responsive to one of the several light sources available in a multiple light source embodiment.

The final main section of this disclosure is entitled Optical Tomography, and although optical tomography is known, this disclosure relates to a new method and apparatus for performing optical tomography. Optical tomography (e.g., Diffuse Optical Tomography, Diffuse Optical Imaging and Near Infra-Red Spectroscopy) is a technique that has been applied in several fields of medical imaging, including breast imaging, and has also been used to give neuroscientists the ability to obtain information about the source of neural activity and its time course. To provide an optical tomography image, a light event output, generally a near-infrared laser output is positioned on the tissue surface. The output is generally delivered through one or more optical fiber bundles. Detectors composed of further optical fiber bundles are located a short distance (e.g., a few centimeters) away from the light output. The detectors sense light exiting the tissue to infer the path of light within the tissue, and how it is altered by absorption or scattering as it traverses the tissue. As will be apparent from the coded probe discussion herein, an optical tomography probe can use a traditional near-infrared laser output positioned on the tissue surface, but instead of using optical fiber bundles to detect the light, specific targets can be positioned at similar or varying distances from the light output. As above, the targets can produce an opto-acoustic response which can be detected by one or more acoustic receivers, thus eliminating the need for the optical fiber bundle detectors, or other such optical sensors. In an embodiment, the acoustic receivers may detect waves caused by the specific targets. In an embodiment, the acoustic receivers may detect surface or shear waves caused by the specific targets. In an embodiment, the method and apparatus can be part of a combined opto-acoustic probe. Certain embodiments of an opto-acoustic probe that has features which may be useful for application in diffuse optical tomography are discussed in U.S. patent application Ser. No. 13/746,905 filed Jan. 22, 2013, entitled "Probe with Optoacoustic Isolator", the entirety of which is incorporated herein by this reference.

I. Component Separation

A. DAR vs. SAR Separation

1. System

FIG. 1 shows a block diagram of an embodiment of a Component Separation System. The system in this embodiment includes an energy source, a receiver, a processing subsystem, an output device and a storage device. In an embodiment, the energy source comprises at least one light source for delivering light energy to a volume of tissue and the receiver comprises a transducer array for receiving a resulting acoustic signal. The processing subsystem processes the acoustic signal to separate a DAR component from a SAR component of the acoustic signal, and the output and/or storage device presents and/or stores information about the DAR component, the SAR component, or both. It will be apparent to one skilled in the art that, in an embodiment, other sources of electromagnetic energy may be used in place of a light source. It will also be apparent to one skilled in the art that, in an embodiment, a single receiver or group of receivers may be used in in place of a transducer array. Each of these components is described in more detail below along with other possible components.

In an embodiment of the subject invention, the system is used to isolate and/or remove from an acoustic signal or spatial representation one or more artifacts caused by one or more acoustic wavefronts. As discussed above, acoustic wavefronts can be caused by various sources.

Figure 2:
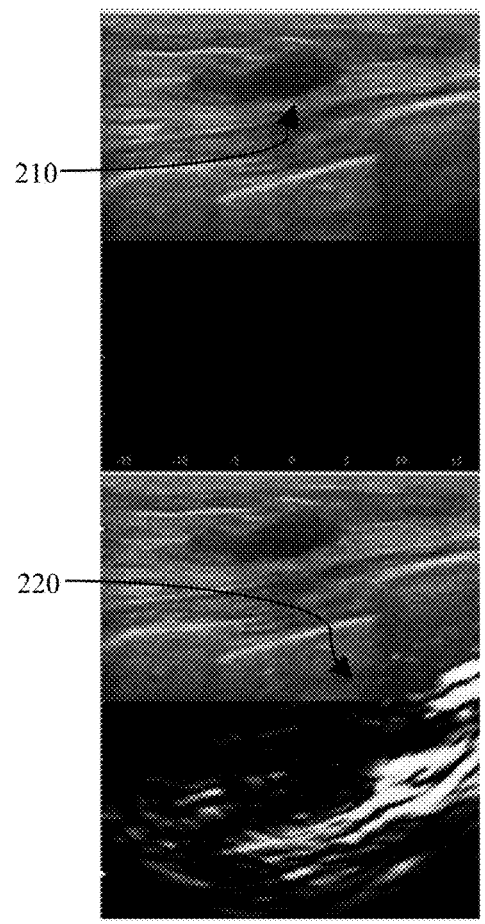
FIG. 2 shows two images reconstructed from an acoustic signal received from a given volume.

In an example, one or more acoustic wavefronts can reflect (or scatter) off one or more acoustically reflective targets in a given volume causing a SAR component of the acoustic signal. FIG. 2 shows two images reconstructed from an acoustic signal received from a given volume. The top image is an ultrasound image, while the bottom image is an opto-acoustic image overlayed on an ultrasound image. The effective depth of the images has been doubled beyond the applicable ultrasound depth to demonstrate the opto-acoustic artifact. The region 210 in the top image represents rib tissue and beneath it is lung tissue in the given volume. It is believed that the wave interference in the bottom image is caused by reflection 220 of an acoustic wavefront originating at the surface off of the lung or rib tissue. The lung or rib tissue and artifacts shown here are merely examples. Acoustic wavefronts may reflect or scatter off of other acoustically reflective targets, including parenchymal tissue, in a volume causing similar or other artifacts. In an embodiment, one or more of the processes or systems described herein can be used to isolate and/or remove such artifacts from signals and/or spatial representations of the volume.

a. Light Source

In an embodiment, the system comprises at least one light (or other energy) source configured to deliver electromagnetic energy to a volume of tissue such that when the electromagnetic energy is delivered an acoustic signal is detectable with at least two components: 1) a DAR component; and 2) a SAR component. The DAR component generally results from temporal stress confinement within one or more electromagnetically absorbent targets in the volume. The SAR component generally results from the incidence of at least one acoustic wavefront on one or more acoustically reflective (i.e., acoustically scattering) targets in the volume. The electromagnetically absorbent targets may also be targets of some acoustic backscatter. Correspondingly, the acoustically reflective targets may also be targets of some electromagnetic energy absorption. Thus, the sets of acoustically reflective targets and electromagnetically absorbent targets need not be mutually exclusive, and may overlap in whole or in part. In an embodiment, the DAR and/or SAR signals are ultrasound signals. In an embodiment discussed in more detail herein, the electromagnetic energy is light energy and the DAR signal is an opto-acoustic return signal. In an embodiment, the electromagnetic energy is energy from part of the RF spectrum, that is, other than light energy. As will be appreciated by one skilled in the art, many, and potentially all portions of the RF spectrum, may cause a DAR signal, and thus, the invention disclosed herein is not limited to use in connection with the visible light energy portion, or even just the light energy portion of the RF spectrum.

b. Transducer Array

In an embodiment, the system includes at least one acoustic receiver configured to receive at least a portion of the DAR signal component and a least a portion of the SAR signal component. In an embodiment, the acoustic receiver may include transducers, which may be located at the distal end of an opto-acoustic probe. In an embodiment, the DAR signal and the SAR signal both reach the acoustic receiver during a single sampling cycle, e.g., a 65 µs of sampling at 31.25 Mhz as described above. At least a portion of the SAR signal may be caused by acoustically reflective targets backscattering acoustic energy from an incident wavefront produced at the surface in response to a light event, as described in more detail below. Because the electromagnetic energy propagates through the volume faster than the acoustic wavefront, with respect to a given target, there is generally a delay of the reception of the SAR signal in comparison to the DAR signal. Thus, under some circumstances, the DAR signal and the SAR signal from a specific target reach the receiver at different times. Under some circumstances, however, the DAR signal and the SAR signal may, at least in part, reach the receiver simultaneously (e.g., when the target is touching the receiver). In an exemplary embodiment, the electromagnetic energy is light energy, which propagates through the volume at or near the speed of light (and in any event, at a speed much faster than the acoustic wavefront) while the acoustic wavefront propagates through the volume at a much slower speed, which speed is nearer the speed of sound (e.g., the speed of sound in tissue). In such an exemplary embodiment, where the acoustic receiver and the source of the electromagnetic energy are at about the same distance from the electromagnetically absorbent and the acoustically reflective targets, it can be assumed that the DAR signal reaches the receiver about twice as fast as the SAR signal from a given target.

In an embodiment, the acoustic receiver may be an array of acoustic receivers. In an embodiment, the receivers in the array of acoustic receivers are transducers, and may be piezoelectric transducers. In an embodiment, the acoustic receiver comprises at least one transducer that is capable of generating an acoustic wavefront that propagate through the volume. In an embodiment, reflective mode imaging is used, where the receivers are proximate to the energy source, which is typically the case when receivers and energy source are both on a handheld probe. In an embodiment, the electromagnetic energy is delivered via a probe and a receiver may be positioned on the probe, and in particular, it may be positioned on the distal end of the probe (i.e., the end closest to the volume). In an embodiment, where, for example, a transmission mode is utilized, a receiver may be positioned at a location near or adjacent to the volume, but not proximate the source of the electromagnetic energy delivery. In transmission mode, the receiver is commonly placed on the opposite side of the volume from the electromagnetic energy source. When an incident wavefront originates substantially opposite the volume to the receiver, an acoustic scattering target in the volume may predominantly cause an acoustic reflection that does not reach the receiver, but rather the scattering may affect the acoustic transmission of the incident wavefront that is measured by the receiver. Since, acoustically scattering targets may reflect and transmit acoustic wavefronts according to a relationship, an acoustically reflective target may also be considered as an acoustically transmissive target and vice versa. The reflective scattering strength of an acoustically reflective target does not always equal its transmissive scattering strength. In an embodiment, no distinction is made between an acoustically scattering target, and an acoustically reflecting target or an acoustically transmissive target. In an embodiment, a system is designed to provide stronger analysis of signals resulting from reflections of acoustic targets rather than the signals resulting from an acoustically scattering target or an acoustically transmissive target. For example, when wavefronts originating from the surface of a handheld probe reach a target, the reflected wavefront from the target may be directed back towards the probe, but the transmitted part of the wavefront may keep going and may not reach an acoustic receiver on the probe. Hence, in some circumstances, some transmitted or reflected scattering reflections may not be received by receivers or analyzed by the processing subsystem described next.

c. Processing Subsystem

With further reference to FIG. 1, in an embodiment, a processing subsystem is adapted to analyze the acoustic signals to obtain information regarding electromagnetically absorbent and/or acoustically reflective targets in the volume. In an embodiment, the processing subsystem analyzes the acoustic signals (e.g., in sinograms) to produce a spatial representation of the targets in the volume. In an embodiment, the subsystem uses a time delay between the reception of the DAR signal and the SAR signal to better analyze the signals. In an embodiment, the system separates the DAR signal (or spatial representation thereof) and the SAR signal (or spatial representation thereof) and processes them differently based on the time delay and/or other parameters.

In an embodiment, the processing subsystem comprises: 1) a reconstruction module capable of analyzing acoustic signals (such as the DAR signal and the SAR signal discussed above) to produce estimated spatial representations of targets in a volume (such as the electromagnetically absorbent targets and the acoustically reflective targets discussed above); and 2) a simulation module capable of analyzing spatial representations of targets in a given volume (such as the estimated spatial representations produced by the reconstruction module) and generating acoustic signals that might be produced by applying electromagnetic energy to the given volume. In an embodiment, the reconstruction and simulation modules perform adjoint operations: the reconstruction module obtaining acoustic signals and producing spatial representations; and the simulation module obtaining spatial representations (such as those produced by the reconstruction module) and producing (e.g., back-projecting) acoustic signals that might be produced when electromagnetic energy is applied to a volume with the given spatial representations. In an embodiment, the simulation module performs a forward projection. In an embodiment, the simulation module further preforms additional processing which may include accounting for in-homogeneity, propagation delay, denoising, or other additional processing. In an embodiment, the forward projection may use a system transfer matrix. In an embodiment, the reconstruction module performs a backward projection. In an embodiment, the backward projection may be the Hermitian adjoint of the forward projection. In an embodiment, the reconstruction module further performs additional processing which may include accounting for in-homogeneity, propagation delay, adaptive filtering, or other additional processing. The spatial representations and acoustic signals can be passed, received, or stored in any convenient format, and various formats for the same will be apparent to one of skill in the art in view of this disclosure. In an embodiment, the spatial representations are passed, received, or stored as an array of pixels, a bit map, or other image format. In an embodiment, three or higher dimensional representations may be passed, received, or stored. In an embodiment, the acoustic signals may be passed, received, or stored as sinograms. Other formats and representations are known in the art and can be used in connection with the disclosures herein, such other formats and representations including, without limitation, transformed domains such as wavelet or similar transformations, dictionaries, or a representation basis, which may improve performance. Accordingly, the spatial representation can include wavelet representation of the spatial domain or other such applied transformation to the spatial domain, where applicable. In an embodiment, during various stages of processing, a representation may switch to and from a transformed representation represented in different basis such that the transformation substantially preserves all of the data (e.g. a wavelet transformation applied to a spatial representation). Such switches may or may not be fundamental to the performance of the processing (e.g., performing thresholding on a sparse representation); however, the stages of processing where transformation does occur may vary between implementations. Hence, in an embodiment, such transformations may be inserted in various stages of processing. The correctness and applicability of applying such transformations should be apparent to one skilled in the art.

In an embodiment, the spatial representation may be a 2D array representing a 2D slice of the volume. In an embodiment, the spatial representation may be a 3D array representing a 3D region of the volume. In an embodiment, the spatial representation may be a wavelet representation of a 2D slice or 3D region of the volume. In an embodiment, when a 1D array of transducers is used to record sinogram measurements and a 3D spatial representation of the volume is used, iterative minimization techniques (such as those described below), may be applicable to determining out-of-plane structures. Similarly, application of iterative minimization techniques may be advantageous when a 1.5D or 2D array of transducers is used. The choice of the basis for the 3D spatial representation (e.g., wavelet) can affect processing speed and/or image quality performance. Hence, in an embodiment, the steps of 1) iteratively reconstructing a 3D representation of the volume, then 2) extracting a 2D slice from the 3D representation, may be employed (a) to reduce streaking from out-of-plane structures, which streaking may occur in a 2D reconstruction, and (b) to determine the out of plane structures. In an embodiment, the orientation of vessels or structures crossing through the imaging plane may be determined using the same technique followed by further analyzing for determining orientation of the vessels or structures.

i. Simulation Module

As discussed above, in an embodiment, there is a simulation module capable of analyzing spatial representations of targets in a given volume (such as the estimated spatial representations produced by the reconstruction module) and generating acoustic signals that might be produced by applying electromagnetic energy to the given volume. In an embodiment, the simulation module produces at least two separate acoustic signals for a given volume: a simulated DAR signal that might be produced by temporal stress confinement of electromagnetically absorbent targets in the given volume (such as the electromagnetically absorbent targets discussed above); and a simulated SAR signal that might be produced by incidence of one or more acoustic wavefronts on acoustically reflective targets within the given volume (such as the acoustic wavefronts and acoustically reflective targets discussed above). In an embodiment, the DAR and SAR simulations are performed independently, such that the simulation module may simulate each component separately. In an embodiment, the electromagnetic energy directed to the volume is light energy and the simulated DAR signal produced by the simulation module is a simulation of the portion of the opto-acoustic response that would propagate through the volume essentially directly to the receivers. In an embodiment, the simulated SAR signal is a simulated ultrasound (US) backscatter signal produced by backscatter of an acoustic wavefront(s). In an embodiment, the acoustic wavefront(s) originates at or proximate to the surface of the volume and may cause ultrasound backscatter. Ultrasound backscatter can be modeled as a linear system and approximations to treat an unknown scatter field with a single or dual parameter model can be used. In an embodiment, different processes or parameters may be used to simulate the separate acoustic signals. In an embodiment, different and/or varying parameters may be used for the speed at which sound travels through the volume. In an embodiment, a value for the speed of sound in the volume is developed from previous testing, analysis, or computation. In an embodiment, a presumed, known, or computed speed of sound profile or propagation delay profile is provided as input to the simulation (and/or reconstruction) module(s).

In an embodiment, it can be assumed that the acoustic receiver and the origin of the acoustic wavefront are at substantially the same distance (r) from targets in the volume. Such an assumption represents a close approximation where the origin of the acoustic wavefront is quite proximal to a probe (e.g., a shallow skin layer, etc.) when compared to the depth of one or more of the targets. Where the electromagnetic energy is light energy, it may be assumed that the time required for the light energy to reach the targets in the volume and cause temporal stress confinement is negligible. Thus, it is inferred that sound energy in the DAR signal, which only travels from the targets, will reach the receiver after traversing the distance (r). While, sound energy in the SAR signal, which must first travel from the wavefront source to the targets and then from the targets to the receiver, will reach the receiver after traversing twice the distance (r+r). Based on these assumptions, about half the speed of sound (r/2r) is used to simulate the SAR signal to account for the increased distance the sound energy must travel through the volume.

In an embodiment, it can be assumed that the acoustic wavefront travels a depth (y) from its source to the targets in the volume, but an attempt is made to account for the fact that the acoustic receiver may be positioned at an angle (theta) to the depth vector (y) traveled by the acoustic wavefront. Thus, it is assumed that the sound energy in the DAR signal travels the distance (r), while the sound energy in the SAR signal travels the distance (r) in addition to the depth (y). Hence, the total distance traveled (y+r) can be calculated as r(1+cos(theta)). In an embodiment, a slower speed of sound is used to simulate the SAR signal to account for the additional distance (y) traveled by the sound energy in that signal. In an embodiment, the speed of sound used to simulate the SAR signal is set at about 1/cos(theta) times the speed of sound. In an embodiment, a measured or presumed speed of sound profile is used to calculate the expected propagation times for one or more of the acoustic signals. In this configuration, the SAR may interfere with the DAR.

In some reflective mode or transmission mode configurations, it may be possible to position the energy source and receiver such that SAR due to scatter and DAR do not substantially interfere, but in other situations it is not possible. In an embodiment, an acoustic wavefront may be used to compute the speed of sound prior to or during component separation. In an embodiment, this wavefront may be produced proximate to the surface of the volume when the probe is configured in a reflective mode. In an embodiment, this wavefront may be produced as a result of the application of electromagnetic energy to passive elements on, in, or near the probe or the volume. In an embodiment, the probe includes ultrasound transducers (which may also act as the receiver discussed above) and the wavefront is produced by the transducers. Component separation itself may facilitate computing the speed of sound when reflective mode passive elements are used by separating interfering components of the acoustic signal. In an embodiment, the acoustic wavefront may originate from a handheld probe. In an embodiment, an array of receivers are used and the propagation times for reconstruction are adjusted separately based on the speed of sound profile and a measured or presumed propagation time to the receiver from the source of the sound. In an embodiment, the propagation times used are adjusted separately based on the speed of sound profile and a measured or presumed propagation time for each pixel or element in the spatial representation. In an embodiment, the propagation times used are adjusted separately based on the speed of sound profile and a measured or presumed angle for each angular ray of the spatial representation.

The following processing steps are an illustrative embodiment of an algorithm for simulating DAR, which can be adapted to simulate SAR (and/or PAB and/or ASW as further discussed below), using a look-up-table approach:
  a. Allocate a three dimensional array to store a look-up table where each value in the table corresponds to y-axis pixel depth coordinate in an image, and the table is indexed by sample number, x-axis pixel coordinate, and transducer channel.
  b. For each combination of sample number, x-axis pixel coordinate, and transducer channel, set the corresponding value in the table to the corresponding y-axis coordinate in the image. This can be determined by:
    i. determining the expected distance travelled, which is the current sample number divided by sampling rate times speed of sound;
    ii. determining the x-axis distance between the current x-axis pixel coordinate and the current transducer channel;
    iii. determining the y-axis depth using the Pythagorean theorem which yields the result as the real part of the square root of the square of distance travelled less the x-axis distance; and
    iv. converting the y-axis depth to a y-axis pixel coordinate and storing the result in the table.
  c. For each combination of sample number, x-axis pixel coordinate, and transducer channel, allocate a weight table and determine the weight for the table. If the y-axis depth is greater than zero and less than a maximum then the weight may correspond to the weight used by weighted delay-and-sum reconstruction (described below), otherwise a value of zero may be used for the weight.
  d. Allocate an output sinogram array and set all values to zero.
  e. Input an array corresponding to the spatial representation that is to be simulated.
  f. For each combination of sample number, x-axis pixel coordinate, and transducer channel:
    i. determine the corresponding y-axis pixel coordinate from the lookup table;
    ii. determine the corresponding weight value from the weight table by:
      1. retrieving the value corresponding to the current x-axis pixel and looked-up y-axis pixel for the input spatial representation;
      2. multiply the retrieved value by the corresponding weight value; and
      3. adding the result of the multiplication to the sinogram element corresponding to the current transducer channel and sample number; and
  g. If applicable, apply a shift invariant or shift variant filtering to the channels of the sinogram In the above illustrative embodiment, steps a) through c) may only need to be computed one time. In an embodiment, the weights from step c) may be the same as the weights from weighted delay-and-sum reconstruction, or the backward projection, in which case, the simulation will approximate the adjoint operation of the reconstruction. In an embodiment, the SAR simulation may use a different speed of sound as a surface approximation, such as half the speed of sound. In an embodiment, the SAR simulation may replace step b.iii.) above for determining the depth in the y-axis with determining depth in the y-axis from the geometry as the square of distance travelled less the x-axis distance all divided by two times the distance travelled, which takes into account that the wavefront must travel from the surface to the acoustic target and then travel to a transducer. In an embodiment, the shift invariant or shift variant filtering can be used to model reflections from a coded wavefront, the filter coefficients may be determined in relation to an expected impulse response of the probe. In an embodiment, the coded wavefront may be based on a measured skin response, or other such coding from probe features as described below. In an embodiment, the filtering may be performed in step f.ii.3) and the adding of a filtered result may affect multiple sinogram elements. In an embodiment, the entire output sinogram may be shifted by a number of samples to compensate for a delay with respect to the timing of an energy event. In an embodiment, the look-up-table and weights calculation is replaced by a fast optimized computation computed on the fly. In an embodiment, the filtering may apply a spatially dependent impulse response applicable to SAR.

ii. Reconstruction Module

As discussed above, in an embodiment, the processing subsystem includes a reconstruction module capable of analyzing acoustic signals received from a volume of tissue (such as the DAR signal and the SAR signal discussed above) and producing spatial representations of the volume. In an embodiment, the reconstruction module estimates positions of targets as spatially represented in the volume (such as the electromagnetically absorbent targets and the acoustically reflective targets discussed above). In an embodiment, the acoustic signals are provided in the form of one or more sinograms containing processed or unprocessed acoustic data. In an embodiment, the reconstruction module is capable of producing a least two separate spatial representations of a volume from a given acoustic signal or sinogram. In an embodiment, the reconstruction module can be applied to produce both a DAR and a SAR representation of the volume from a given sinogram. Various reconstruction methods are known in the art. Exemplary reconstruction techniques are described below.

Figure 3A:
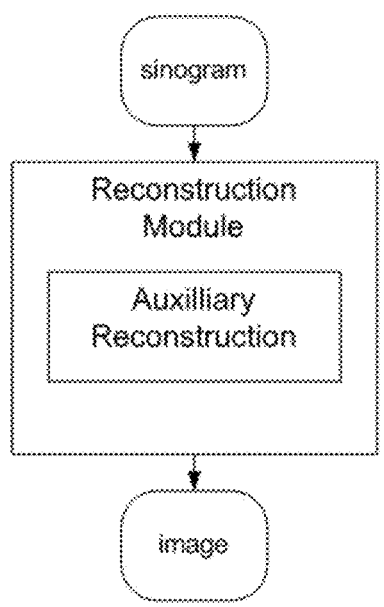
FIG. 3A is a block-level process flow chart illustrating the process flow associated with a reconstruction module.

FIG. 3A is a block diagram illustrating the process flow associated with a reconstruction module in accordance with an embodiment. Although the term "reconstruction" as used herein refers to a process or module for converting the processed or unprocessed data in a sinogram into an image (or other spatial representation) representing localized features in a volume, it is important to understand that such reconstruction can be done at many different levels. For example, reconstruction can refer to a simple function that converts a sinogram into an image representation such as through the use of the weighted delay-and-sum approach described next. Or, in an embodiment, reconstruction can refer to a more complex process whereby a resultant image representation is improved by applying a reconstruction function or module at a different level of abstraction (also referred to here as "auxiliary reconstruction") along with any other signal or image processing techniques. Consequently, a reconstruction algorithm may include an auxiliary reconstruction processing stage, as shown in FIG. 3A.

As an example, an iterative reconstruction algorithm may apply an auxiliary reconstruction function two or more times. In an embodiment, component separation can itself be part of a larger reconstruction function because part of improving a reconstructed image of the volume may include separating (e.g., removing) unwanted components of the sinogram. Various applications of reconstruction with component separation are shown in FIGS. 4A through 4D. In each of these figures, the process encompassed by the dotted line can itself be considered a "reconstruction" as the input is a sinogram and the output is an image. Although, in the examples illustrated in FIGS. 4A through 4D, each process produces two separate images (as further described below). In an embodiment, one of the two separate images may be ignored, discarded or used for other purposes. In the embodiment of FIG. 4A, a component separation process receives sinogram data as input and outputs a DAR image and a SAR image. In the embodiment of FIG. 4B, a process includes an auxiliary reconstruction process and a component separation process. The auxiliary reconstruction process receives as input the sinogram data and produces as output a combined image. A component separation process then receives the combined image as input and outputs a DAR image and a SAR image. In the embodiment of FIG. 4C, a process includes an auxiliary reconstruction process, an initialize values process and a component separation process. The auxiliary process takes as input the sinogram data and outputs a DAR image. The initialize values process outputs a SAR image. A component separation process receives as input the DAR image and the SAR image, and outputs a DAR image and a SAR image. In the embodiment of FIG. 4D, a process includes a component separation process, a first auxiliary reconstruction process, and a second auxiliary reconstruction process. The component separation process receives as input the sinogram data and outputs a DAR sinogram and a SAR sinogram. The first auxiliary reconstruction process receives as input the DAR sinogram and outputs a DAR image, while the second auxiliary reconstruction process receives as input a SAR sinogram and outputs a SAR image.

In an embodiment, reconstruction can be based on a weighted delay-and-sum approach. In an embodiment, the weighted delay-and-sum approach implements a backward projection. The weighted delay-and-sum algorithm may optionally be preceded by a transform operator. In an embodiment, the weighted delay-and-sum algorithm can operate on complex-valued data. In an embodiment, weights may be used by reconstruction to represent the contributions from each sample to be used for each pixel, and organizationally, the method used to generate the weights may be considered part of image reconstruction. In an embodiment, the weights may be tuned based on an analysis of the collected data.

Generally, reconstruction takes as input processed or unprocessed channel data, i.e., a sinogram, and uses this information to produce a two dimensional image of a predetermined resolution.

The dimensions of an individual pixel (in units of length) determine the image resolution. If the maximum frequency content in the sinogram data is too high for the selected resolution, aliasing can occur during reconstruction. Thus, in an embodiment, the resolution and sampling rate may be used to compute limits for the maximum frequency content that will be used in reconstruction, and thus to avoid frequency content that is too high for the selected resolution.

In an embodiment, the sinogram can be low-pass filtered to an appropriate cutoff frequency to prevent or mitigate aliasing.

Conversely, if the sampling rate is too low to support the image resolution, then, in an embodiment, the sinogram can be upsampled and interpolated so to produce a higher quality images. While the two dimensional image can be any resolution, in an exemplary embodiment, the image can comprise 512×512 pixels. In an embodiment, the image can comprise 1280×720 pixels. In yet another exemplary embodiment, the image may comprise 1920×1200 pixels. In an embodiment, the horizontal resolution is at least 512 pixels wide, and may be up to 2560 pixels wide or more, and the vertical resolution is at least 512 pixels high, and may be up to 1600 pixels high or more. In an embodiment, the image resolution conforms to the resolution of an existing display device or standard, or a known storage format, e.g., 640× 480, 800×600, 1280×1024, 1280×720, 1920×1080, 1920× 1200, 2560×1600, 3840×2160, 4096×2160, 4096×1714, 3996×2160, 3656×2664 and/or 4096×3112. Generally, a processing time (and thus performance) and/or memory constraint tradeoff is required to attain higher resolution.

A two dimensional image may represent variations in the volume, such as structures, blood, or other inhomogeneities in tissue. The reconstruction may be based upon the first propagation time from each location in the tissue to each transducer and the contribution strength of each sample to each pixel. The signal intensities contributing to each pixel in the image are combined to generate the reconstruction.

In an embodiment, the DAR and SAR reconstructions are performed independently, such that the reconstruction module may simulate each component separately. The following processing steps are an illustrative embodiment of a reconstruction algorithm using a weighted delay-and-sum technique for DAR (that can be adapted to reconstruct SAR and/or ASW):

a. Allocate an output image array and set all values to zero;
b. For each transducer channel:
   i. For each pixel in the output image array:
      1. Access the delay (in samples) from Sample Delay Table for that channel and pixel, and then retrieve the sample (from the sinogram) corresponding to the channel and delay;
      2. Access the weight from Weights Table corresponding to the channel and pixel;
      3. Multiply the sample by the corresponding weight; and
      4. Add and store the result with in location of the output image array corresponding to the destination pixel.

The weights table is a table representing the relative contribution of each sample in the sinogram to each pixel in the resulting image. In an exemplary embodiment, for relative computational efficiency, the same weights table can be used for the real and imaginary components of a complex sinogram. In an embodiment, separate weights table can be used for each of the components of a complex sinogram. In an embodiment, one complex weights table can be used for the real and imaginary components of a complex sinogram. In an embodiment, separate complex weights table can be used for each of the components of a complex sinogram. In an embodiment, a complex weights table can be used to account for standing-wave type patterns in the image that are the result of the system geometry.

The weights table can be used to establish something akin to an aperture in software. Thus, in an embodiment, where a wider aperture is desired, more weight is given to off-center samples. Stated in other words, for example, for a given transducer, usually no sample would be given more weight than the sample directly beneath the transducer, and for the purposes of illustration, consider that the weight for a given sample directly beneath the transducer is 1. Consider further the relative contribution of samples that are at 15, 30 and 45 degrees from center, but equidistant from the transducer. To narrow the aperture, those samples could be weighted 0.5, 0.25 and 0.12 respectively, while to widen the aperture, those same samples could be weighted 0.9, 0.8 and 0.7 respectively. The former would provide only a slight (12%) weight to samples received from a source at 45 degrees from center, while the latter would provide the same sample much higher (70%) weighting. In an embodiment, the system displaying the opto-acoustic output—which may, but need not be the same as the system acquiring the sinogram—would provide the operator the ability to vary this parameter (i.e., the software aperture) when viewing opto-acoustic images.

In an embodiment, a very large table contains a mapping of relative weight and delay for each pixel and transducer. Thus, in an embodiment where a target image is 512×512 pixels and the probe 102 has 128 channels (i.e., transducers), there are 33,554,432 weight entries and the same number of delay entries. Similarly, in an embodiment where a target image is 1280×720 pixels and the probe 102 has 128 channels (i.e., transducers), there are 117,964,800 of each type of entry. In an embodiment where a target image is 1920×1200, and the probe has 256 channels, there are almost 600 million of each type of entry. Thus, as mentioned above, a processing time (and thus performance) and/or memory constraint tradeoff is generally required to create a target image having a higher resolution.

Image Reconstruction—Calculate Weights and Delays

As discussed above, in the illustrative embodiment of a delay-and-sum reconstruction algorithm, a Weights Table may be employed. An algorithm may be used to calculate the Sample Delay Table and Weights Table for each transducer. In an embodiment, the data comprising Sample Delay Table(s) correlates the estimated contribution of each transducer to each pixel, while the data comprising the Weight Table(s) provides an estimate of the relative weighting of the contribution of each transducer to each pixel as compared to the other contributions to that pixel. In an embodiment, the Weights Table may be used to account for angular apodization with respect to the transducer's norm, power of the laser, time gain control, light attenuation within the tissue, skin thickness, coupling medium characteristics, patient specific variables, wavelength specific variables and other factors.

In an embodiment, each of the tables corresponds in size (in pixels) to the two dimensional image output by image reconstruction, and a plurality of each table are created, one for each channel. In the illustrative embodiment above, each Sample Delay Table correlates the pixels of the target image with the samples in an sinogram, thus, one Sample Delay Table (which is specific to a channel) will identify for each pixel in the image, the specific sample number in that channel that is to be used in calculating that pixel. Similarly, in the illustrative embodiment above, each Weights Table correlates the pixels of the target image with the weight given to the sample that will be used; thus, one Weights Table (which is specific to a channel) will identify for each pixel in the image, the weight to be given to the sample from that channel when calculating the pixel.

X- and Y-coordinates of the image pixels are calculated using the input information on the image size and location. In an embodiment, the time delays for DAR are calculated for each transducer and each pixel by knowing the distance between pixel and transducer and the speed of sound. If an acoustic matching layer with different speed of sound is used, then separate time delays are calculated inside and outside of the matching layer and added together, resulting in the overall transducer-pixel delay. The weights are calculated for each transducer and each pixel, depending on their relative location. The distance and angle between the transducer-pixel vector and transducer's norm are taken into account, as well as the depth position of an individual pixel. In an embodiment, the system calculating the weights and/or delays—which may, but need not be the same as the system acquiring the sinogram or displaying the images reconstructed there-from—would provide the operator the ability to vary parameters used in processing. In an embodiment, the system calculating the weights would provide the operator the ability to vary the bases for the weight calculation, thus, e.g., giving more or less weight to off-center acoustic data. In an embodiment, the system calculating the weights would provide the operator the ability to controls whether linear or power relationships are be used in calculation of the weights.

In an embodiment, the SAR component may have a separate weights table, or a separate delays table from DAR. In an embodiment, the SAR delays table may be computed such that the time delays reflect the distance of an acoustic wave that travels from the surface to the target and then to a transducer. Thus, the time delays are calculated for each transducer and each pixel based on the distance between the pixel and the transducer, the speed of sound (or an estimate thereof), and the depth of the pixel. In an embodiment, the weights table for SAR may account for the acoustic attenuation of the wavefront as it propagates to the depth of the pixel. In an embodiment, the weights for a pixel to a transducer for DAR may be computed as the depth of the pixel divided by the distance from the pixel to the transducer all raised to a cubed power and multiplied by an exponentially decaying function of the pixel depth. In an embodiment, the weights for a pixel to a transducer for SAR may be computed as the depth of the pixel plus the distance from the pixel to the transducer all divided by the distance from the pixel to the transducer all raised to a cubed power multiplied by an exponentially decaying function of the pixel depth plus the distance from the pixel to the transducer.

Once reconstruction is complete, post-processing may be performed on the resulting image or images.

In an embodiment, image reconstruction may be based on Adaptive Beamforming, Generalized Sideband Cancellation, or other methods as are known in the art. In an embodiment, techniques for reconstruction may be based on determining cross-correlations functions between channels and/or maximizing a sharpness objective of the image.

In an embodiment, a method to reconstruct a volume may consist of decomposing a cross-section or volume into radial wavelets, the radial wavelets representing opto-acoustic sources (the measured opto-acoustic return signal of radial opto-acoustic sources in particular are presumed to obey a simple closed form equation), the technique of Wavelet-Vaguelette decomposition may be used to relate the wavelets and vaguelettes between the image domain and the sinogram and to thereby determine the intensities of the radial wavelets in the image, and thus to reconstruct the image. In an embodiment, the projection of radial wavelets from the image domain into the sinogram domain (i.e., vaguelettes) can be used in conjunction with other image formation techniques prior to determining the intensities of the radial wavelets. In an embodiment, adaptive beamforming, or wavelet de-noising involving thresholding can be performed on the radial-wavelet projections as a stage of such a reconstruction.

Iterative reconstruction involves applying a reconstruction (and/or simulation) operation(s) one or more times to move closer to a solution. In an embodiment, reconstruction may be based on Iterative Minimization or Iterative Maximization, such as, for example, L1-minimization or L2-minimization. Iterative Minimization algorithms for reconstruction and enhancement require high computational load and thus, are often not considered applicable for real-time imaging. Nevertheless, in accordance with embodiments disclosed herein, in some circumstances, it is feasible for real-time opto-acoustic reconstruction of a cross-section of a volume to be performed using an L1-minimization algorithm. In an exemplary embodiment for performing L1-minimization reconstruction in real-time on a 2D cross-section of a volume, the Fast Wavelet Iterative Thresholding Algorithm is used, and combined with the Helmholtz wave equation in the frequency-domain, which can be efficiently used to represent opto-acoustic wave propagation yielding a diagonalizable (or nearly diagonalizable) system matrix. In an embodiment, the pixels of the image may be decomposed into radial wavelets, the decomposition represented in the frequency domain as radial subbands, and the radial subbands used in the iterative thresholding. See, e.g., U.S. patent application Ser. No. 13/507,217, which has been incorporated herein by reference. In an embodiment, each sub-band of the representation may be reconstructed and/or simulated substantially independently. In an embodiment, the iterations may be performed on sub-bands independently as though each sub-band is a separate iterative reconstruction problem. In an embodiment, a Fast Wavelet Iterative Thresholding Algorithm or Fast Weighted Iterative Soft Thresholding Algorithm may be used where the system matrix is found empirically rather than through using an ideal equation.

When the laser illuminates the volume of tissue with at least a portion of the surface being adjacent to a medium that is not perfectly matched to the acoustic properties of the volume, the propagating acoustic wave may reflect—at least in part—off the unmatched surface and propagate into the volume as an incident wave-front. The incident wave-front can further reflect off acoustic discontinuities in the tissue and interfere with the opto-acoustic return signal creating an artifact. This artifact can be separated from the opto-acoustic return signal using, e.g., an iterative minimization technique. In an embodiment, an image mapping the intensity of this artifact can be produced. In an embodiment, the image mapping the intensity of this artifact is an image of a SAR component.

In an embodiment, a pattern detection classifier can be applied to an opto-acoustic return signal, wherein the classifier output reflects the strength of a particular indicator as a function of time (or distance). Accordingly, upon obtaining measurements from multiple transducer positions, the classifier output can be beam-formed to localize the source (i.e., phenomenon) causing the pattern detected. An image produced from the beam-formed classifier output may suffer from blurring, reconstruction artifacts, and streak artifacts, which may be particularly acute in a limited-view case. These artifacts may result at least in part because the pattern classified signal may lack information concerning signal strength that is part of a non-pattern classified sinogram, and its intensity is related to the presence of the pattern, not necessarily on the distance that the transducer is located from the source of the pattern. The classifier output of a classified opto-acoustic signal, however, can be "fit" into the propagation model of the Helmholtz equation where the classifier output is characterized as originating from an instantaneous source term at a given position. Thus, to reduce the streaking, blurring and artifacts a parametric map of the pattern classified signal can be formed using techniques for reconstruction and deconvolution other than simple beamforming. Application of, e.g., an iterative minimization technique can be used to reduce streaking and thus better localize the source of the pattern. Different types of classifiers and reconstruction techniques may have different considerations that apply. In an exemplary embodiment, a parametric map of the classified quantity can be produced by using an iterative minimization technique, where the system matrix is formed as it would be had the source been an opto-acoustic signal. In an embodiment, the sparse basis representation used by, e.g., L1 minimization, may serve to localize the source of the pattern and hence reduce artifacts. Thus, rather than applying the reconstruction technique to an opto-acoustic return signal, it may be applied to classifier output, where the classifier output is represented in the form of a sinogram. In an embodiment, the reconstruction technique is applied as though the classifier output were an opto-acoustic return signal. In an embodiment, further processing, such as taking a complex envelope of the classifier output, filtering, or deconvolving the classifier output may be performed prior to reconstruction. In an embodiment, the classifier may be designed to discriminate between normal and abnormal branching blood vessels in tissue. In an embodiment, the pattern detection classifier may be used to detect signals resulting from a coded probe as described below.

Figure 5:
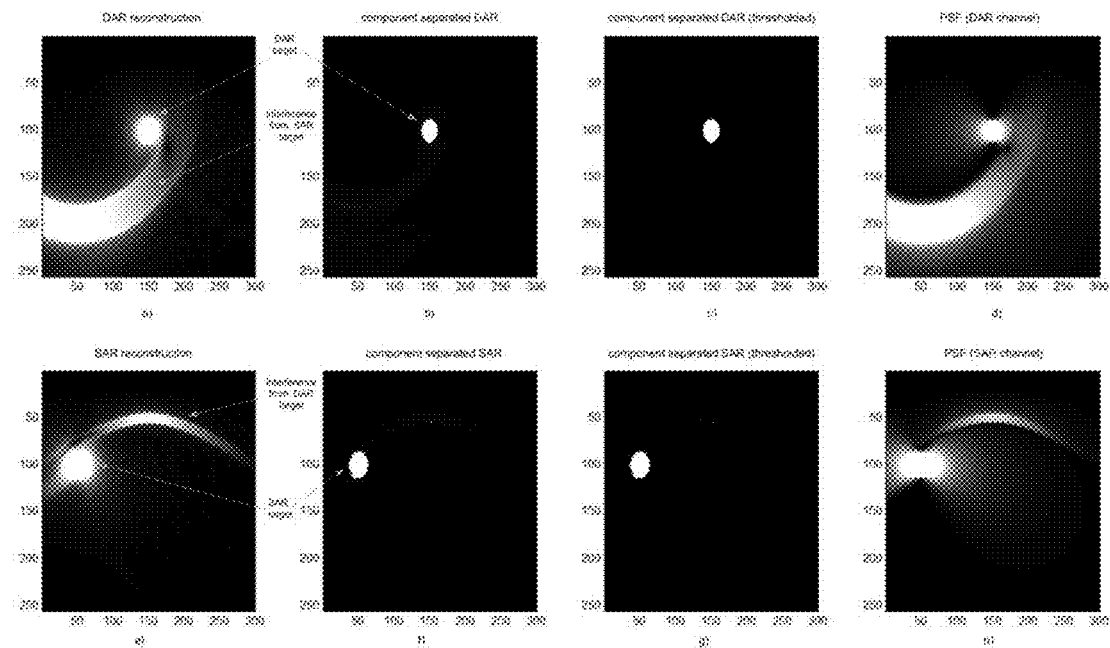
FIG. 5 is a series of images showing an example of SAR/DAR component separation applied to a digital phantom with a DAR and SAR target.
Figure 6:
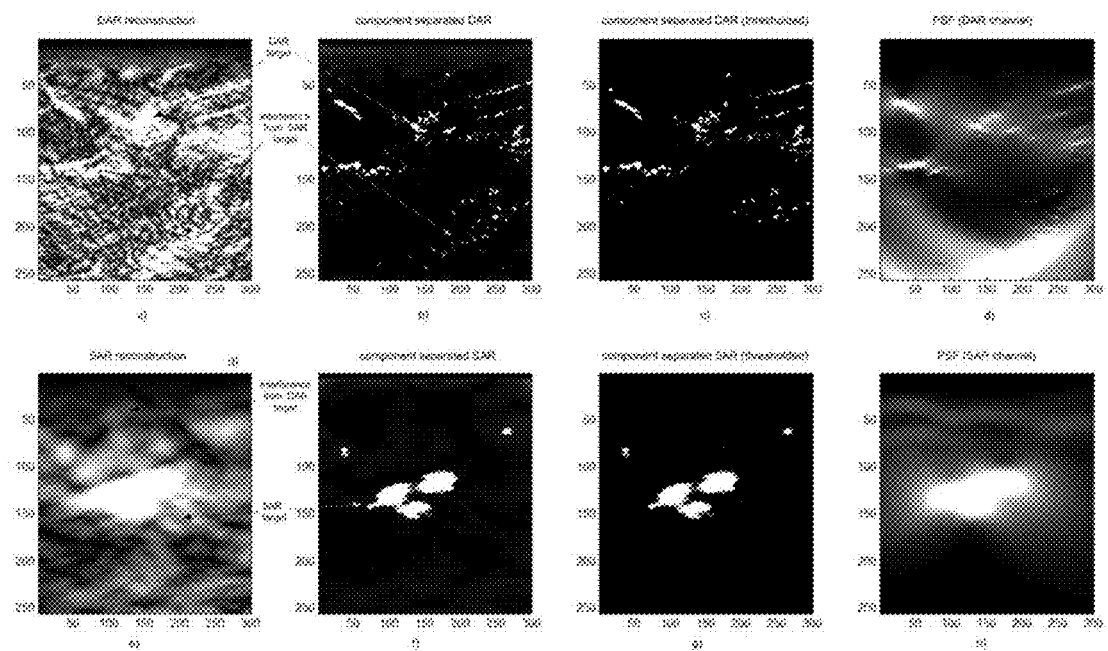
FIG. 6 is a series of images showing an example of SAR/DAR component separation applied to data from a breast lesion.

In an embodiment, the reconstruction module is capable of producing a least two separate spatial representations of a volume from a given acoustic signal. In an embodiment, the reconstruction module returns a first spatial representation based on the assumption that the given acoustic signal was produced by temporal stress confinement of electromagnetically absorbent targets in the volume (such as the electromagnetically absorbent targets discussed above) and returns a second spatial representation based on the assumption that the given acoustic signal was produced by scatter of one or more acoustic wavefronts off acoustically reflective targets within the volume (such as the acoustic wavefronts and acoustically reflective targets discussed above). Thus, the given acoustic signal can be a DAR signal or a SAR signal. A given acoustic signal may contain both DAR and SAR components and thus, the reconstruction module can be applied to generate a reconstructed DAR spatial representation and a reconstructed SAR spatial representation for the given acoustic signal. See, for example, a) and e) of FIGS. 5 and 6. Where the electromagnetic energy is light energy, the DAR signal includes portions of an opto-acoustic signal produced by temporal stress confinement, while the SAR signal can include an ultrasound backscatter signal produced by backscatter of an acoustic wavefront. In other words, where a given acoustic signal has both opto-acoustic and ultrasound components, the reconstruction module can be applied to generate a reconstructed opto-acoustic spatial representation and a reconstructed ultrasound spatial representation for the given acoustic signal. The techniques, calculations, inferences, and assumptions discussed above with respect to simulation can also be applied to reconstruction. In an embodiment, a weighted delay-and-sum technique may be applied to reconstruct the DAR and/or the SAR signals. FIG. 5 shows a series of images illustrating an example of SAR/DAR component separation applied to a digital phantom with a DAR and SAR target. FIG. 6 shows a series of images illustrating an example of SAR/DAR component separation applied to data from a breast lesion.

Simulation and Reconstruction of Acoustic Return and Probe Acoustic Backscatter

When comparing the simulation and reconstruction between DAR and SAR, it can be noted that in embodiments the wavefront may propagate from a probe interface or from the surface of the volume directly beneath or outside the probe and travel down through the tissue to reach the acoustic target that will backscatter creating probe acoustic backscatter (PAB). In the case of a theoretically ideal simple incident wavefront directed downwards into the tissue, the incident wave-front will reach a position in the tissue in direct proportion to the depth of the position based on the speed of sound. Call this position (x,y). A transducer element, located on the probe or elsewhere, may be distance r away from (x,y). The PAB from the position with reach the element after propagating distance y+r. The acoustic return from (x,y) will reach the element after only propagating distance r. In an embodiment, the SAR is substantially assumed to consist of PAB. Generally, SAR contains signals in addition to PAB.

In a delay and sum reconstruction algorithm, in an embodiment, the delays for DAR will be based on r. The delays for PAB, in an embodiment, will be based on y+r. In an embodiment, this is calculated in terms the angle theta between the surface normal and the probe element through the position. The PAB is then y+r=r(1+cos(theta)). In an embodiment, the delay can be approximated by assuming that the distance for PAB is twice the distance of the DAR. This simplification holds for small theta, and has some further applicability due to angular dependence. In an embodiment, the same reconstruction can be used for PAB and DAR, but with different speeds of sound to account for the differences in delay.

iii. Point Spread Function Module

In an embodiment, the processing subsystem comprises a point spread function (PSF) module capable of applying a model of the system to spatial representations. In an embodiment, a PSF module applies the simulation and reconstruction modules discussed above to process given first and second spatial representations of targets in a volume. In an embodiment, the first and second spatial representations are DAR and SAR spatial representations respectively. In an embodiment, the PSF module first applies the simulation module: to the first spatial representation to produce a DAR signal that might be produced by the first spatial representation; and to the second spatial representation to produce a SAR signal that might be produced by the second spatial representation.

Next, the PSF module combines the DAR and SAR signals to produce a combined acoustic signal. In an embodiment, the DAR and SAR signals may be added to produce the combined signal. In an embodiment, the DAR and SAR signals may be processed before they are combined, and/or the combined acoustic signal may be processed after the combination. Various methods for such processing including weighting and thresholding are discussed below.

Figure 7A:
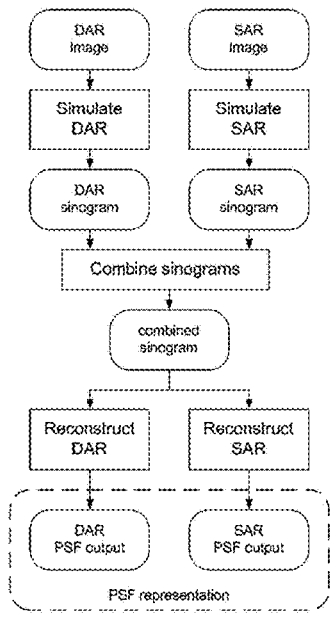
FIGS. 7A through 7C are block-level process flow charts for three alternative embodiments of aspects of a Point Spread Function (PSF) module.
Figure 7B:
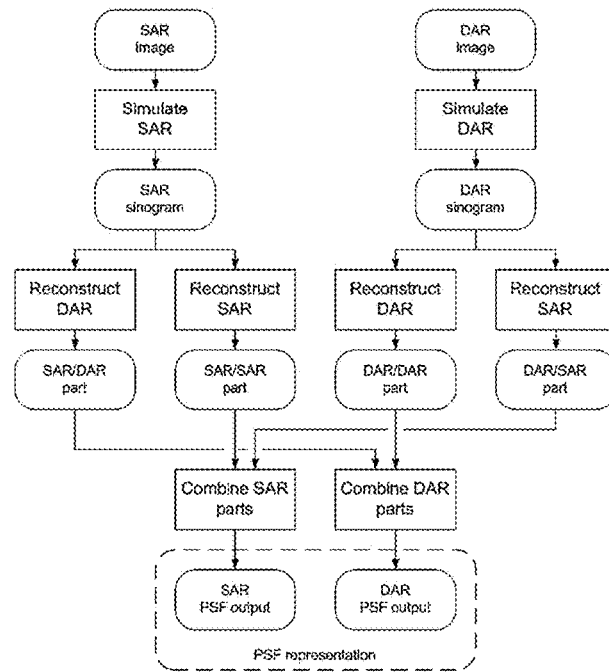
Figure 7C:
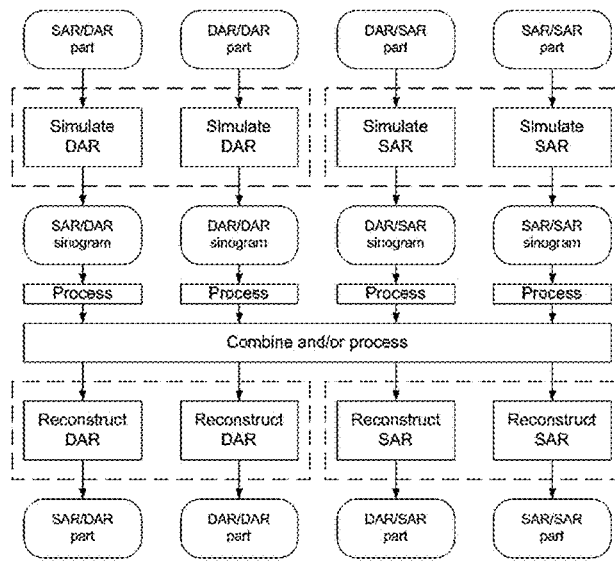

Subsequently, the reconstruction module may be applied to the combined acoustic signal to produce a PSF spatial representation of the DAR component and a separate PSF representation of the SAR component. See, for example, d) and h) of FIGS. 5 and 6. In an embodiment, the first and second spatial representations are opto-acoustic and ultrasound spatial representations, respectively. A mixing matrix can be used to describe combinations of DAR and SAR signals. In an embodiment, multiple sinograms may be collected (e.g. for multiple wavelength data), and the PSF module can use a mixing matrix to linearly combine the DAR and SAR signals. Block-level process flow charts for three alternative embodiments of aspects of the PSF module are shown in FIGS. 7A through 7C. FIG. 7A shows an exemplary DAR/SAR PSF embodiment. FIG. 7B shows an alternate DAR/SAR PSF embodiment. FIG. 7C shows an embodiment of a pathway for additional processing. In the embodiment of FIG. 7A, the DAR image is simulated with the DAR simulation module to produce a DAR sinogram, and the SAR image is simulated with the SAR simulation module to produce a SAR sinogram. The DAR sinogram is combined with the SAR sinogram to produce a combined sinogram. The combined sinogram is then reconstructed using a DAR reconstruction to reconstruct a DAR portion of the PSF output and using a SAR reconstruction to reconstruct a SAR portion of the PSF output. In the embodiment of FIG. 7B, an alternate expanded version of a PSF module is shown. In this case, separate DAR and SAR reconstructions are performed on each of the SAR and DAR sinograms and the reconstructed SAR/DAR, SAR/SAR, DAR/DAR, and DAR/SAR parts are combined in a manner to produce an appropriate PSF output representation. The embodiment of FIG. 7C is another alternate embodiment of performing PSF processing. In this case, SAR/DAR, SAR/SAR, DAR/DAR, and DAR/SAR parts are simulated to produce sinograms. Processing of each sinogram may occur and the output of the processing may include further processing and/or combining of the processed sinograms. The outputs from the combining and/or processing are reconstructed using a DAR reconstruction path and a SAR reconstruction path. The outputs correspond to SAR/DAR, SAR/SAR, DAR/DAR, and DAR/SAR parts. When SAR/DAR is merged with DAR/DAR and DAR/SAR is merged with SAR/SAR, FIG. 7C will resemble FIG. 7A. FIG. 7C indicates that each PSF output depends on at least one PSF input. In an embodiment, each PSF output is implemented by calling an optimized processing block to operate on the relevant PSF inputs.

iv. Error Calculation Module

In an embodiment, the processing subsystem comprises an error calculation module capable of measuring residual error between two sets of data in the spatial representation domain, two sets of data in the acoustic signal domain, and/or between two sets of data across mixed domains. In an embodiment, measuring residual error occurs between transformed domains. In an embodiment, a processed spatial representation is subtracted from a reference spatial representation to produce a residual error between the two representations. In an embodiment, the input to, or output of, the error calculation module may be weighted or thresholded as further discussed below. In an embodiment, error calculation may be performed in the signal domain. When error calculation is performed in the signal domain, a reference may be represented in the signal domain rather than as a spatial representation. In an embodiment, the error calculation may be performed in the signal domain from within the point spread function module after spatial representations are converted to the signal domain. In the signal domain it is easier to account for time delay offset between the current estimate and the measured data; thus, accounting for propagation time delay offset of each channel, or performing aberration correction, may be more efficient and/or more accurate in the signal domain.

v. Correction Module

In an embodiment, the processing subsystem comprises a correction module capable of adjusting a spatial representation of a given volume based on given residual error. In an embodiment, a separate residual is provided for each pixel in the spatial representation and the residuals are simply added to each pixel in the spatial representation. In an alternate embodiment, a single residual is provided for the entire spatial representation. In other embodiments, a plurality of residuals is provided and the spatial representation is adjusted by wavelets, sub-bands, or other channels. In an embodiment, the given residuals are weighted before they are added to the given spatial representation. Various methods for weighting are known in the art. In an embodiment a single constant weight is used across the entire image. In an embodiment, weights are varied based on a weights table as discussed above. In an embodiment, weights are varied by channel or sub-band. Weights can also be varied by wavelet as will be apparent to one skilled in the art. In an embodiment, weights are chosen that exceed a value required to obtain convergence on iteration, as further discussed below. Such weights may be determined by experimentation.

vi. Component Separation Module

In an embodiment, the processing subsystem also comprises a component separation module capable of applying the simulation, reconstruction, point spread function, error calculation, and/or correction modules discussed above to separate at least two components of a given acoustic signal. In an exemplary embodiment, the given acoustic signal is separated into DAR and SAR components. In an embodiment, the given acoustic signal is separated into OA and US components.

In an embodiment, the reconstruction module is applied to the given acoustic signal to produce a reference DAR spatial representation and a reference SAR spatial representation of a volume that produced the given acoustic signal. The reference spatial representations can also be used as initial values for an initial DAR spatial representation and an initial SAR spatial representation respectively. In another embodiment, the DAR and SAR spatial representations can be initialized to all zeros, threshold values, weight values as discussed above, or other specified values. The point spread function module can then be applied to the initialized DAR and SAR spatial representations to produce PSF DAR and PSF SAR spatial representations of the volume. The error calculation module can be applied to determine the residual error between the reference and the PSF DAR spatial representations. The error calculation module can be similarly applied to determine the residual error between the reference and the PSF SAR spatial representations. The correction module can then be applied to correct the initial DAR and initial SAR spatial representations based on the residuals to produce refined DAR and refined SAR spatial representations of the volume.

The component separation module can be applied to produce separate images of electromagnetically absorbent and acoustically reflective targets in the volume (such as the electromagnetically absorbent and acoustically reflective targets discussed above). See, for example, b) and f) of FIGS. 5 and 6. Better results may be obtained when thresholding is applied. See, for example, c) and g) of FIGS. 5 and 6. In another aspect of the invention, the above steps are applied to a given acoustic signal as a process with or without the provided system.

vii. Iterative Minimization Algorithms

In an embodiment, the new spatial representations further refined by iteratively applying the component separation module one or more additional times. In an embodiment, the refined DAR and refined SAR spatial representations become the initial DAR and initial SAR spatial representations for the next iteration of the process. The component separation may be iteratively applied until some condition is met. In an embodiment, the component separation module is iteratively applied a predetermined number of times. In an embodiment, the component separation module is iteratively applied until the measured residuals reach a specified limit. In an embodiment, the component separation module is iteratively applied until the PSF spatial representations converge with the reference spatial representations. In an embodiment, the effects of one or more divergent elements of the acoustic signals are removed as the modules are iteratively applied. Various methods for recognizing convergence and removing divergent effects can be used to carry out aspects of the subject invention, and will be apparent to one of skill in the art in the context presented herein. Examples of both hard and soft thresholding may be found in *A Fast Wavelet-Based Reconstruction Method for Magnetic Resonance Imaging*, by Guerquin-Kern, et. al, IEEE Transactions on Medical Imaging, Vol. 30, No. 9, September 2011, at 1649, the entire disclosure of which is incorporated herein by reference. In an embodiment, thresholding (which may be hard or soft thresholding) is applied based on the weight values discussed above and in proportion to a regularization parameter. In an embodiment, pixel values below a specified threshold are zeroed, while other values can be reduced in magnitude. In an embodiment, weights can be applied to the entire image, sub-bands, wavelets, or channels as discussed above. In an embodiment, the thresholding operation is a denoising operation, as wavelet denoising can be similar or the same as thresholding. Various denoising techniques can be used with the subject invention including, but not limited to those described in U.S. patent application Ser. No. 13/507,217, which has been incorporated herein by reference.

In an embodiment, simulation may be implemented by applying a system transfer matrix. A simple backprojection reconstruction may be represented as the Hermitian adjoint (i.e. conjugate transpose) of the system transfer matrix. Thus, when the Hermitian adjoint of the system transfer matrix is applied to measurement data from detectors (or signals in this domain) to reconstruct a volume, the result can be considered a reconstruction that maps the data domain to the solution domain. Iterative minimization may produce a result of higher quality than using a pseudo-inverse or other reconstruction method. Iterative minimization can be performed by computing a residual (e.g., difference) between a reference and a relationship of a current estimate applied to the system to modify the current estimate of the system. In this sense, the current estimate may move closer and closer towards an actual solution.

For the case of a multi-parameter model, a system transfer matrix may be formed with a block matrix approach by forming a matrix out of sub-matrices. If the model is dependent on each parameter independently, then separate system transfer matrix models may be separated out and computed independently under superposition.

The independent separation described above may not be optimal in solving the concentration of a chromophore in a multi-wavelength opto-acoustic system. In a multi-wavelength opto-acoustic system, the presence of the chromophores affects each channel (due to the wavelength specific absorption of the chromophore), and thus, the channels are not independent. In this example, the system transfer matrix is not considered (to the same degree) a reconstruction process. Often, in a reconstruction process, the goal is to use boundary measurements from a detector to literally reconstruct a spatial representation of the volume from the measurement data. If each pixel in an image is treated on substantially the same footing when a point spread function is applied, the point spread function can be considered spatially invariant (e.g. the point spread is the same for every position). This can yield a simplified model. However, the spatially variant effects (e.g. image streaking that can occur as a result of the imaging device or its measurement geometry in a reconstruction process) may be important. In exemplary circumstances, the separation of DAR from SAR (or other such components) is facilitated by the presence of these spatially variant effects, which may manifest differently for each component in an image since each component can have a different reconstruction process.

Techniques for finding concentrations of known or unknown chromophores will be apparent to one skilled in the art. In an embodiment, a Multispectral Morphological Component Analysis (MMCA) technique may be used, such as the one discussed in Bobin, et al. in *Morphological Diversity and Sparsity for Multichannel Data Restoration*, Journal of Mathematical Imaging and Vision, Vol. 33, Issue 2, pp. 149-168 (February 2009), the entire disclosure of which is incorporated herein by reference. For example, the problem can be treated as a spatially invariant image processing problem in the image domain. In this technique, one set of dictionaries represents the spectral aspect (each wavelength corresponds to a spectral observation) and another set of dictionaries represents the image aspect. In this problem, an image mixing problem as applied to hyper-spectral data can help to separate the components. Using this technique, chromophore component separation can be accomplished without modeling a reconstruction process. In the image domain, wavelets or dictionary elements that are spatially shifted copies of each other may be used for efficiency. In an embodiment, a multispectral Morphological Component Analysis (MCA) dictionary approach may also be used where dictionary symbols are projections on to a reconstruction operator. Such a multispectral MCA dictionary approach may be applied to chromophore component separation, since it is applicable to system transfer matrices. In this case, in an embodiment, separate DAR and SAR simulation, and reconstruction, could be used for efficient implementation.

Additionally, Morphological Component Analysis provides techniques for quantifying the performance of how well signals represented in different dictionaries may be separated based on the similarities between the dictionaries used. These techniques can be applied to DAR and SAR components, and may be used to quantify how well a DAR signal may be separated from a given SAR signal by looking at the similarities of their PSF functions in a given component separation technique. More generally, the technique can be applied to the novel component separation methods disclosed herein to see how well one set of components can be separated from another. In an embodiment, component separation does not solely rely on accurately modelling the resulting DAR and SAR signals from targets during simulation. For example, in an embodiment, differences in signal arrival times from the targets are used to separate signal components. In an embodiment, the component separation process also takes into account how these differences in signal arrival times influence the respective dictionaries.

Independence of Acoustic Return and an Incident Wavefront

Returning to the discussion about separating the system transfer matrix. In an embodiment, the produced incident wavefront is presumed to be responsible for all acoustic backscatter (an approximation) and the other secondary acoustic scatter (a.k.a. other acoustic scatter, acoustic reflections) that reflect from the acoustic-return sources are ignored—and as a result, the system transfer matrix from the DAR can be treated independently from the reflected acoustic backscatter (SAR). In such embodiment, separate simulation and reconstruction can be performed on the reflected acoustic backscatter from the wavefront. In an embodiment, separate simulation and reconstruction of DAR and SAR signals yields faster simulations and reconstructions, since faster algorithms may be used for simulating each of these separately.

Exemplary Pseudo Code

Pseudo code follows that can be used to implement an aspect of an embodiment of the processing subsystem.

```
vn1 = a1 = reconstruct_DAR(recorded data from transducers);
vn2 = a2 = reconstruct_SAR(recorded data from transducers);
for n = 1:NUMBER_OF_ITERATIONS
    [vn1_psf, vn2_psf] = PSF(vn1, vn2);
    r1 = a1-vn1_psf;
    r2 = a2-vn2_psf;
    tmp1 = vn1 + tau1.*r1;
    tmp2 = vn2 + tau2.*r2;
    wn1B = threshold(tmp1, lambda, tau1);
    wn2B = threshold(tmp2, lambda, tau2);
    tnB = (1+sqrt(1+4*tn^2))/2;
    vn1B = wn1B+(tn-1)./tnB*(wn1B-wn1);
    vn2B = wn2B+(tn-1)./tnB*(wn2B-wn2);
    wn1 = wn1B;
    vn1 = vn1B;
    wn2 = wn2B;
    vn2 = vn2B;
    tn = tnB;
end
function [x1_psf, x2_psf] = PSF(x1,x2)
    sinogram_tmp = simulate(x1, x2);
    [x1_psf, x2_psf] = reconstruct(sinogram_tmp);
end
function sinogram_combined = simulate(x1, x2)
    sinogram_combined = simulate_DAR(x1) + simulate_SAR(x2);
end
function [x1_out, x2_out] = reconstruct(sinogram_tmp)
    x1_out = reconstruct_DAR(sinogram_tmp);
    x2_out = reconstruct_SAR(sinogram_tmp);
end
```

Figure 8:
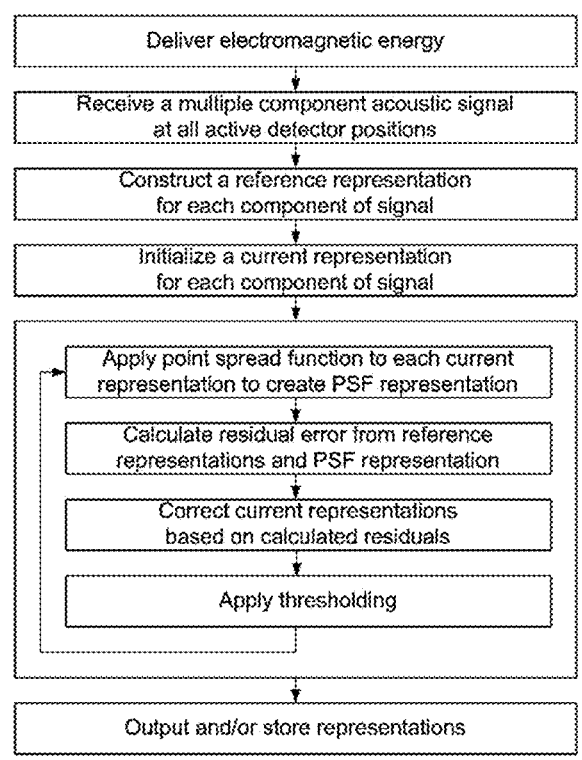
FIG. 8 is a flow diagram illustrating a process flow for SAR/DAR component separation in accordance with an embodiment.

In this example, a1 and a2 are arrays (e.g., two or more dimensional arrays) holding DAR and SAR images reconstructed from the recorded acoustic signal. In the above embodiment, a1 and a2 are used as the reference images. The variables vn1 and vn2 are arrays for holding the current reconstructed DAR and SAR spatial representations respectively. The variables r1 and r2 hold pixel by pixel arrays of residuals. In other embodiments, a single residual can be calculated for the entire image or residuals can be calculated by wavelets, sub-bands, or other channels as discussed above. Here, the variables tau1 and tau2 are pixel by pixel weights that are applied to the residuals. In other embodiments, weights can be applied by wavelets, sub-bands, or other channels as discussed above. In an embodiment, the weights applied are based on the weights table discussed above. In the pseudo-code embodiment, thresholding is applied to the current DAR and SAR images based on tau1 and tau2 in proportion to the regularization parameter (lambda). In an embodiment, the a1 and a2 reference images are produced using a more complex reconstruction algorithm than that performed by the PSF function during iteration. This embodiment, allows the reference images to start off with a higher quality, while maintaining speed for the subsequent iterative processing. For example, in an embodiment, adaptive beamforming is used to reconstruct the a1 and a2 reference images. FIG. 8 shows a process flow in an illustrative embodiment for SAR/DAR component separation.

In accordance with the embodiment of FIG. 8, electromagnetic energy is first delivered to the tissue or other area of interest. A multiple-component acoustic signal is then received as all active detector positions. Then, a reference representation is constructed for each component of the signal. A current representation is then initialized for each component of the signal. An iterative PSF process is then applied as follows. A PSF function is applied to each current representation to create a PSF representation. Residual error is calculated from reference representations and the PSF representation. Current representations are then corrected based on calculated residuals. Thresholding is then applied, and the iterative process returns to the step of applying a point spread function above. After the iterative PSF process, the representations are output and/or stored.

Iteration, Weighting, Thresholding

Various iterative thresholding techniques are known in the art and can be applied to the subject invention including, but not limited to, hard thresholding, soft thresholding, FISTA (Fast Iterative Soft Thresholding), FWISTA (Fast Weighted Iterative Soft Thresholding), Morphological Component Analysis (MCA), Multispectral Morphological Component Analysis (MMCA). In an embodiment, values below a threshold are zeroed while other values remain the same or are reduced in magnitude. The weighting step can be optional. Alternately, if each pixel is not individually weighted, a constant value that corresponds to the maximum divergent value of tau1 and tau2 can be used. As described herein, and known in the art, sparse representation in transform domains or sparse dictionaries can be used to improve performance. Accordingly, some illustrative embodiments for using sparse representations in component separation are shown in FIGS. 9A through 9D. FIGS. 9A through 9D illustrate embodiments for applying dictionary transformations in component separation.

In accordance with the embodiment of FIG. 9A, a reference representation is first constructed for each component of a signal for each frame. Then, a current representation is initialized for each component of the signal for each frame. An iterative PSF process is then applied as follows. A PSF function is applied to each current representation to create a PSF representation. Residual error is calculated from reference representations and the PSF representation. Current representations are then corrected based on calculated residuals. Thresholding is then applied, and the iterative process returns to the step of applying a point spread function above.

In accordance with the embodiment of FIG. 9B, a reference representation is first constructed for each component of a signal for each frame. Then, a current representation is initialized for each component of the signal for each frame. A dictionary transformation is then applied to each current representation and/or reference representation. Then, an iterative process begins by applying a point spread function to each current representation to create a PSF representation. In an embodiment, this involves applying inverse dictionary transformation to each current representation, applying a point spread function, and applying the dictionary transformation to each current representation. The iterative process then proceeds to calculate residual error from reference representations and the PSF representation. The current representations are corrected based on the calculated residu-als. Thresholding is then applied, and the iterative process returns to the step of applying a point spread function above.

In accordance with the embodiment of FIG. 9C, a reference representation is first constructed for each component of a signal for each frame. Then, a current representation is initialized for each component of the signal for each frame. Independent sub-band dictionary transformation is then applied to each current representation and/or each reference representation to create sub-band representations. An iterative process then begins by applying a sub-band point spread function to each current sub-band representation to create a PSF sub-band representation. The residual error is then calculated from sub-band reference representations and the PSF sub-band representation. The current sub-band representations are then corrected based on calculated residuals. Thresholding is applied, and the iterative process returns to the step of applying the sub-band point spread function above. After the iterative process, inverse sub-band dictionary transformation is applied to independent sub-bands and the overall result is output.

In accordance with the embodiment of FIG. 9D, a reference representation is first constructed for each component of a signal for each frame. Then, a current representation is initialized for each component of the signal for each frame. A dictionary transformation is then applied to each current representation and/or reference representation. Then, an iterative process begins by applying a point spread function to each current representation to create a PSF representation. The iterative process then proceeds to calculate residual error from reference representations and the PSF representation. The current representations are corrected based on the calculated residuals. Dictionary transformation is applied to each current representation. Thresholding is applied, an inverse dictionary transformation is applied to each current representation, and the iterative process returns to the step of applying a point spread function above.

Thus, in an embodiment, a system comprises: a) an energy source configured to be deliver electromagnetic energy to a volume of tissue; b) a probe configured with features to produce at least one acoustic wavefront directed to propagate into the volume originating at the interface of the probe and the surface of the volume as a direct or indirect result of absorption of the electromagnetic energy by portions of the volume, probe, or interface; c) a transducer array for recording acoustic signals resulting from: i) DAR from electromagnetically absorbent targets within the volume; and ii) SAR from sources of acoustically reflective targets that backscatter (i.e. reflect) from the acoustic wavefront; d) a processing subsystem, comprising: i) a module for simulating acoustic signals that may be produced on delivering the electromagnetic energy to the volume, comprising: 1) a sub-module for simulating DAR signals from the electromagnetically absorbent targets within the volume; 2) a sub-module for simulating SAR signals from the acoustically reflective targets in the volume; ii) a module for reconstructing acoustic signals to produce spatial representations representing the volume, comprising: 1) a sub-module for reconstructing the electromagnetically absorbent targets in the volume; 2) a sub-module for reconstructing acoustically reflective targets in the volume; iii) a module for component separation, comprising: 1) a sub-module for computing a residual between a simulated estimate of the electromagnetically absorbent targets within the volume and a reference based on the recorded DAR signals; 2) a sub-module for computing a residual between a simulated estimate of acoustically reflective targets in the volume based on the recorded SAR signals; 3) a sub-module for modifying the estimates of the targets based on the residuals; 4) a sub-module for outputting final estimates of the spatial representations of (or acoustic signals produced by) the targets.

In an embodiment, the module for component separation is configured to execute a process for component separation, comprising the steps of: a) producing reference representations for DAR and SAR by reconstructing the recorded acoustic return signals; b) computing at least one iteration comprising the steps of: i) applying a point spread function to the current estimates of DAR and SAR by the steps of: 1) simulating the current DAR estimate to produce a DAR sinogram; 2) simulating the current SAR estimate to produce a SAR sinogram; 3) adding DAR sinogram to the SAR sinogram to produce an overall sinogram; 4) reconstructing the DAR from the overall sinogram to produce a DAR PSF representation; 5) reconstructing the SAR from overall sinogram to produce a SAR PSF representation; ii) computing the residuals between the reference and psf representations; iii) multiplying the residuals by a weight to give the weighted residuals; iv) adding the weighted residuals to the current estimates of DAR and SAR; and v) applying thresholding to produce the next estimates of DAR and SAR.

d. Measuring and Processing with the Upward Directed Skin Response

In an embodiment, the volume comprises layered skin tissue and the different skin layers have different optical absorption and/or produce wavefronts of different intensities. The skin layers and properties can vary from subject to subject. The DAR from the skin and coupling layers are amongst the first signals to reach the transducers. Wavefront from the skin layer absorption travel downward into the tissue as well as upward to the transducer. To visualize this phenomenon, consider a point source in a volume that emits a spherical ripple where part of the ripple wavefront moves towards the detector and the opposite part moves away from the detector. Similarly, a planar shaped source will have an upward moving component that reaches a detector and a downward moving component that does not. Hence, the downward wavefront from the skin layer may produce a reflected SAR response from the volume that will correlate with the upward wavefront produced by the skin layer. In an embodiment, the upward moving component is an upward directed response, and the downward moving component is a downward directed response. The wavefront intensities produced by the skin layers are a function dependent on depth. In an embodiment, this can be presented by a 1D function. In an embodiment, the DAR of the skin layers may be detected an analyzed, and used to deconvolve, detect or separate the corresponding SAR signals with methods described herein. For example, if the skin has three layers, three planar shaped wavefronts may propagate upward to the transducers as DAR signals and also downward into the tissue and then reflect back to the transducers as SAR signal. In an embodiment, the skin DAR is first analyzed and may be used directly or may otherwise be used to produce an auxiliary signal that will be expected to characterize the reflections and then used to process or separate the SAR signals. In an embodiment, a 1D skin function is determined by averaging skin signals from each channel, and/or by determining their most prominent component. In an embodiment, the skin function may be determined by extracting this information from a reconstructed image rather than from a sinogram. Hence, in an embodiment, information about the downward propagating wavefront can be inferred or measured from the upward propagating waves, and then used to analyze backscatter of the downward propagating wavefront. In an embodiment, the skin DAR or auxiliary signal is used to form a transfer function, and the transfer function is applied as filtering in the simulation and/or reconstruction modules.

e. Simulation of Probe Features

In an embodiment, a cause of all or part of the SAR signal component can be modeled and the model used to separate such component from the DAR. In an embodiment, a wavefront is caused by a feature or element on or in a probe that delivers electromagnetic energy. A pattern or code can be simulated by treating each feature or element as an independent source (i.e. treating source wavefront elements of a complicated wavefront geometry separately). The backscatter pattern from a point source is easy to model in an ideal case. Any source can be built out of multiple point sources. A line source, cylindrical source, or finite length line or cylindrical source can also be modelled. These sources can propagate due to acoustic mismatch of the probe with the volumetric illuminated background initial pressure source, which is described further below. Also, these sources could occur directly due to initial pressure due to electromagnetic absorption. Wavefront producing features of a probe may make the wavefront, which is substantially unpredictable due to subject variability, more predictable, or may permit the acoustic backscatter from a target to be easier to pinpoint. In an embodiment, features may cause stronger acoustic backscatter. In an embodiment, the produced acoustic backscatter has better convergence when starting with initial conditions in an iterative component separation method.

In an embodiment, only the significant features or elements need be modeled. In other embodiments, complex scenarios are modeled. For example, the surface of the volume and the probe can be represented by a 3D source producing matrix. In an embodiment, each source is broken down (if necessary) into point source elements. In an embodiment, for simplicity spherical wave point sources are used. In an embodiment, the mathematical technique known as Green's function solutions can be used. In an embodiment, a directionality apodization can be applied. In an embodiment, the dot product with a normal is efficient as a directional apodization. In an embodiment, the source strength can be efficiently multiplied as a function of distance. In an embodiment, the source acts on a target as a delta function based on the distance away from the target, and the time elapsed. In an embodiment, the temporal signal received from a target is modeled as the delta function times a magnitude applied to a convolution kernel. In an embodiment, the convolution kernel for an optically absorbing target (simple) is different from a convolution kernel used from a target produced by a mismatched surface reflection due to volumetric illumination (not as simple unless using an approximation). In an embodiment, homogenous speed of sound is modeled in tissue.

In an embodiment, spherical wave point sources are used for simplicity and the signal's intensity is attenuated as a function of distance travelled based on a Green's function solution. Also for illustrative purposes, in an embodiment, a sparse 64×32×8 matrix of sources is used to model the wavefront resulting from the probe. The aspect ratio of the voxels can be substantially equal, so the voxels are cubic voxels, or each voxel represents a point source. Dimensions of the probe face for this example are 40 mm×20 mm×0.5 mm. In this example, the air surface outside of the probe is not modeled using this matrix, but this can be modeled by adding an overall ideal plane wave convolved with a kernel that is a function of depth, or for simplicity a constant kernel.

All of the voxels where z=1 in the probe to can be set to 1.0. For voxels beneath the optical window, these voxels where z=1 can be set to 2.0 and where z=32 to −10.0 (to simulate a 3D coded feature). A random coded pattern can be placed on the surface of the probe to correspond to random small beads located on the probe at the grid sites determined to randomly contain a bead. Thus, in a constructed probe, which grid sites should contain a bead may be randomly determined, and in the event that a bead is present, a bead will be placed on the probe in the corresponding spot. For illustrative purposes, the bead will be a strong source, so when a bead is present, the value of 20.0 is added to the 3D matrix where z=1. For this example, in an embodiment, 40 beads are placed at random positions on the grid of the probe face, but not on top of positions corresponding to the glass window and not on top of regions near transducers. There will be an ideal acoustical isolator surrounding the detector elements that does not reflect acoustic signal. The embodiment will also include a source of value 5.0 to correspond with the position of isolator at z=1. If incident wavefront produced by this 3D matrix of sources is simulated, each point in the tissue will receive a different time domain wavefront signal. The strongest features from the matrix will be received by the point in the tissue. For the moment, angular dependence is ignored. The SAR signal will be based on acoustic reflections of the wavefronts as sent to the tissue by the probe, according to the time domain wavefront signal, which in general will be different at each position in the tissue, especially for points that are not nearby each other. Points that are close by may experience a similar time domain wavefront. In an embodiment, the time domain signal for each point will be a summation of each source intensity in the 3D matrix, occurring at a time related to the propagation delay from the matrix position to the point, and a weighting of the source in proportion to the propagation delay and as a function of the angle. By examining the time signals seen at a point in tissue due to just the beads, and ignoring magnitude of the intensities, then the time signal from the beads will consist of an impulse corresponding to each bead based on the propagation delay to the position and the bead.

Since attenuation of this received signal will be a decreasing function of distance, in an embodiment, the magnitude of the impulses based on a simple decreasing function of distance in the time domain can be modeled. If the situation is highly non-ideal, then in an embodiment, the results will be approximate, causing errors in the time domain signal, thus sacrificing resolution. In an embodiment, the wavefront from acoustic mismatch due to volumetric illumination can be modeled as a non-stationary convolution with depth, or an approximation of a stationary convolution can be used. In an embodiment, edges or line sources can be modeled as point sources convolved with a suitable waveform, and added under superposition. In an embodiment, each point in the tissue has a one-dimensional filter corresponding to the coded impulse response in the time domain. In an embodiment the filter has a corresponding wiener deconvolution filter. In an embodiment, as a simplification, the filter for each point in the tissue can be common for all detectors. In an embodiment, if a code pattern is only a function of one spatial parameter, such as depth, there can be a common filter for all points of equal depth. In an embodiment, the features can produce a code pattern that is approximately separable in more than one spatial coordinate, and the filter can be a composition of this separability.

In an embodiment, a backscattered signal from a volume is spatially coded by embedding features or elements on the probe (or other system component) to independently modulate each spatial position of the tissue with a foreknown time domain waveform, resulting in a superposition of backscatter caused by each element or feature. When the acoustic signal from all receivers is measured, and beamformed to a particular spatial position (by applying delays) the time-domain beamformed signal will (instead of being a delta function from the backscatter) be modulated according to the acoustic reflections caused by the features on the probe. Since it is known in advance what code or response has made its way to each position, the resulting time domain signal can be correlated with the known code or response that had reached a position. Deconvolution can be used to determine the signal arising from the code or response. Hence, deconvolution that makes use of the features on the probe that cause this effect can be compensated advantageously. Stated another way, DAR signals will not be correlated with patterns from the probe features, but PAB signals will be correlated with the pattern of probe features. Hence, correlating wavefront backscatter with waveforms based on wavefront producing features of the probe permits separation of the DAR signal from the PAB signal. It also helps identify reflective targets for unpredictable wavefronts resulting from subject variability, since predictable wavefronts are used to mark the reflective targets with a predictable signature.

In an embodiment, a wavefront of a distinctive nature propagating into the tissue can be used. Such a wavefront may be appropriate even where a similar code waveform will reach all positions in the tissue. Computationally, it may be easier to separate DAR signals from wavefront PAB signals if all wavefront backscatter sources are modulated with a similar code. In an embodiment, the edges of the probe from the air-tissue-skin boundaries can serve as features that may be used to distinguish between DAR and SAR, and thus helpful to separate at least one of them. The code waveform may change slowly as a function of depth. In an embodiment, an optical exit port of the probe may produce wavefronts that may be used to aid in distinguishing between DAR and SAR signals, and thus helpful to separate at least one of them. In an embodiment, other features of the probe surface may produce wavefronts that may be useful to separate DAR from SAR signals.

When the DAR signal and SAR signal are highly correlated, they may be difficult to distinguish and thus, to separate. By identifying features of the probe that cause a known incident wavefront, differences between the return signal and backscatter signal information can be more easily identified. Similarly, by using features of the probe to control the incident wavefront, the correlation between the return signal and backscatter signal information can be reduced, leading to an improvement in component separation and/or SNR.

In an embodiment, known wavefront sources external to the volume may be simulated to determine wavefronts that will propagate into the volume. In an embodiment, wavefront sources that arise from targets within the volume (e.g., vessels) may be simulated to determine wavefronts that propagate within the volume. In an embodiment, a map may be created to represent the temporal impulse response waveforms reaching different locations of the volume due to wavefronts from optically absorbing sources within and/or external to the volume. In an embodiment, a DAR spatial representation may be used to represent optically absorbing sources external to, or within the volume. In an embodiment, initial pressure sources may be used to determine maps of waves in the volume at numerous time-steps. In an embodiment, spatially dependent temporal impulse responses may be extracted from maps of waves in the volume at numerous time-steps because the temporal impulse response is related to the pressure waves arriving at a position as a function of time. In an embodiment, the simulation of SAR may apply temporal impulse responses to corresponding (e.g. proximate) acoustically reflective targets when totaling the contribution of these targets to the sinogram. An omnidirectional assumption may be used in such totaling, and/or during wavefront simulation.

In an embodiment, the acoustic waveform from an absorbing 1D spatial pattern (i.e. a line) on the surface of the probe that reaches a target in the volume will vary as a function of position. Consider a 1D absorbing pattern defined by the function f(r) placed on the surface of the probe along the line defined by: (r*cos(theta), r*sin(theta), 0). Assuming a homogeneous medium with sound speed c, then at time t, the portion of the acoustic wave that reaches position (px, py, pz) in the volume will correspond to f(px*cos(theta)+py*sin(theta)+sqrt((px^2−py^2)*cos(theta)^2+2*cos(theta)*px*py*sin(theta)−pz^2−px^2+02*c^2)). That is to say, that the portion of the 1D pattern responsible for the acoustic waveform reaching the position will be temporally distorted by constants C1, C2 and C2 as f(C1+sqrt(t^2*c^2−C3)) that change with regard to position in the volume and orientation of the line. Hence, in an embodiment, the 1D pattern can be used to spatially encode the volume according to the known constants. In an embodiment, the pattern on the line can be broken down into point sources and the solution for the acoustic waveform reaching positions in the volume can be determined using Green's function methods. In an embodiment, multiple 1D line patterns can be used in superposition (e.g. an "X" shape). In an embodiment, when an absorbing 2D pattern on the surface of the probe produces an initial pressure distribution, frequency domain methods can be used efficiently for solving the acoustic waveform reaching positions in the volume. In an embodiment, to compute the waveforms in the volume from a 2D surface pattern, existing methods for computing signals reaching 2D planar detectors from a 3D volume can be adapted by using temporal reversal with a Dirac impulse applied to the time domain input corresponding to the illumination. In an embodiment, a simplification of this adaptation yields a fast solution for signals in an imaging plane.

In an embodiment, when the known produced waveforms at positions in the volume, as described above, are sufficiently unique at different positions in the volume, the backscatter from each of the different positions that will be recorded by the transducers can be said to contain a signature sufficiently unique to encode the different positions in the volume. In an embodiment, fronts of the produced wavefronts reach targeted positions in the volume. In an embodiment, the fronts that are seen by targets at the targeted positions are known (i.e. substantially deterministic) produced time-domain waveforms. Thus, in an embodiment, backscatter received from a position in the volume will, in a manner, be modulated with a spatially varying code. For example, in a situation where two positions are equidistant from a transducer element, a different spatially varying code would correspond to each position. The backscatter signal received by the transducer element from the first position would interfere with the signal received by the transducer element from the second position. However, in an embodiment, the intensity of a signal component corresponding to the first code and the intensity of a signal component corresponding to the second code can both be computed as a way to quantify the intensity of backscatter at each position, thereby discriminating between the two interfering components of the signal. In an embodiment, in a dense volume the intensity of signal components corresponding to each position can be computed. In an embodiment, multiple transducer elements are used. In an embodiment, an iterative method (e.g. an iterative separation method) is used to determine the backscatter intensity from multiple interfering positions in a volume. In an embodiment, spatially varying wavefronts encoding a volume are used to discriminate between signal components received from sources equidistant to a single transducer element. In an embodiment, spatially varying wavefronts encoding a volume are used to discriminate between signal components received from sources at varying elevational angles when the sources are equidistant to an axis of a 1D transducer array. In an embodiment, the volume is considered a linear system, and frequency content of incident acoustic wavefronts penetrating the volume will produce acoustic backscatter components with substantially the same frequency components as the incident wavefronts. In an embodiment, incident acoustic wavefronts with controlled frequency contents can be directed into the volume and used to identify the acoustic backscatter component.

Opto-Acoustic Isolators

In an embodiment, the probe incorporates an isolator that reduces the amount of energy received by one or more acoustic receivers. In an exemplary embodiment, the isolator is an opto-acoustic isolator that reduces the amount of energy transmitted from a light path of the probe to a transducer assembly, which is also positioned on or near the probe. Such an isolator is described in U.S. patent application Ser. No. 13/746,905, which is incorporated by reference herein. In an embodiment, the isolator substantially reduces one or more artifacts in images reconstructed from acoustic signals received by the probe. In an embodiment, the isolator absorbs acoustic waves. It may be fabricated, for example, from a material with a high acoustic attenuation coefficient across a broad range of frequencies. In an embodiment, the isolator does not reflect acoustic waves originating from the volume back into the volume. In an embodiment, the isolator produces a wavefront that will reflect off of acoustically reflective targets in the volume as a SAR signal. The isolator can be located for producing wavefronts at a suitable position on the probe surface or other system component. In an embodiment, an isolator on the surface of the probe may be coated partially or fully with an optically reflective coating. In an embodiment, when the isolator is coated with an optically reflective material, a wavefront from optical absorption is not produced or is substantially reduced. In an embodiment, the isolator may be colored with an optically absorbing coloring, which may reduce optical energy penetrating the probe. In an embodiment, the isolator may be colored with an optically reflective coloring, which may reduce optical energy penetrating the probe. In an embodiment, when the isolator is colored with an optically reflective coloring, a wavefront is not produced from optical absorption or it is substantially reduced. In an embodiment, the isolator and surrounding portions of the probe surface may be covered with a pattern. In an embodiment, horizontal or vertical features cover the isolator, such as bars, lines or a rectangle on the distal surface of the probe. In an embodiment, when such features lie parallel to an array of acoustic receivers, stripe filtering may be applied to a sinogram to reduce any interference caused by such features. In an embodiment, the light reflective coating is gold or gold paint, a metal or metallic paint, or other such suitable coating. In an embodiment, the wavefront producing feature is an uncoated isolator. In an embodiment, a perylene coating is used in the isolator. In an embodiment, a spacer is used in lieu of an isolator. FIG. 16 shows examples of codes that can be formed on an isolator, a probe surface, or on the surface of another system component. In an embodiment, the isolator can reduce SAR and/or PAB artifacts in images reconstructed from received acoustic signals. The isolator or other components (e.g., a spacer, a probe and an optical window) can be modified in accordance with the present disclosure to control the wavefronts produced by optical absorption and/or acoustic reflection, such as, for example, to increase the intensity of the wavefronts, decrease the intensity of the wavefronts, or make patterned wavefronts. In an embodiment, the optical absorption of an isolator alters the fluence distribution in the imaging plane, which may also reduce near field artifacts. Optical absorption occurring on the surface of the isolator can reduce the light delivered to the near field directly beneath the transducer assembly, which can reduce first order ringing and reduce downward directed wavefronts impacting the imaging plane below the transducer assembly that occurs due to the mismatch between the volume and the transducer assembly and due to the high skin absorption. Hence, it is believed that having an isolator with high optical absorption may transfer the energy of downward directed wavefronts and artifacts associated with high near field illumination from the imaging plane to wavefronts originating adjacent to (away from) the imaging plane, which improve visibility in the near and mid fields. In an embodiment, the exposed isolator surface forms a rectangular shape with an interior rectangular shape for the transducer array, such that the boundary can be grouped into four bar shaped feature segments. In an embodiment, enhanced coating of the isolator should further reduce artifacts. In an embodiment, exposing two bars of the isolator instead of the full rectangle (e.g., by coating all or a portion of the other two sides of the rectangle with a reflective surface (e.g., gold)) may reduce artifacts (see simulation below). In an embodiment, the other methods described herein may further reduce artifacts by separating signal components that occur as a result of this effect.

Figure 10A:
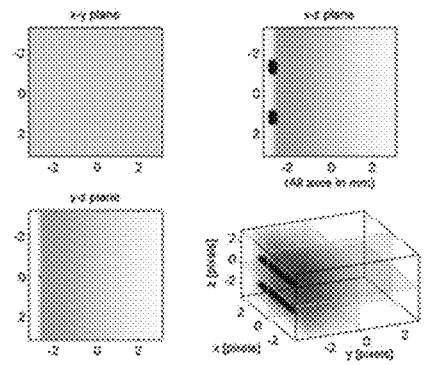
FIGS. 10A through 10C are animated frames illustrating acoustic waves in a simulated volume caused by two electromagnetically absorbent bars on a probe.
Figure 10B:
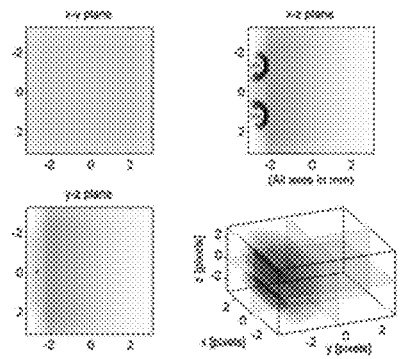
Figure 10C:
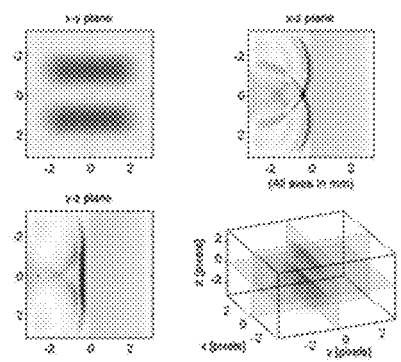

FIGS. 10A through 10C show frames of an animation of acoustic waves in a simulated volume caused by two electromagnetically absorbent bars on the probe. Three different timeframes are simulated, as follows. In FIG. 10A, the system is at initial pressure when the electromagnetic energy is delivered. In FIG. 10B, the same system is shown a moment later. In FIG. 10C, the same system another moment later. In each figure, the background tissue is illuminated. These figures are just for illustrative purposes; the simulation used to create this animation is not suitable for real-time image processing.

Sparseness in the Component Domain

In an embodiment, the reconstructions for DAR and SAR will tend to be more sparse in the appropriately reconstructed domain. For example, a SAR signal from an acoustically reflective target will have a tendency to be represented more sparsely in the SAR reconstructed image domain than in the DAR reconstructed image domain. Correspondingly, a DAR signal from an electromagnetically absorbent target will tend to be represented more sparsely in the DAR reconstructed image domain than in the SAR reconstructed image domain. In a DAR reconstructed image, an acoustically reflective target will be smeared. See, for example, the DAR reconstructed images in FIGS. 5A and 6A. In an SAR reconstructed image, an electromagnetically absorbent target will be smeared. See, for example, the SAR reconstructed images in FIGS. 5E and 6E. This sparsity allows the processing system to effectively separate the signal. In the sinogram domain, a point target is not localized to a point, thus it is not represented localized in the sinogram; rather a point target is represented as a curve in the sinogram. Thus, in a preferred embodiment, the sparsity of the reconstructed image domain is used as a minimization constraint. As targets tend to be contiguous, they will also be sparse in other domains. Thus, in an embodiment, maximum sparseness can be obtained in the appropriately reconstructed image domain for the component that further transformed into an additional sparse basis.

Using SAR to Indicate Regions of Tissue

In an embodiment, weakly scattering tissue will permit an incident wavefront to travel, while strongly reflecting tissue, such as e.g., lung tissue, will reflect substantially an entire incident wavefront. In an embodiment, using the teachings disclosed herein, detection of a reflected wavefront from lung or similar tissue and separation of this SAR signal from DAR is performed. In an embodiment, the SAR signal from lung or other such tissue can be detected, and used to mark or delineate the position of this tissue in an image. In such case, signals from depths beneath the lung tissue can be lessened or removed from an OA image. For example, lung tissue causes a strong reflection (as shown in FIG. 2). Even in cases when the component separation is not perfect, the detection of a strong separated signal or with strong characteristics can signify that the portions of the DAR image (e.g., beneath the delineated SAR target) should be completely weakened or deleted, even though the SAR signal has not been completely separated. For example, in FIG. 2, reconstruction of the SAR component (not shown) may yield a contour of high intensity that lines-up with the strongly reflecting boundary in the ultrasound image. In an embodiment, the SAR signal is used to detect or segment regions of the DAR signal or DAR image that should be mitigated, not displayed, or displayed separately. In an embodiment, a user can indicate (by drawing a line, moving an indicator, or other input) a non-imaging region or depth containing lung, bone, muscle, or other interfering tissue. In an embodiment, this indication is used to mitigate an unwanted signal. In an embodiment, this indication is used in combination with component separation to mitigate the unwanted signal. In an embodiment, the presence of a strong reflection from the separated SAR signal is used to automatically segment, characterize, or delineate unwanted regions of the image. For example, in breast imaging, lung tissue may have a strong reflection, that would otherwise not be present, and would be much stronger than in other breast tissue, hence the SAR signal or SAR image can be used to indicate the boundary of this region (even when the component separation is not completely effective and even where only a first pass reconstruction for the SAR image has been computed). In an embodiment, segmentation is performed on the SAR image to determine where the regions of tissue, if present, are located; following this, unwanted regions of the image (e.g., the lung tissue), if detected, may be removed from the image or from a sinogram. In an embodiment, an algorithm to perform the mitigation is provided comprising: i) when the overall SAR component in the SAR image matches a prescribed criteria then, ii) for each pixel coordinate along the horizontal axis, iii) find the shallowest vertical depth pixel in the SAR image that has intensity beyond a given level; iv) next, if such a pixel was found, then zero out all pixels in the DAR image at the current horizontal coordinate from substantially the found vertical depth and deeper; v) repeat from step iii) for the next horizontal coordinate. In an embodiment, the prescribed criteria may include the presence of a strong SAR ridge segment in the SAR image, such as a ridge that may be present from lung or rib tissue. In an embodiment, the criteria may include where the normalized overall intensity of the SAR image is greater than a prescribed level.

Out-of-Plane Structures

In an embodiment, out-of-plane structures can be detected and identified with the coded waveform. In an embodiment, the probe may produce an incident wavefront designed to differentiate backscatter in from objects passing through imaging plane from out of plane objects. In an embodiment, iterative minimization is used to reconstruct a 3D spatial representation of a volume using sinogram measurements with a 1D transducer array, which can determine out of plane structures as described above.

Vessel Detection

In an embodiment, optically absorbing targets that are strongest and/or conform to a specific shape profile in a reconstructed image may be assumed as vessels. In an embodiment, assumed vessels are automatically detected. In an embodiment, vessel detection involves finding regions of an image containing a shape profile, e.g. by correlating with a shape profile filter. In an embodiment, a shape profile filter may detect ridges, hyperbolas, arcs, curves, blobs, lines or other such shapes. The shape profile of a vessel and/or cylindrical object may depend on its position relative to the probe and on its orientation (e.g. polar and azimuth angles) when crossing the imaging plane. The depth of a target represented in an image is related to its distance from the probe. Commonly, a vessel crossing the imaging plane will be at a closest distance to the probe where it intersects the imaging plane. When an illustrative marker touching a vessel is moved away from the imaging plane, the distance of the marker to the probe may increase. Consequentially, portions of a straight vessel may appear to bend deeper in an image as portions of the vessel extend away from the imaging plane. Accordingly, characteristic streaks may be observed from vessels in an image. Since this bending or streaking depends on the position and orientation of the vessel, in an embodiment, orientation and/or position may be extracted (i.e., deduced) from an image or data that captures a vessel or other such object. In an embodiment, the crossing of an object through the imaging plane is represented by template curves for different positions and orientations. In an embodiment, the data and/or image representation of a target object is matched to the template curves to determine orientation and/or position. In an embodiment, the template curves may follow an equation, be extracted from simulation, or obtained otherwise to describe how an oriented object is expected to appear. In an embodiment, a polar angle, and azimuth angle and/or a position of the object with respect to a co-ordinate reference (or other such angular representation) is output. In an embodiment, the position is used as an input and the orientation is an output. In an embodiment, the path of the vessel or object is traced in the image or sinogram, and the traced path is best fit onto a curve (e.g. that represents a parametric equation describing orientation and/or position) such that the best fit solution yields the sought orientation and/or position.

In an embodiment, the volume is spatially represented by coefficients in a dictionary, basis or frame of steerable wavelets. Steerable wavelets allow, for example, ridge elements or steered ridge detection filters to be represented by a small number of independent coefficients whereby the steering orientation can be efficiently extracted from the coefficients. In an embodiment, when a volume is represented by steerable coefficients, iterative reconstruction or similar methods can be used to find a sparse solution for representing the volume in the dictionary of the coefficients. In an embodiment, in any such sparse representation of the volume by steerable coefficients, the strongest and/or non-zero magnitude indices can represent the structures (e.g. vessels) of interest, and the orientations can be extracted. In an embodiment, a 2D imaging plane is represented by coefficients of 3D steerable structures. In an embodiment, a 3D spatial representation is converted between a 3D steerable wavelet representation during reconstruction and simulation operations. In an embodiment, 3D steerable coefficients are found from a 3D wavelet representation of the volume by applying directional derivatives and the inverse square-root Laplacian operation or an approximation thereof. In an embodiment, the 3D representation of the volume can be used to remove streaking artifact of vessels crossing the imaging plane. In an embodiment, vessels are automatically detected using this method. In an embodiment, an image of the detected vessels is formed and is displayed overlayed on top of another image. In an embodiment, multiple wavelengths can be used in such detection as described herein. In an embodiment, only the oxygenation and/or hemoglobin levels of such detected vessels are displayed. In an embodiment, the detected vessels are converted to a data structure used to represent a vascular tree, vascular network or vascular segments. In an embodiment, the vascular tree representing data structure is used to improve motion tracking when motion is present between acquired frames. In this manner, determining the position of a vessel as it appears in two adjacent frames is possible, because a slight position or orientation offset can be tracked and accounted for, thus ensuring that a detected object corresponds to the same vessel. The represented vessels may provide useful structures for a motion tracking algorithm to lock onto. In an embodiment, the represented vessels (e.g. vascular segments) are assumed, to a first order, to follow a straight path, such that when a small motion is undergone by the probe, the position of a vessel in an adjacent frame is slightly shifted according to this approximated straight path followed by the vessel. For example, if a vessel follows the path of a line, and the imaging plane remains parallel in an adjacent frame, the position of the vessel in one frame compared to its adjacent frame can be visualized as a line intersecting two parallel planes, and the orientation of the vessel in each plane will correspond to the slope of the line. In an embodiment, the shift in position of a vessel of given orientation that is not parallel to the motion can be used to estimate the speed of the motion when the duration between the acquired frames is taken into account. In an embodiment, the vessels or vessel segments are represented as lines or line segments. In an embodiment, a vessel has a vessel configuration with parameters such as position and/or orientation. In an embodiment, an acquired frame is represented as a reference plane and an adjacently acquired frame is represented as a plane with an unknown configuration (e.g. position and orientation) that intersects the lines (or line segments) representing the vessels. In an embodiment, the unknown configuration is solved by finding a configuration that minimizes the sum of errors (e.g. distances) between the mapped position of each detected vessel in the adjacently acquired frame (when mapped through a transformation from the reference plane to the configuration of the unknown plane) to the intersection of the line representing the vessel and the unknown plane. In an embodiment, this can be solved by minimizing a linear program.

Figure 3B:
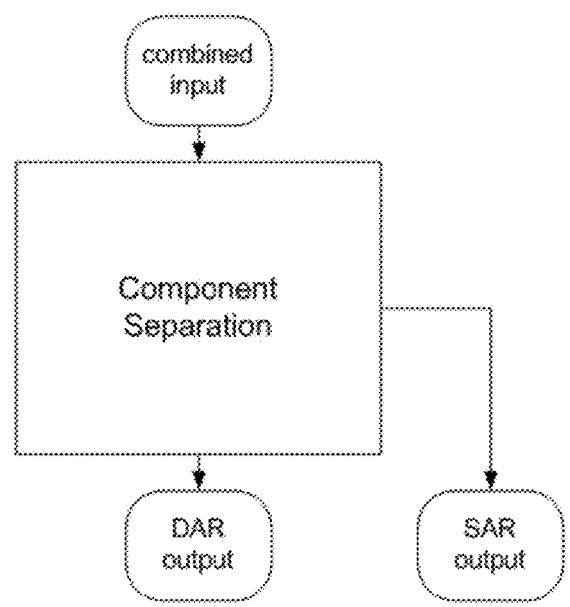
FIG. 3B is a block-level process flow chart illustrating an overall component separation process in accordance with an embodiment.

In an embodiment, the affine transformations (e.g. undergone by a probe) between such locked onto structures can be determined. In an embodiment, when orientations of substantially all detected vessels (or other such targets) between adjacent frames are subjected to the same (on average) affine transformation, this substantially reveals the motion undergone by a probe, and the motion may be extracted by solving it from a determined overall affine transformation subject to the constraints of rigid motion. In an embodiment, if the orientations of the vessels remains constant, the motion of the probe is parallel. In an embodiment, the solved transformation is a best-fit solution of the motion undergone by the probe. In an embodiment, the solved transformation must be adapted to produce the motion undergone by the probe (e.g. using a coordinate transformation). In an embodiment, the affine transformation is a linear transformation or a coordinate transformation. In an embodiment, the location of an unknown plane that intersects lines representing the vessels is solved to find the motion of the probe. In an embodiment, non-rigid tissue deformation has also occurred, and this can be solved by computing a difference between the affine transformation found for each vessel (or target) and the overall affine transformation, and substantially using interpolation to determine the deformation map for the remainder of volume representation. In an embodiment, when no vessel structures are present, correlation analysis between tissue regions of adjacent frames can be used for freehand motion tracking f. Output/Storage Device FIG. 3B is a block diagram showing an overall component separation process. In an embodiment, an output module is provided capable of outputting one or more spatial representations or acoustic signals in a manner that they can be viewed, stored, passed, or analyzed by a user or other analysis module. In an embodiment, unrefined spatial representations reconstructed from recorded acoustic signals are displayed or output. In an embodiment, spatial representations are displayed or otherwise output after application of additional image processing. In an embodiment, intermediate spatial representations are output or displayed. In an embodiment, refined spatial representations are output or displayed. In an embodiment, reference DAR and SAR spatial representations are displayed or otherwise output. See, for example, FIGS. 5A, 5E, 6A, and 6E. In an embodiment, PSF spatial representations are output or displayed. See, for example, FIGS. 5D, 5H, 6D, and 6H. In an embodiment, component separated spatial representations are output or displayed with or without thresholding. See, for example, FIGS. 5B, C, F, G, 6B, C, F, G. In an embodiment, only the DAR representation and not the SAR representation is output or displayed, in which case the SAR representation may be discarded. In an embodiment, signal domain DAR or SAR are output or displayed, which may be computed by applying the simulation module to the spatial representation. In an embodiment, processed representations of DAR or SAR are output or displayed as shown in FIG. 3B.

B. Surface Wave Separation

An acoustic signal and the resulting sinogram may also contain an acoustic surface wave (ASW) signal. In an embodiment, the method of component separation described above, can be adapted to include the separation or removal of the surface wave component from acoustic signals. In an embodiment, this can be done with our without separation of the SAR component. Thus, in an embodiment, a DAR component is separated from an ASW component. In other embodiments, an ASW component is separated from an SAR component, with or without separation of the DAR component. In an embodiment, no significant wavefront is produced; and thus, there is no SAR component to remove.

In an embodiment, surface waves are modelled as point sources originating on a plane parallel to the probe's (or other system component's) surface, or following the surface of the tissue. In an embodiment, features of the probe (or other system component) may produce acoustic surface waves. Surface waves travelling along the surface of the probe can remain detectable even when the probe (or other system component) is not in contact with the volume. Such surface waves may change when the probe comes into contact with the volume. In an embodiment, this change may be used to detect when the probe comes into contact with the volume. In an embodiment, these surface waves may be modelled and separated. In an embodiment, surface waves may cause backscatter, when they reflect off features on the surface, or in the volume. The same methods described above for removing an SAR signal, can be applied to removal of an ASW signal, wherein the simulation and reconstruction are modified to simulate and reconstruct the surface waves rather than the DAR or SAR signals.

In an embodiment, first order surface waves from the probe features reach the acoustic receivers first. If the probe has a different speed of sound than the volume or a gel or other coupling medium used between the probe and the volume, then a wavefront propagating along the probe will reach the receivers in a different timeframe than the wavefront travelling along the surface of the volume or through the coupling medium. In an embodiment ASW may include mechanical waves travelling along the surface of the probe, the surface of the volume and/or through the coupling medium. Measuring the differences in arrival times of the signals can provide valuable information about the coupling. As the arrival times may be different for the waves travelling along the surface of the probe, the surface of the volume, and through the coupling medium, this implies that the speed of sound (e.g. shear or longitudinal) of each material is different. Thus, in an embodiment, this can be measured. In an embodiment, the differences in arrival times (or delays) are used to separate signal components as discussed above.

In an embodiment, if the features are horizontal or vertical to the detector elements, the surface waves will either reach all elements at the same time for parallel, or sequentially propagating to create a diagonal line in the sinogram. In an embodiment, stripe filtering can be used to remove such waves from the DAR component of a sinogram. In an embodiment, when the probe and the volume are coupled together, they are also surrounded by air, which is a configuration that may produce a surface wavefront resulting from a discontinuity at the boundary of the probe surface (as described in more detail below). In an embodiment, such a wavefront propagates sequentially to detector elements in an array (e.g. creating a diagonal line in a sinogram). In an embodiment, such a wavefront can be used, as described above, to infer information about the coupling interface (e.g. velocity or speed of sound of materials, status of coupling, thickness of coupling medium). In an embodiment, if the probe is partially coupled to the volume and partially exposed to air, this situation can be detected, and the position of where the coupling is lost can be determined. In an embodiment, the slope of a produced diagonal line in the sinogram is proportional the speed of sound of a surface wave, and thus can be used to measure it. In an embodiment, if the wave travels with different speeds, the observed diagonal line disperses. In an embodiment, when this occurs, the line fans out (e.g. an elongated triangle). In an embodiment, the intersection of a diagonal line in a sinogram with the time zero intercept indicates the position on the probe surface where the wavefront originated. In an embodiment, the intensity of the produce signal yields information about the coupling interface (e.g. acoustic impedances). In an embodiment, the change in intensity of the measured surface wave varying at sequential detector elements yields information (e.g. acoustic attenuation properties). In an embodiment, an opto-acoustic image is formed that uses at least one parameter computed from measuring an observed surface wave in the sinogram.

In an embodiment, an acoustic isolator can be used to mitigate shear waves, elastic waves or other such waves that would propagate internal to the probe, and in particular that can occur due to energy from the light path reaching the acoustic receivers. Thus, in an embodiment, when an isolator is used, the ASW component from features is assumed to have traveled proximate to the probe surface. In an embodiment, the isolator may reduce ASW surface wave component.

C. Finding DAR Components—Multiple Light Event Separation

Acoustic return signals resulting from multiple light events (e.g., laser pulses) may be captured in a single acquisition frame—e.g., a single sinogram. The single sinogram corresponds to one sampling period recording the acoustic return signal. In an embodiment, this produces a sinogram where the acoustic return signals from one light event may interfere with the acoustic return signals from another light event. In an embodiment, components of the acoustic return signal are later separated using component separation techniques. In an embodiment, the light events may occur at different predominant wavelengths. In an embodiment, the light events may occur at the same predominant wavelength. Wavelengths of light outside within or without the visual spectrum may be used. In an embodiment, other forms of electromagnetic radiation may be used in lieu of a light event. In an embodiment, the acoustic return signal from multiple light events are stored in a single sinogram. In an embodiment, the acoustic return signal may be captured in set of sinograms (e.g., a couplet of long and short sonograms captured in a single acquisition period). As further discussed below, the multiple light events may occur simultaneously or may be offset by a time delay while still being captured by acoustic receivers during a single acquisition frame. Substantial variability may be employed in the time delay because the sampling window is typically in the order of tens of microseconds, and more typically around 65 microseconds, a time delay of less than several microseconds would permit a substantial number of the sinogram samples to comprise data from two or more light events. In an embodiment, an extended sampling window could be used such that about 65 microseconds of sampling were present for each light event, and thus, a sampling period of, e.g., 68 microseconds could be used with a 3 microsecond offset between two light events. In an embodiment, two or more light events may be offset in time by at least one nanosecond, and not more than a few microseconds. In an embodiment, two or more light events may be offset in time by 1-3 nanoseconds, 3-5 nanoseconds, or more than 5 but less than 20 nanoseconds. In an embodiment, the time delay between two light events of different predominant wavelengths is at least 20 nanoseconds. In an embodiment, the time delay between two light events of different predominant wavelengths is at least 50 nanoseconds. In an embodiment, the time delay between two light events of different predominant wavelengths is between 50 and 100 nanoseconds, or between 100 and 500 nanoseconds, or between 500 nanoseconds and a microsecond. In an embodiment, the time delay between two light events of different predominant wavelengths is less than about two microseconds. In an embodiment, the time delay between two light events of different predominant wavelengths is equal in time to the period of at least one or more samples in the sinogram. In an embodiment, the time delay between two light events of different predominant wavelengths is equal in time to the period of at least five or more samples in the sinogram. In an embodiment, the time delay between two light events of different predominant wavelengths is short enough that a sinogram capturing the acoustic return from the two light events presents sufficient data from which the two light event components can be separated. In an embodiment, the two light events correspond to a short and a long wavelength of light as discussed above. In an embodiment, the resulting acoustic return signal is separated into short and long sinograms for storage, display, or further processing. Various methods of processing, analyzing, and separating the resulting acoustic signals are discussed below.

In an embodiment, each energy event may have a time domain optical energy impulse response that indicates the energy output as a function of time. In an embodiment, the time domain optical energy impulse response is measured by a sensor and is stored. In an embodiment, the time domain optical energy impulse is represented in the frequency domain. In an embodiment, acoustic signals associated with an energy event may be deconvolved with a deconvolution filter based on the optical energy impulse response. In an embodiment, the deconvolution filter is a Wiener filter.

Separation of Data from Multiple RF Events in a Single Acquisition Frame

Parametric maps can be computed using the methods described in U.S. patent application Ser. No. 13/507,217, filed Jun. 13, 2012, which is incorporated by reference herein. In an embodiment, multiple pulses of electromagnetic energy are delivered to the volume. In an embodiment, multiple energy pulses are delivered to the volume within a single acquisition frame, the acquisition frame corresponding to a measurement event of recording a resulting acoustic signal. In an embodiment, despite being delivered in the same acquisition frame, the energy pulses are offset and the time difference of the resulting acoustic return is used to process the acoustic signal. In an embodiment, at least one of the multiple energy pulses is delivered at a different RF frequency from the others and the differences in frequency are used to process the resulting acoustic return.

In an illustrative embodiment, the electromagnetic energy is light energy and multiple wavelengths of light can be fired at the same moment in a single frame, with the frame in its entirety corresponding to a measurement event. The molecular concentrations can then be decoded by analyzing several measurement events with different combinations of fired light (e.g., laser) wavelengths in each measurement event by using Frequency-Hopping Spread Spectrum or other similar techniques. In an embodiment, multiple laser wavelengths can be fired in a single frame, (but it is believed that it would be advantageous if they were not fired at the same moment), wherein molecular concentrations can be determined by analyzing the frame using Blind Source Separation or a similar technique. In an embodiment, the multiple wavelength single frame approach improves sensitivity to motion. In an embodiment, the analyzing steps may include solving systems of absorption equations from laser wavelengths to determine molecular concentrations in one or more portions of the volume. In an embodiment, when multiple laser wavelengths are fired in a single frame, but not at the same moment, Blind Source Separation can be used to separate components of the resulting acoustic return. One approach to performing Blind Source Separation when multiple laser wavelengths are fired in a single frame, but not at the same moment, can be an adaptation of the MCA technique of Bobin et. al., in *Morphological Diversity and Sparsity for Multichannel Data Restoration*, Journal of Mathematical Imaging and Vision, Vol. 33, Issue 2, pp. 149-168 (February 2009), the entire disclosure of which is incorporated herein by reference. In an embodiment, when a single frame corresponds to a single observation, the mixing matrix reduces to a mixing vector.

In another aspect of an embodiment of the subject invention, to measure an acoustic signal comprising multiple opto-acoustic return signals corresponding to multiple light events occurring in a volume of tissue, the transducers in the probe 102 can be sampled for a period of time after a first light event. In an embodiment, a second light event can occur following a delay after the first light event, where the delay is less than the period of time for sampling the acoustic signal. In an embodiment, the transducers in the probe 102 can be sampled for a period of time after the light event approximately equal to the time it would take sound to travel a desired distance in the tissue. In an embodiment, after the first light event, the sound has travelled less than the desired distance before the second light event occurs. Thus, in an embodiment, multiple acoustic return signals from multiple light events may be mixed together in an acoustic signal. In an embodiment, the desired distance may be at least one centimeter. In an embodiment, the desired distance may be at least two centimeters. In an embodiment, the period of sampling would correspond to the amount of time it would take sound to travel at least one, but not more than 15 centimeters in tissue. In an embodiment, the period of sampling would correspond to the amount of time it would take sound to travel at least five, but not more than 12 centimeters in tissue. In an embodiment, the desired distance may be less than one centimeter. The sampling rate should be sufficient to obtain sufficient information in the opto-acoustic return signal. In an embodiment, the sampling rate is above 20 Mhz, in another embodiment, the sampling rate is above about 30 Mhz. In an embodiment, the sampling rate is about 31.25 Mhz.

In an embodiment, when multiple acoustic return signals are mixed together in an acoustic signal, the total amount of time used to collect data from each wavelength may be less than the time required to perform independent acquisitions for each wavelength. Thus, in an embodiment, collecting a first sinogram containing mixed acoustic return signals corresponding to multiple light events, allows collection of data faster than collecting multiple unmixed sinograms corresponding to each light event.

Coded excitation may be used for each wavelength to improve signal to noise ratio, and to permit the separation of signals corresponding to each optical wavelength by deconvolution of the measured signals against the known codes. This can, for example, improve the penetration depth of a system that uses laser diodes as an optical source.

In an embodiment, a light event can result from a high power pulsed laser source. In an embodiment, each wavelength may correspond to a light event that is a single pulse. In an embodiment, one light event for each wavelength is used. In an embodiment, many light events for each wavelength can be used. In an embodiment, a first light event corresponds to a pulsed Nd:YAG laser emitting a predominant wavelength of around 1064 nm and a second light event corresponds to a pulsed alexandrite laser emitting a predominant wavelength of around 757 nm. In an embodiment, the first predominant wavelength and the second predominant wavelength are the same.

Figures 11A, 11B, 11C:
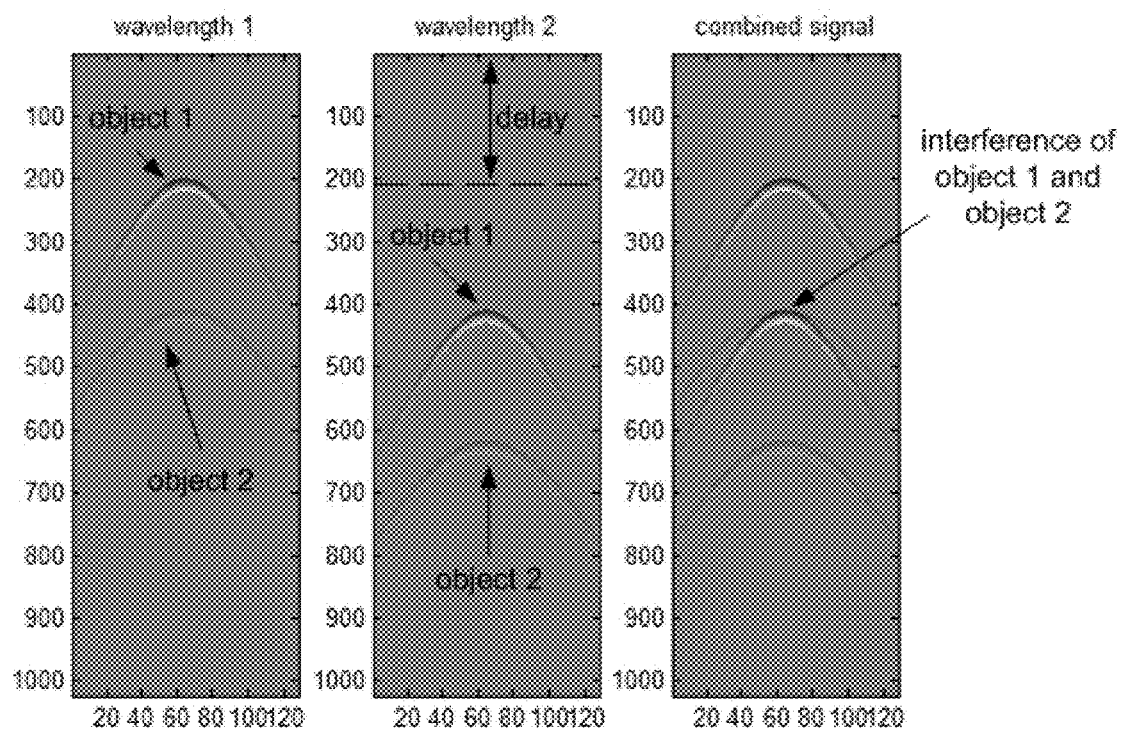
FIGS. 11A through 11C are graphs illustrating sonogram simulations of two spherical objects at different depths in a tissue.
Figure 11D:
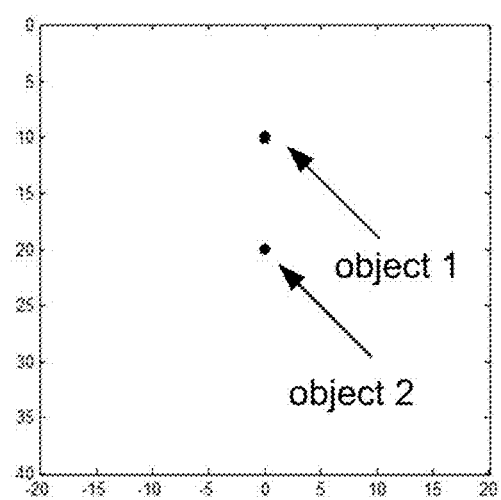
FIG. 11D is a graph illustrating the layout of the spherical objects in the volume.

FIGS. 11A-C show sinogram simulations of two spherical objects at different depths in a tissue where a second light pulse is emitted following a delay after a first light pulse. The x-axis corresponds to transducer number. The y-axis corresponds to sample number. FIG. 11D shows the layout of the spherical objects in the volume. FIG. 11A shows the components of the first predominant wavelength. FIG. 11B shows the component of the second predominant wavelength. The delay shown is approximately 200 samples. FIG. 11C shows the sinogram of the combined signal. The interference of object 1 with object 2 is shown in FIG. 11C. Even though the objects are both spherical, the curves that they produce in the sinogram are different because they are located at different positions. Thus, blind source separation can be used to separate the mixed acoustic return signals by accounting for this effect as discussed above.

In an embodiment, the technique for component separation described above is used to separate multiple acoustic return signals mixed into an acoustic signal in the form of a sinogram.

In an embodiment, a system is provided comprising at least one energy source configured to deliver electromagnetic energy to a volume of tissue such that when the electromagnetic energy is delivered an acoustic signal is detectable with at least two components: 1) a first DAR signal from a first light event; and 2) a second DAR signal from a second light event. The DAR signals may result from temporal stress confinement within one or more electromagnetically absorbent targets in the volume. In embodiment, the acoustic return signal also contains first and second SAR components. The acoustic signal may also contain shear or surface wavefront components as discussed below. The second light event may follow the first light event after a delay. In an embodiment, more than two light events may be used.

In an embodiment, the first light event comprises delivery of light at a first predominant wavelength of light and the second light event comprises delivery of light at a second predominant wavelength of light. Targets in the volume may have different absorptions of the first and second predominant wavelengths of light. Nonetheless, in an embodiment, the electromagnetically absorbent targets of the first predominant wavelength may also absorb some electromagnetic energy from the second predominant wavelength, and vice versa. In an embodiment, the DAR signals are ultrasound signals. In an exemplary embodiment, the electromagnetic energy is light energy and the DAR signal is an opto-acoustic return signal. In other embodiments, the electromagnetic energy is delivered from another part of the RF spectrum. As will be appreciated by one skilled in the art, the entire RF spectrum is applicable to the disclosed method and system.

a. Light Source

In an embodiment, a single light source is used, the single light source delivering light (or other electromagnetic energy) to a volume of tissue at a single wavelength—or within a very narrow band of wavelengths. In an embodiment, multiple light (or energy) sources are used, each being able to deliver electromagnetic energy to a volume at a narrow band or single wavelength. In an embodiment, light is delivered through the distal end of a probe that may be positioned proximate to the volume. In an embodiment, the light is delivered via a light path from the light source to the distal end of the probe. The light path may include fiber optic cables or other transmission means. The light path may include one or more light exit ports, and may also comprise one or more lenses, one or more diffusers, and/or other optical elements.

In an embodiment, the light source comprises a tunable laser capable of delivering light to the volume at different predominant wavelengths at different times. In an embodiment, the light source delivers multiple wavelengths of light at the same time (i.e., having multiple narrow bands of light in a single light pulse). In an embodiment, multiple light sources are used, each having its own light path. In an embodiment, the light paths overlap in whole or in part. In an embodiment, two lasers are used capable of delivering pulses of light at different predominant wavelengths. In an embodiment, an NdYAG laser capable of emitting a wavelength of around 1064 nm and alexandrite laser capable of emitting a wavelength of around 757 nm are used. In an embodiment, the light source for producing light at or near a predominant wavelength is selected from the group consisting of a laser diode, a LED, a laser diode array, and a pulsed direct diode array.

In an embodiment, a second light source is fired after a delay. In an embodiment, the delay is caused by a timer or by an electronic or mechanical process capable of sending a delayed signal, or capable of sending two signals having a predetermined delay there-between. In an embodiment, the first and second light sources use the same electrical trigger, but the path of the trigger to the second light source is longer, and thus it takes the electricity longer to reach the second trigger. In an embodiment, a single light source is used, but the light beam or path is split and the second light path configured such that it takes longer for the light to travel to the volume. For example, the light in the second light path can be passed through a material having a lower speed for the transmission of light.

b. Transducer Array

In an embodiment, the system comprises one or more receivers for receiving the resulting acoustic signals such as the transducer arrays or other receivers described above.

c. Processing Subsystem

A component separation system and method according to the disclosure in this section further comprises a processing subsystem adapted to analyze the acoustic signals to obtain information regarding electromagnetically absorbent targets in the volume. In an embodiment, the processing subsystem analyzes the acoustic signals to produce a spatial representation of the targets in the volume. In an embodiment, the system uses a time delay between the reception of a first DAR signal and a second DAR signal to better analyze the signals. In an embodiment, the system separates the first DAR signal and the second DAR signal and processes them differently based on the time delay or other parameters. In an embodiment, the system separates the acoustic signal into a component caused by a first RF wavelength and a component caused by a second RF wavelength. In an embodiment, rather than separating the components into multiple DAR signals (or images), the chromophore concentrations and/or molecular information about the volume is extracted without the need of the intermediate step of separating the signals (or images) of each wavelength. In an embodiment, an MCA mixing matrix is used. The chromophores may be known or unknown. In an embodiment, the system separates three or more DAR signals (such as DAR signals caused by three or more wavelengths of light). In an embodiment, the system separates multiple DAR signals and at least one SAR signal. In an embodiment, the system separates multiple SAR signals and at least one DAR signal. In an embodiment, the component separation system and method according to the disclosure in this section is adapted to separate a plurality of DAR signals and a plurality of SAR signals. In an embodiment, the component separation system and method according to the disclosure in this section is adapted to separate at least one DAR signal, at least one SAR signal, and at least one ASW signal from a sinogram comprising those signals. In an embodiment, wavelength specific features (e.g., codes) of the probe, as described herein, may be used to assist with separation of wavelength specific SAR components according to the disclosure in this section.

In an embodiment, the processing subsystem comprises: 1) a reconstruction module capable of analyzing acoustic signals to produce estimated spatial representations of targets in a volume (such as the electromagnetically absorbent targets discussed above); and 2) a simulation module capable of analyzing spatial representations of targets in a given volume (such as the estimated spatial representations produced by the reconstruction module) and generating acoustic signals that might be produced by applying electromagnetic energy to the given volume. In an embodiment, the reconstruction and simulation modules perform adjoint operations as discussed above: the reconstruction module obtaining acoustic signals and producing spatial representations; and the simulation module obtaining spatial representations (such as those produced by the reconstruction module) and producing (e.g., back-projecting) acoustic signals that might be produced when electromagnetic energy is applied to a volume with the given spatial representations. In an embodiment, the spatial representations are converted to a transformed domain using a transform such as wavelets or other similar sparse representation.

In an embodiment, the simulation and reconstruction for the first DAR signal and second DAR signal account for the delay between the light events. In an embodiment, this is done by shifting the sinogram by a number of samples corresponding to the delay prior to the reconstruction or after the simulation. In an embodiment, a simulation and reconstruction for each of many DAR signals may be implemented in this way, by shifting the sinogram by corresponding delays for each light event. Accordingly, in an embodiment, the PSF for each DAR image or signal incorporates the delay between light events.

In an embodiment, the processing subsystem comprises a component separation module capable of applying the simulation, reconstruction, point spread function, error calculation, and/or correction modules discussed above to separate at least two components of a given acoustic signal as discussed above. In an exemplary embodiment, the given acoustic signal is separated into the first DAR and second DAR components. In an embodiment, the reconstruction module is applied to the given acoustic signal to produce a reference first DAR spatial representation and a reference second DAR spatial representation of a volume that produced the given acoustic signal. The reference spatial representations can also be used as initial values for initial DAR spatial representations. In other embodiments, the DAR spatial representations can be initialized to all zeros, threshold values, weight values as discussed above, or other specified values. The point spread function module can then be applied to the initialized DAR spatial representations to produce first PSF DAR and second PSF DAR spatial representations of the volume. Next, the error calculation module can be applied to determine the residual error between the reference and the PSF DAR spatial representations. The correction module can then be applied to correct the initial DAR spatial representations based on the residuals to produce refined DAR spatial representations of the volume. The component separation module can be applied to produce separate images of electromagnetically absorbent targets in the volume for each wavelength. In another aspect of the invention, the above steps are applied to a given acoustic signal as a process with or without the provided system. The process can be extended to separate three or more DAR signals. In other embodiments, wavelet representations of the spatial domain are used rather than spatial representations in a similar manner as described herein. In an embodiment, the thresholding operation is a denoising operation, as wavelet (or similar transformation domain) denoising can be similar or the same as thresholding. In an embodiment, the denoising is multi-spectral denoising. Various denoising techniques can be used with the subject invention including, but not limited to, those described in U.S. patent application Ser. No. 13/507,217, which has been incorporated herein by reference.

Figure 12A:
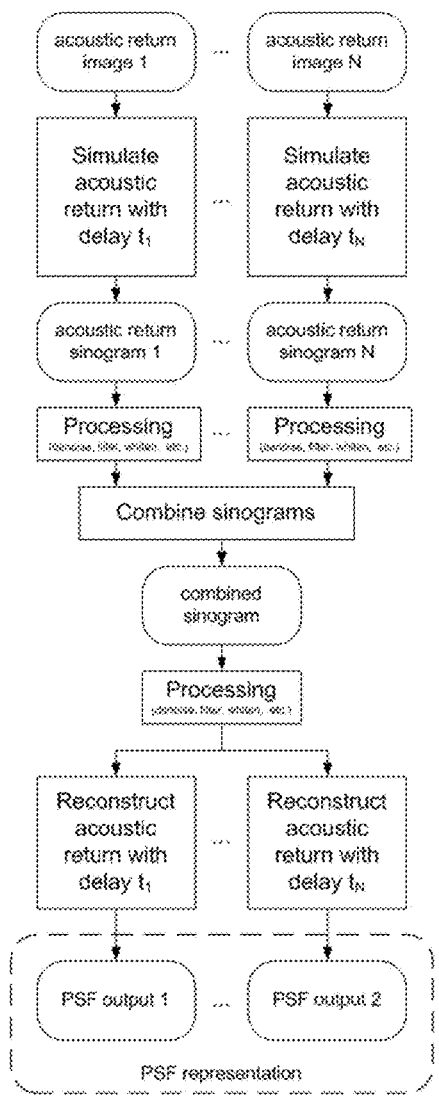
FIGS. 12A and 12B are block-level flow diagrams illustrating process flows that can be used to separate acoustic signals from multiple energy events.
Figure 12B:
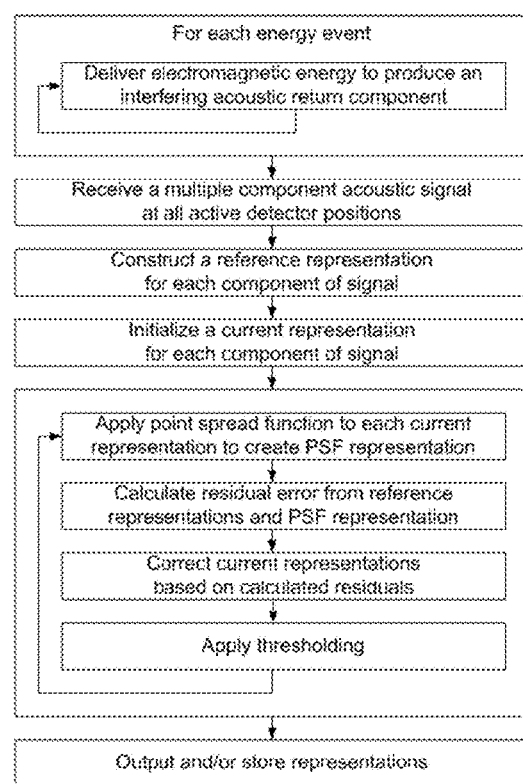

FIGS. 12A and 12B show process flows that can be used to separate acoustic signals from multiple energy events. FIG. 12A shows an illustrative embodiment of a PSF for multiple energy event separation. FIG. 12B shows an illustrative embodiment of component separation for multiple energy event. In accordance with the embodiment of FIG. 12B, for each energy event, electromagnetic energy is delivered to produce an interfering acoustic return component. A multiple component acoustic signal is received at all active detector positions. A reference representation is then constructed for each component of the signal. A current representation is initialized for each component of the signal. An iterative process then begins by applying a point spread function to each current representation to create a PSF representation. Residual error is then calculated from reference representations and the PSF representation. The current representations are corrected based on the calculated residuals. Thresholding is then applied, and the iterative process returns to the step of applying a point spread function above. After the iterative process, the representations are output and/or stored.

In an embodiment, the given acoustic signal is separated into first chromophore and second chromophore component images. In an embodiment, a relationship between chromophore concentrations and optical wavelengths is given by a matrix (or its pseudo-inverse) that relates the optical absorption coefficient of each chromophore for each wavelength. In an embodiment, the reconstruction module is applied to the given acoustic signal to produce a reference first chromophore spatial representation and a reference second chromophore spatial representation of a volume that produced the given acoustic signal. The reference spatial representations can also be used as initial values for initial chromophore spatial representations. In other embodiments, the chromophore spatial representations can be initialized to all zeros, threshold values, weight values as discussed above, or other specified values. The point spread function module can then be applied to the initialized chromophore spatial representations to produce first PSF chromophore and second PSF chromophore spatial representations of the volume. Next, the error calculation module can be applied to determine the residual error between the reference and the PSF chromophore spatial representations. The correction module can then be applied to correct the initial chromophore spatial representations based on the residuals to produce refined chromophore spatial representations of the volume. The component separation module can be applied to produce separate images of electromagnetically absorbent targets in the volume for each wavelength. In another aspect of the disclosed methods, the above steps may be applied to a given acoustic signal as a process with or without the provided system. In other embodiments, wavelet representations of the spatial domain are used rather than spatial representations in a similar manner as described above.

The techniques of Bobin and Guerquin-Kern may be utilized in the novel methods and systems described herein. In an embodiment, using the technique of Bobin, chromophores can be converted between wavelength representations through hyper-spectral dictionary elements, and spatial representations can be represented as wavelets. In an embodiment, the PSF can be used to represent the spatial or wavelet representations in as PSF dictionary elements. Furthermore, the blind source separation mixing matrices can be solved and included with the techniques above as described in Bobin. In an embodiment, a source may be represented as a chromophore and a measurement may be a sinogram. In an embodiment, a source may be represented as the acoustic return profile of the volume for a wavelength. The component separation may also be performed by using the MCA or mMCA algorithms. In an embodiment, the PSF is implemented by applying simulation operation, sinogram delay operation, and reconstruction operation. In an embodiment, multiple mixed sinograms are collected. In an embodiment the mMCA algorithm is applied to multiple mixed sinograms (for example, a first mixed sinogram may contain DAR signals from a number of light events and a second collected mixed sinogram may contain DAR signals a number of light events). In an embodiment, the sequences and wavelengths of light events may vary from frame to frame. In an embodiment, the MCA or mMCA algorithm can be applied to multiple unmixed sinograms to retrieve chromophore concentrations. In an embodiment when a single sinogram is used, the mixing matrix reduces to a mixing vector.

In an embodiment, sinograms containing multiple DAR signals can also contain multiple SAR signals. Hence, the techniques described herein can be adapted to separate sinograms containing multiple DAR and multiple SAR components.

d. Output/Storage Device

In an embodiment, a component separation system according to the present teaching may comprise one or more output or storage devices such as the output or storage devices described above. In an embodiment, a first spatial representation corresponding to a first light event is displayed and a second spatial representation corresponding to a second light event is displayed. In an embodiment, a spatial representation combining information from two or more light events are displayed. In an embodiment, one or more intermediate or final spatial representations are stored as discussed above. In an embodiment, one or more intermediate or final signal components can be stored in sinograms or using other techniques discussed above. In an embodiment, spatial representations of molecular component concentrations are output.

D. Multiple Frame Separation

In an embodiment, a sinogram includes data collected in a single acquisition frame. In an embodiment, a frame set comprises multiple frames that correspond to sinograms that are collected sequentially.

In an embodiment, a component separation system according to the present teaching may comprise a control unit adapted to produce triggering events to demarcate acquisition frames in a frame set. In an embodiment, the system comprises a data acquisition unit adapted to sample the set of acoustic receivers during a period of time following triggering events and to store the sampled data as a set of acoustic signals thereby producing an acquisition frame.

In an embodiment, a component separation system according to the present teaching comprises: a.) a least one acoustic receiver configured to receive acoustic signals from a volume; b.) a source of electromagnetic energy configured to deliver electromagnetic energy events to the volume; c.) a data acquisition unit adapted to sample the set of acoustic receivers during a period of time following triggering events and to store the sampled data as a set of acoustic signals thereby producing an acquisition frame; d.) a control unit adapted to produce triggering events to demarcate frames in a frame set, where the frame set contains at least one frame and each frame contains sampled data corresponding to at least one energy event; e.) a data processing subsystem comprising a component separation module configured to separate multiple signal components contained in the acoustic signals in the frames of the frame set; and f.) a display device adapted to display data derived from at least one of the separated components.

In an embodiment, a plurality of the multiple components are selected from a group comprising DAR, SAR, PAB, ASW, PASW (produced acoustic surface wave) and an additional component. In an embodiment, the frame set contains a single frame with a single energy event. In an embodiment, the frame set contains a first frame of one electromagnetic wavelength, and a second frame of another electromagnetic wavelength. In an embodiment, each frame corresponds to more than one energy event and the multiple components comprise interfering acoustic return signals produced by each energy event. In an embodiment, the frame set contains a single frame. In an embodiment, multiple frame sets are processed. In an embodiment, the frame sets are processed in real-time. In an embodiment, the electromagnetic energy is light. In an embodiment, the displayed data is a spatial representation of the volume. In an embodiment, the system further comprises a probe, acoustic receivers located on the probe, and an output port for the electromagnetic energy delivered via the probe. In an embodiment, the probe contains a wavefront producing pattern or features and a wavefront produced by the pattern or features produces PAB signals (by reflection from acoustically reflective targets in the volume), such that the component separation module is adapted to make use of a resultant nature of the acoustic backscatter signals caused by the pattern or features.

Figure 13A:
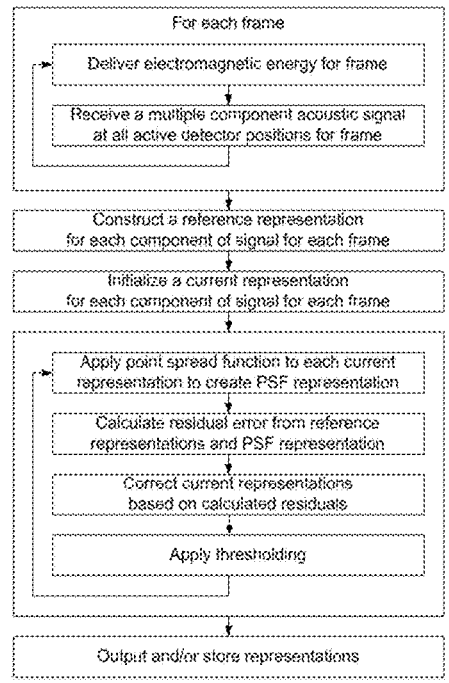
FIGS. 13A through 13D show process flows that can be used to separate acoustic signals from multiple acquisition frames.

FIGS. 13A through 13D show process flows that can be used to separate acoustic signals from multiple acquisition frames. FIG. 13A is an illustrative embodiment of a flow diagram for multiple frames. The process begins with an iterative process wherein, for each frame, electromagnetic energy is delivered and a multiple component acoustic signal is received at all active detector positions. Then, a reference representation is constructed for each component of the signal for each frame. A current representation is then initialized for each component of the signal for each frame. Then, an iterative process begins by applying a point spread function to each current representation to create a PSF representation. The iterative process then calculates residual error from reference representations and the PSF representation. The current representations are then corrected based on calculated residuals. Thresholding is applied, and the iterative process returns to the step of applying a point spread function above. After the iterative process, the representations are stored and/or output.

Figure 13B:
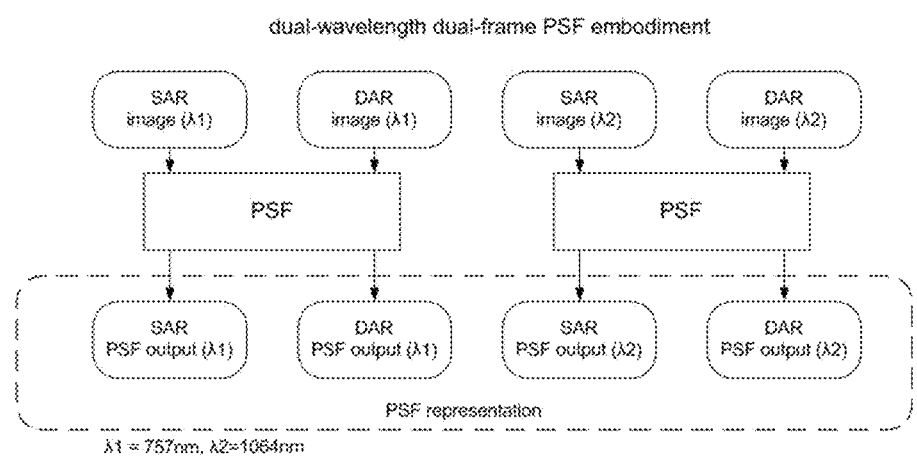
Figure 13C:
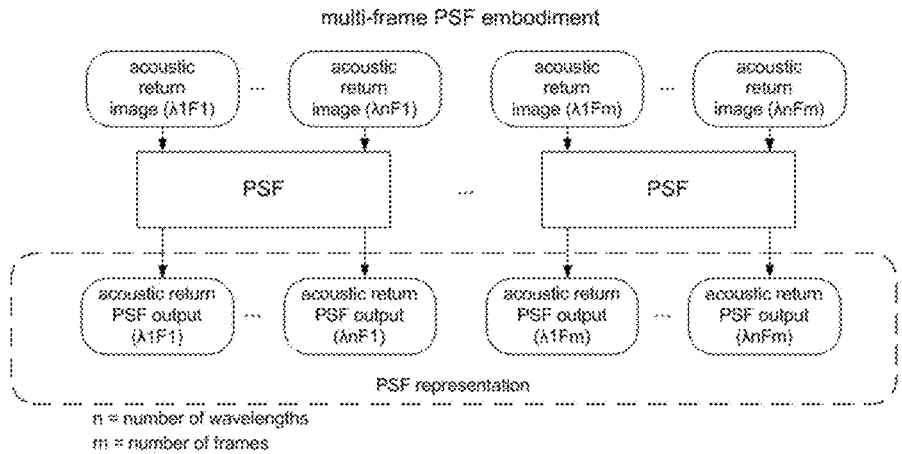
Figure 13D:
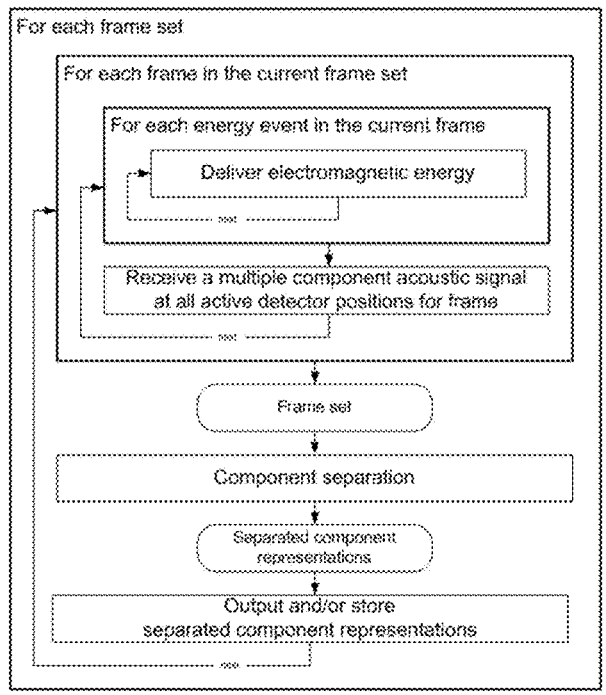
Figure 14A:
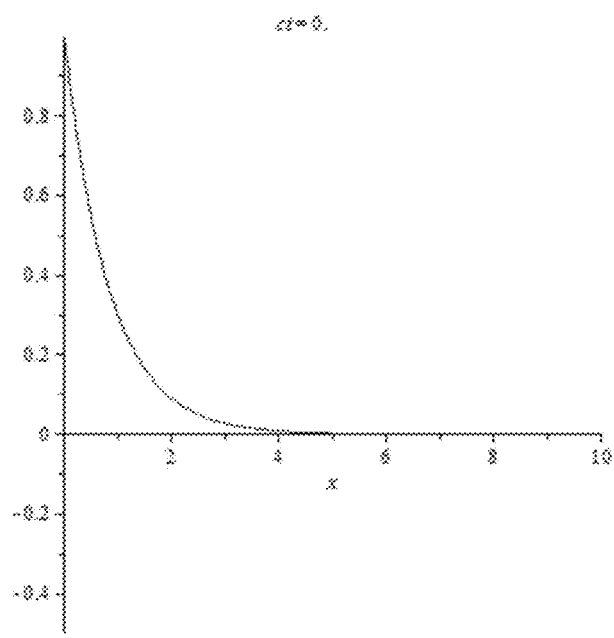
FIGS. 14A through 14E show graphs illustrating an ideal wavefront from volumetric illumination propagating into tissue at different snapshots in time.
Figure 14B:
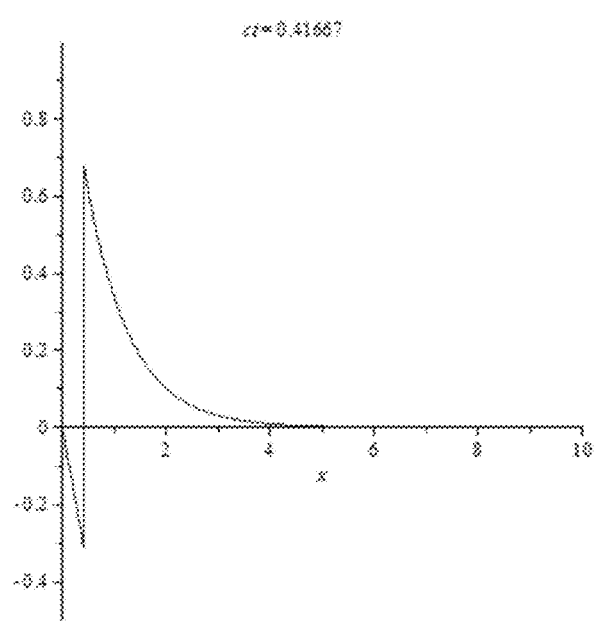
Figure 14C:
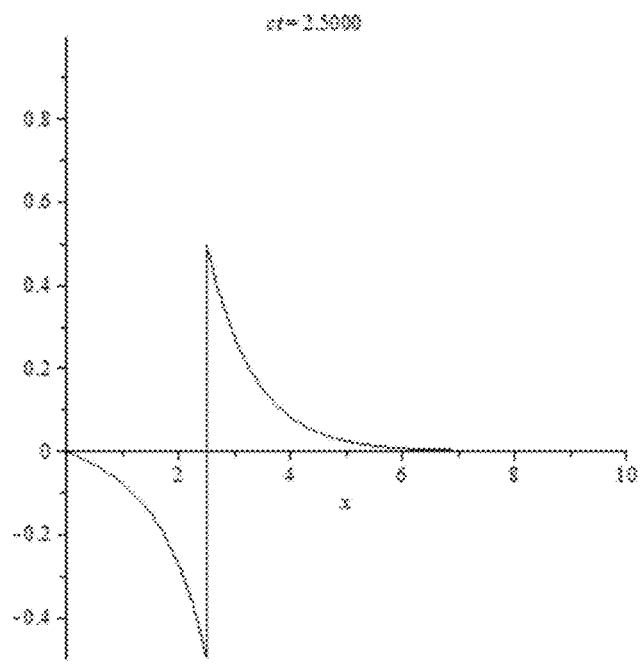
Figure 14D:
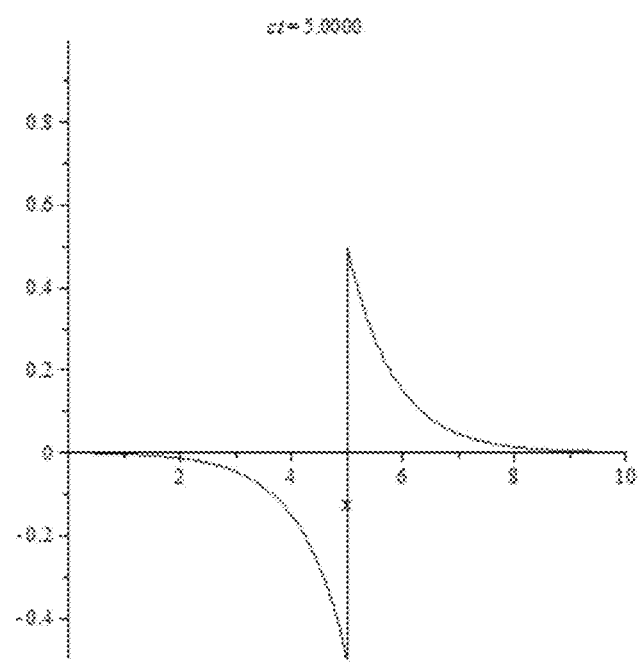
Figure 14E:
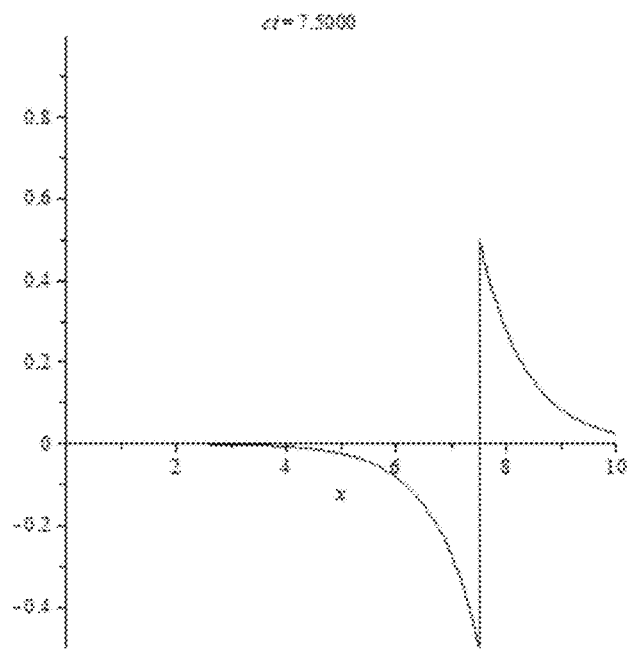

FIG. 13B is an illustrative embodiment of PSF for dual wavelength SAR/DAR separation. FIG. 13C is an illustrative embodiment of PSF for multi-wavelength multi-frame acoustic-return separation. FIG. 13D is an illustrative embodiment of a flow diagram for multiple-frame with multiple-light event component separation, in a general case.

E. Types of Wavefronts

Acoustic wavefront(s) can result from various sources. For example, an acoustic wavefront can result when a source in or proximate to the volume absorbs the electromagnetic energy and produces acoustic pressure. Generally this acoustic pressure is the result of the release of temporal stress confinement. In an embodiment, the electromagnetic energy is delivered to the volume via a probe. In an embodiment, the electromagnetic energy may be created by a light source within the probe, or a light source that is fed to the probe (e.g., via a light path). The source of an acoustic wavefront can also be in or on the volume. In an embodiment where the volume is tissue, sources of an acoustic wavefront can include, e.g., a vessel (e.g., a blood vessel) or feature of the epidermis. In addition to being in or on the volume, acoustic wavefronts can also be produced by acoustic energy absorbed or reflecting off of an element, feature, target, material, or other source that is external to the volume. For example, the acoustic energy may reflect off of a reflective element or feature in or on the delivery mechanism for the electromagnetic energy, the acoustic receiver, and/or materials used to house them (e.g., the probe). The reflecting acoustic energy may be caused by background initial pressure resulting from the electromagnetic heating of the volume. An acoustic wavefront can also result from acoustic energy reflecting off an impedance mismatch between materials in or proximate to the volume. For example, the acoustic wavefront can be produced when a portion of a surface of the volume is adjacent to a medium that is not perfectly matched to the acoustic properties of the volume. In an embodiment, electromagnetic energy is delivered to a volume via a probe that is proximate thereto, and an acoustic wavefront originates at the interface between the probe and a surface of the volume. In an embodiment, where the volume is human or animal tissue, an incident wavefront may originate at the surface of the skin. The incident wavefront may be due to an impedance mismatch, the skin-probe interface and/or, in an embodiment, a skin-air interface adjacent to the skin-probe interface. In an embodiment, where the volume is human or animal tissue, an incident wavefront may originate from the epidermal layers of the skin, and/or in or at the surface of a coupling medium positioned on the probe, on or the skin, there between and/or proximate thereto. In an embodiment, the probe may be acoustically mismatched with the volume. In an embodiment, acoustic transmitters or one or more transducers may be used to generate acoustic wavefronts. It will be understood that an incident acoustic wavefront may be partly reflected from a target with weak acoustic scattering such that substantially lower energy is diverted to the reflected wave than is contained by the incident wavefront. Moreover, it will be understood that an acoustic target may also be a wavefront source and vice versa.

Use of the term wavefront here is not intended to imply that it is only the front of the wave that may create SAR or other signal components. Hence, the term wavefront as used here includes a wave that may have a front as well as other parts of the wave (e.g., middle and rear). It is to be understood that any part of the wave may create SAR other signal components. In some circumstances, a wave may have more than one "wavefront."

Wavefronts Induced by Volumetric Illumination

When an opto-acoustic source homogeneously illuminates a half-plane (half space), a planar wave front will propagate. It can be represented as a function of one spatial parameter (e.g. depth). The equation can be derived as:

$$p(x, t) = \begin{cases} \frac{1}{2}H(x+ct) + \frac{1}{2}H(x-ct), ct < x \\ \frac{1}{2}H(x+ct) - \frac{1}{2}\alpha H(-x-ct), 0 < x < ct \end{cases}$$

where H is the 1D initial pressure distribution profile, and alpha is the strength of the reflection, x is depth, and p(x,t) is the pressure at depth x, time t, and c is speed of sound, and x>0.

FIG. 14 shows an ideal wavefront from volumetric illumination propagating into tissue at different snapshots in time: FIG. 14A shows initial 1D pressure distribution at the moment the laser is fired (t=0). FIGS. 14B through 14E show, a 1D wavefront propagating into tissue as it reflects off of surface acoustic mismatch (alpha=1).

In the situation involving a non-ideal produced wavefront, which may be the result from an opto-acoustic probe, the wavefront may not match an ideal plane wavefront resulting from an illuminated surface, or an ideal reflection resulting from a homogenously illuminated half-plane. Consequentially, in an embodiment, the layout of the probe (possibly including the layout of the acoustic detector, if the backscattered wave can be better inferred from a specific detector layout) must be accounted for. Thus, in an embodiment, consideration should be given in the design of a probe to the incident wavefront that it will produce. In an embodiment, a probe may be designed with an objective of reducing such a probe-caused incident wavefront. In an embodiment, a probe may be designed with an objective of maximizing such a probe-caused incident wavefront. In an embodiment, a probe may be designed with an objective of ensuring consistency across the variability arising in a clinical situation, so that component separation will be reliable. It is within the scope of this disclosure to quantify the effect that the features of a probe have on the generation of wavefronts, and use that information to separate SAR (or other signal components) from DAR. It is also within the scope of this disclosure to purposely configure a probe with features or a pattern to generate a wavefront and use the known wavefront producing features or patterns to separate SAR (or other signal components) from DAR.

Wavefronts from Discontinuities

In the boundaries inside of a tissue volume, when one tissue adjoins with the next tissue, the optical, acoustic, and mechanical properties of the volume may change because two different types of tissues may have different optical, acoustic, and mechanical properties. Taking blood vessels for example, blood vessels have low acoustic contrast compared with surrounding medium, but, because the optical contrast is high, the differences in such properties may not affect opto-acoustic image reconstruction. In an embodiment, such properties are considered substantially correlated. In an embodiment, the properties are treated independently. When the properties are treated independently, the simulation and reconstruction of the DAR may be performed separately from the simulation and reconstruction of the SAR.

Figure 15:
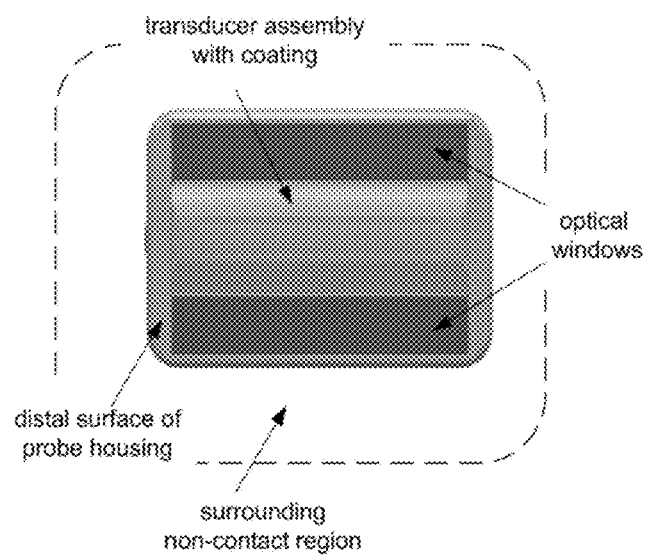
FIG. 15 is a diagram showing an end view of an embodiment of a probe that includes a non-contact region.

For acoustic waves, when a target acting as a source has a spatial boundary (a discontinuity), a wavefront may be emitted from the boundary. When a probe is placed on skin, the edges of the probe can act as boundaries. The tissue-air interface can also act as a boundary. The probe-air interface can also act as a boundary. Acoustic discontinuities can also act as boundaries. In opto-acoustics, sources of DAR are sources of initial pressure resulting from energy absorption. In opto-acoustics, when a source target has a boundary (discontinuity), the resulting source of initial pressure due to the energy absorption will be in the shape of that target. Thus, the boundaries of that target can help to determine the wavefronts. For example, a finite-length cylinder (as opposed to an infinitely long cylinder) has boundaries at the ends of the cylinder (as well as its cylindrical surface). In the ideal infinitely long case, only the cylindrical surface is accounted for. The ends of the cylinder, however, do produce wavefronts that may cause backscatter. The same holds true for the non-infinite contact of the skin with a probe through a coupling medium. For a simplistic probe face illustrated as a rectangle, instead of a large surface, the edges of the rectangle as well as the probe surface may produce wavefronts, and the surrounding air tissue interface may also form a wavefront. In an embodiment, tapering the edge of a probe may help to direct the wavefronts resulting therefrom. In an embodiment, wavefronts may be produced by the surface of the probe, including the transducer assembly, coatings, optical windows (optical exit ports), material discontinuities, the distal surface of probe housing, and the surrounding air (i.e., non-contact region). In an embodiment, a produced incident wavefront carries the acoustic impulse response from the pattern of the surface of the probe to acoustically reflective targets in the volume. FIG. 15 shows the distal surface of an embodiment of the probe including the non-contact region.

II. Coded Probe

In another aspect of the disclosed methods and apparatus, an element or feature (either on or in a probe or otherwise situated) is added or modified to produce one or more recognizable "artifacts" in resulting acoustic signals or spatial representations. In an embodiment, the recognizable artifact does not distort the DAR image or is substantially imperceptible to a human, but can be recognized by computer processing (e.g., like a digital "watermark"). In an embodiment, the recognizable artifact is perceptible in the image only when a physiological feature of tissue is present (e.g., to identify a cyst, to identify neovascularization, etc.). In an embodiment, the added or modified element or feature produces one or more predictable acoustic wavefronts or resulting waveform patterns. In an embodiment, it can be said that the probe or other component of the system is "patterned" or "coded" to produce the predictable wavefronts or waveforms. The predictable wavefronts or resulting waveform patterns can be described analytically, by simulation, or by experimentation and measurement. The processes and systems described above can then be modified to better isolate an SAR signal caused by the predicted wavefront(s) or waveform(s). For example, a transfer function can be designed to match the predicted wavefront(s) or waveform(s). In an embodiment, an SAR signal is isolated so that it can be removed. In an embodiment, the SAR signal is isolated and used to identify or watermark the signal or image produced. In an alternative embodiment, the SAR signal is isolated so that it can be used. For example, the element or feature may be used to enrich an opto-acoustic image. In an embodiment, the element or feature or wavefront is used to produce an ultrasound image, which can be separately displayed or co-registered with a DAR image. In an embodiment, simulation, analytical calculation or experimentation and measurement is performed to describe acoustic wavefront(s) or waveform(s) produced by existing elements or features of the probe (or other component of the system). The processes and systems described above can then be modified to account for the "patterning" or "coding" of the existing system.

At least some of the resulting scatter may reach acoustic receivers, where it can be received and later processed as discussed above. In an embodiment, interfering codes are decoded by separating the mutually orthogonal code sequences and determining their relative intensities and acoustic propagations. In an embodiment, interfering codes can be removed from images and data using the technique of interframe persistent artifact removal. An example of interframe (or inter-frame) persistent artifact removal is described in U.S. patent application Ser. No. 13/507,217, which has been incorporated herein by reference. In an embodiment, the code can be detected, and a function of its intensity across the sequence of the code can be analyzed to provide information about the source intensity related to the illumination reaching the surface of the probe. In an embodiment, interframe persistent artifact removal may be applied after determining the intensities of the code, and then adaptively computing a static artifact removal frame. In an embodiment, the pattern may represent a chirp, a line-width modulated chirp (represented by a pattern of lines of different width), a grating, a tone, a linewidth modulated tone (represented by a pattern of lines of different width), or other such linewidth modulated pattern, including a sinc function or a wavelet. Dithering may be used on a pattern to permit a gradualized wavefront intensity. In an embodiment, the pattern may be dots or pattern elements (e.g., shapes) arranged on a grid or lattice. In an embodiment, the pattern on one side of the receiver array may differ or be offset from the pattern on the opposite side of the receiver array so that the ASW or other signals reaching the array can be differentiated. In an embodiment, features may be arranged on a triangular lattice, where lattice points on one side of the array are offset from mirroring lattice points on the other side of the array so that the side of the arriving ASW signal for a feature can be differentiated. In an embodiment, codes may be used to probe the properties of the epidermal layer or skin (thickness, roughness, optical or mechanical properties), or of the coupling medium.

A. Principle of Creating Features

In an embodiment, the probe or other component of the system is coded by modifying its geometry. For example, the shape, edges, flatness, convexity, surface, texture, width, height, length, depth, or orientation of an element or feature can be changed. In another embodiment, the probe or other component of the system is coded by modifying the color, reflectivity, transmissiveness, or absorption of electromagnetic energy of an element or feature. For example, in the case of light energy, a darker color can be selected that will absorb more light energy or the color can be matched to one or more wavelengths produced by the light source. The speed of sound, thermal expansion, and/or specific heat capacity of materials of optically absorbing elements or features on the probe or system component can also be manipulated to produce a pattern. These mechanical properties contribute to the opto-acoustic efficiency parameter, which is also known as the Gruneisen parameter. Such mechanical properties can affect the strength of a generated wavefront. In an embodiment, geometry can be used in conjunction with optical properties and/or mechanical properties of the element or feature. For example, colored bands could be added to a probe's face, which can shift the produced SAR signal in a wavelength dependent manner. In another embodiment, optical properties can applied in combination with mechanical properties. Other coding or changes to the probe will be apparent to one of skill in the art, and can be used in connection with the novel coded probe and the methods of component separation associated therewith without departing from the scope of the subject matter of the inventions disclosed herein.

B. Basic Shapes Bars

Figure 16A:
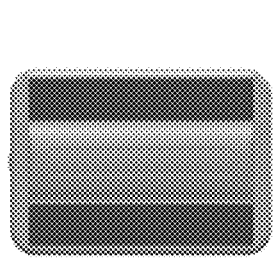
FIGS. 16A through 16H show examples of code shapes and configurations.
Figure 16B:
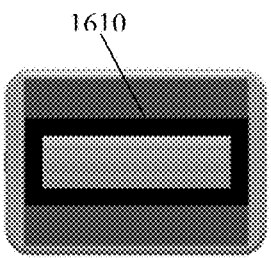
Figure 16C:
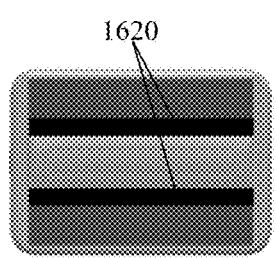
Figure 16D:
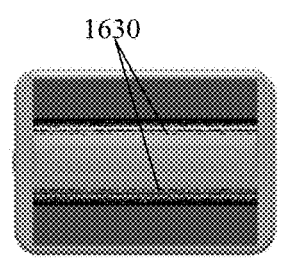
Figure 16E:
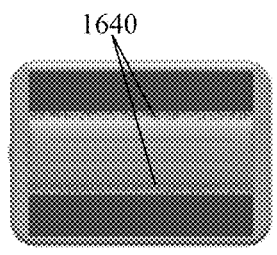
Figure 16F:
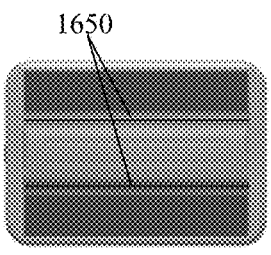
Figure 16G:
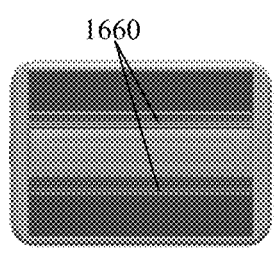
Figure 16H:
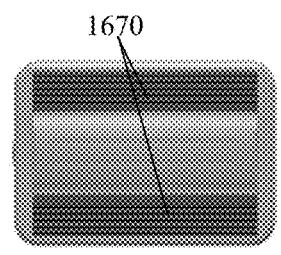

Probe features may include rectangular shapes, which surround a receiver element (such as the transducer assembly shown in FIG. 15), or may include one or more bars proximate to light exit ports (such as the optical windows shown in FIG. 15). Basic examples of code shapes and configurations are shown in FIGS. 16A through 16H. FIG. 16A shows light bars (optical windows), a coated surface of the transducer assembly, and the probe housing. FIG. 16B shows the features in a rectangular pattern 1610. FIG. 16C shows the features in a dual bar pattern 1620. FIG. 16D shows dithering applied to a 1-D chirp signal 1630. FIG. 16E shows code dots 1640. FIG. 16F shows a line-width-modulated sinc function as 1-D wavelet 1650. FIG. 16G shows a pattern of lines 1660. 16H shows a pattern of lines 1670 blocking an optical exit port.

C. Features

1. Geometry

In an embodiment, codes are constructed as feature dots (such as mutually orthogonal bit-sequences) on the surface of the probe, such that wavefronts from the feature dots scatter from targets. In an embodiment, features comprise one or more dots, bumps, bars, lines, grids, polygons, signals, bitmaps, wavelets, chirps, curves, curvelets, circles, crop circles, fractals, stripes, hatches, holes, ridges, squiggles, zigzags, ripples, corners, bends, outlines, insets, filled insets, cavities, inclusions, layers, beads, coatings, casings, openings, ends, edges, probe edges, fixtures, attachments, fittings, appendages, extensions, protrusions, or other shapes. Features may comprise a one-dimensional random bitmask, a two-dimensional random bitmask, a barcode, a two-dimensional barcode, a focusing pattern, evenly spaced or unevenly spaced concentric circles, orthogonal lines or bars, or other configurations. The spatial pattern of the features will become the source of the wavefront. Without intending to limit the generality of the coded probe, some examples of possible bitmap features are provided in FIGS. 16A-H.

In an embodiment, features or elements can be formed from a wire, a string, such as a black string, horse hair, or fishing wire; a tube, such as a tube filled with a fluid, nanoparticles, dyes, chromophores, etc. In an embodiment, a feature may be an optical window, or an optical diffuser located on the probe that produces a known wavefront. In an embodiment, a feature may be an embossment or a cavity. A feature cavity can be used to collect parallel light, a collimator, and absorber behind a polarizing mask to create an optical filter.

In an embodiment, three dimensional features are used. For example, the face of the probe (or other system component) need not be flat. It can be convex, directing the normal of the wave to reduce or increase acoustic reflections due to mismatch. In an embodiment, it can be advantageous to have a concave or convex probe to disperse (or focus) the wavefront.

Cavity

In an embodiment, the probe may include a cavity. Such a cavity can be formed in various ways including, but not limited to, having a raised outline protruding from the probe face or having a depression inset in the probe face. The cavity may also be positioned elsewhere on the probe or on another system component. In an embodiment, the cavity traps a coupling medium used at an interface between the probe (or other system component) and the volume. In an embodiment, the cavity is configured to act as a coded feature as discussed above. In an embodiment, the cavity absorbs stray light. In an embodiment, the cavity acoustically isolates a region of the volume. In an embodiment, the cavity produces or directs at least one wavefront into the volume. In an embodiment, wavefronts or other effects produced by the cavity are predicted, simulated, or approximated to aide in component separation or other processing of acoustic signals as discussed above.

2. Mechanical Properties

As described above, modifying mechanical properties of the probe can cause coded wavefronts to be produced. In an embodiment, the probe comprises layers of different acoustically matched materials that will cause a reflection from the probe to have multiple reflections that occur from each layer. For example, in an embodiment, rather than having a single wavefront occur (of a single plane wave), acoustically mismatched layered media can be used to create two or more wavefronts, one for each reflecting layer, corresponding to a coded transfer function. This is to say that the probe can be adapted to produce multiple plane waves, rather than one plane wave, the relationship causing the SAR to be modulated by the transfer function of the coded probe.

3. Optical Properties

In an embodiment, features or elements sensitive to different wavelengths of electromagnetic radiation are used in a coded manner or pattern. For example, the probe surface can be fitted with a first feature and second feature, wherein the first feature produces a stronger wavefront in response to a first wavelength than at a second wavelength; and the second feature produces a stronger wavefront in response to a second wavelength than it does from the first wavelength. In an embodiment, spatially placing such features on the probe may further permit discriminating PAB in a multi-wavelength situation. For example, if a portion of the shape of produced wavefront is the same for both wavelengths, the SAR component due to that portion should also be similar; however, when a portion of the shape of the produced wavefront differs between wavelengths, the differences may assist with identifying the SAR representation.

Elements of acoustic mismatch (e.g. a bubble, a hole, a different density or different speed of sound), may also produce different intensity wavefronts since the intensity of mismatch reflections is based on the heating and initial pressure profiles of the background tissue, which may depend on its optical scattering and optical absorption profile.

Optically Absorbing Features

In the case of optically absorbing features, the features need not block an optical exit port of the probe. In an embodiment, the volume comprises a turbid scattering medium that will bend the light to distribute it back on to the probe. For example, FIG. 17 shows an illustrative trajectory of photons starting from an optical exit position and travelling through the volume to reach a point on the face of the probe before being absorbed (Monte Carlo simulation of light exiting from point a to b). The intensity of the energy reaching point b is proportional to the number of photons that arrive there. Photons that do not travel from a to b are not shown.

For light absorbing features, the spatial pattern of the features will become a pressure source (source of initial pressure) that will propagate through the volume according to opto-acoustic wave equations.

Surface Travelling Codes from Acoustic Mismatch

Optically absorbing codes may not be the only components which contribute to PAB or PASW wavefronts. PASW codes were described above as resulting from energy absorption; however they could also be created in response to energy distribution caused by on an acoustic mismatch in the volume. In an embodiment, the illumination profile of the background medium is constant. Alternatively, if the optically absorbing features are perfectly acoustically matched with the adjacent probe that they are connected to, wavefronts caused by acoustic mismatch will not be substantially different than those that originate at the locations near the codes (i.e. the code will be an optically absorbed produced code), otherwise there would have been a further unknown.

Features on the probe surface oriented perpendicular to a one-dimensional, linear array of receivers will appear as diagonal in the sinogram. Features oriented parallel to a one-dimensional linear array of detector elements will appear as horizontal in the sinogram. If the probe face is not flat, the shape curve that an ideal point source on the probe face will produce on the sinogram may be governed by non-Euclidean geometry as depending on the probe face curvature.

Determining Wavefront

In an embodiment, the intensities of PAB wavefront codes may be determined by first determining the intensities of measured PASW. In an embodiment, PAB signals are used to determine optical properties as described in the above paragraph for PASW; however the PAB will have backscattered acoustically through the tissue first, whereas the PASW will have travelled directly along the surface of the probe. Methods of using types of codes can help determine the wavefront properties.

Determining Nature of Probe-Volume Interface

In an embodiment, the probe-volume interface may include a coupling medium and/or air gap, and may be a difficult phenomenon to model (and thus develop an adaptive filter to compensate for). In an embodiment, PASW codes are used to determine information about the nature of the probe-volume interface. In an embodiment, the volume is skin tissue and PASW codes are used to determine information about the properties of the skin. When an unexpected amount of electromagnetic energy reaches a code, this discontinuity could signify that the probe is not optimally coupled with the volume. Thus, in embodiment, when such a discontinuity is detected, a signal is passed to the user to add more coupling medium and/or otherwise adjust the interface. For example, if the probe was lifted off of the skin, it may affect delivery of electromagnetic energy to the code, and such a discontinuity could be detected in this manner. If the probe has higher speed of sound than the volume or coupling medium, then the wavefront propagating along the probe from the code will reach the receivers at different times from the wavefront travelling along the surface of the volume or through the medium. Measuring the differences in arrival times of the codes along the surface can provide valuable information about the coupling. In an embodiment, the differences in arrival times are used to separate or otherwise process the acoustic signals as discussed above. In an embodiment, the PASW codes are calibrated such that a received waveform is measured for a known electromagnetic input, such as a laser pulse, when the probe is decoupled from the volume, and the measured waveform is stored as a calibration waveform. In an embodiment, when the probe is coupled to the volume, and data is recorded, the calibration waveform can be correlated with the recorded data, to find peaks in the correlation indicating a delayed pattern. In an embodiment, with the technique of using adaptive filtering, a best fit filter such FIR filter can be determined that when the calibration waveform is convolved with the filter, it reproduces the recorded data. By analyzing the filter, information about the coupling medium, such as multi-path effects, can be determined. In an embodiment, since speed-of-sound error results in temporal scaling in the recorded data, temporal scaling can be taken into account in the correlation model.

Modifying Light from the Probe

In an embodiment, the electromagnetic energy is light energy delivered to the volume via a probe or other system component. In an embodiment, the probe (or other system component) includes a light exit port positioned such that light exiting the port reaches the volume. In an embodiment, the illumination or photons of the light may be adjusted and the differences of the acoustic signals received before and after the adjustment may be used to determine optical properties. In an embodiment, features of the probe may be used to permit the received acoustic signals to differ in response to the adjustment of the photons. In an embodiment, the features may have different optical properties that respond differently to photons in a first state and photons in a second state. In an embodiment, such differences may be detected in the PAB or PASW signals. In an embodiment, the DAR signal may also change in response to the adjustment.

Such features may include, but are not limited to, optical fibers, light bars or sections of light bars, diffusers, polarizers, electromagnetic propagation of the light, optical filters, light sources, or wavelength sources, mirrors or the position and orientation of optical fibers, or other known means for affecting fluence distribution or how the light energy reaches the volume or another feature or element positioned on the probe (or other system component). In an embodiment, models are developed based on optical properties of the probe or volume. In an embodiment, such models are applied to simulate the effect of coding, separate signal components, or otherwise process acoustic signals. In an embodiment, such models are applied to solve the fluence distribution of the light in the volume. The tissue and coupling medium can affect the photons reaching features that cause acoustic wavefronts, surface wavefronts, or other effects.

Features that Block Light Exiting the Probe

In an embodiment, features, such as the features described above, are positioned at the light exit port or elsewhere in the light path. Such features can block or otherwise effect the light as it passes through the light exit port or other portion of the light path. Optically absorbing features directly in the path of the light exiting the exit port can have a different effect than similar optically absorbing features not in the light's direct path. In an embodiment, features in the light path absorb light or redirect or alter light without substantially absorbing it. In an embodiment, such features produce acoustic wavefronts (PAB or PASW). In the case of PASW, coded features can arrive at the acoustic receivers at the probe speed of sound, but may arrive at a different time through the coupling medium, or through the volume surface, which may have a variable speed of sound based on mechanical properties of the volume (e.g. a patient's skin), or operator applied pressure may alter the path length. Features directly in the light path can assist in removing interfering artifacts from light bars as light arrives at the volume. In another embodiment, a surface wave can be produced at a site located on the exit port that reduces the light delivered to a particular region of the volume. Other features blocking or otherwise affecting the light prior to the time it enters the volume will be apparent to one of skill in the art, and may be used in connection with the novel coded probe and component separation methods without departing from the scope of the inventions disclosed herein.

Directional PAB and PASW Features

In an embodiment, features that generate wavefronts that propagate in specific directions or headings may be used. For example, a first set of PAB features or codes of the probe may be configured to generate a first wavefront that travels along a first heading with a first predominant frequency content. Additionally, a second set of PAB features or codes may be configured to generate a second wavefront that travels along a second heading with a second predominant frequency content. In an embodiment, this may be extended to more than two directed wavefronts.

In an embodiment, a flat or planar element positioned with its surface normal to a heading may be used to emit a wave that substantially propagates along that heading. In an embodiment, the element may be apodized to reduce sidebands, or otherwise adapted to provide a narrow acoustic beam or focus the beam. In an embodiment a 3D structure may be used to generate directed wavefronts. In an embodiment, the 3D structure may include layers of material with different acoustic properties. In an embodiment, the 3D structure may contain layers with different optical properties. In an embodiment, the 3D structure may consist of layers of optically transparent material where an optically absorbent coating is placed between each layer. The thicknesses of the layers and coatings can be adjusted to produce a PAB code with tuned frequency content. In an embodiment, the structure can be tilted to direct a wavefront along a heading. In an embodiment, the feature does not block the optical exit port, but relies on light reflected from the volume. In an embodiment, the feature may block the optical exit port.

In an embodiment, PASW features emit ASW wavefronts and substantially do not emit wavefronts into the tissue. In an embodiment, this is done by using directional PASW features. In an embodiment, the orientation of the directional PASW features direct waves towards the acoustic receivers.

Shaping of an Ultrasound Transmit Beam Using a Pattern

In an embodiment, a light exit port comprising, e.g., an optical window, may be coated, at least in part, with 1) an optically reflective material (white), 2) an optically absorbent material (black), and portions of the light exit port may be transparent/left blank to permit light to pass through. In an embodiment, these coatings of the optical window may be applied to either side of the material the optical window is made from, e.g., glass. Coatings may be applied in layers, and may be deposited using a mask. In an embodiment, the coatings are applied to produce a particular pattern, and thereby to cause a shaped acoustic wavefront to be produced when the light is absorbed by the optically absorbent material. In an embodiment, the coatings may be opaque. In an embodiment, the optical window may be completely coated with opaque coating(s), thereby substantially preventing any light from exiting the port, thus rendering it an acoustical exit port (i.e., an acoustic transmitter). In an embodiment, the coating(s) are not opaque, and the port is completely or partially coated. In an embodiment, the coating(s) are opaque, but the port is only partially coated. In an embodiment, the pattern of the coating(s) is dithered to control the intensity of light absorbed from a region. Thus, in an embodiment, materials in the light path comprise an optically interacting mode that is configured to interact with the light energy in the light path. The optically interacting modes may be: i) an optically reflective mode to substantially reflect light energy and produce substantially no acoustic energy response; ii) an optically absorbing mode to substantially absorb light energy and produce an acoustic energy response, wherein a portion of the produced acoustic energy exits an energy port of the light path; and, iii) an optically transparent mode to substantially transmit light energy and produce substantially no acoustic energy response, wherein the transmitted light energy exits the energy exit port. In an embodiment, a pattern comprises different optically interacting modes. In an embodiment, an optically interacting mode may be dithered. The dithering can cause certain regions of the pattern to thus absorb more light, and other regions to absorb less light, thereby permitting a smooth transition of intensity, rather than having sharp contrast of the levels of optical absorption, a particular material having a fixed optical absorption. In an embodiment, the pattern is based on a 2D wavelet. In an embodiment, the 2D wavelet is composed of separable 1D representations. In an embodiment, the 2D wavelet is radial. In an embodiment, the pattern includes concentric circles or ellipses. In an embodiment, the pattern includes lines with line-width modulation to determine the intensity of light. In an embodiment, the lines are a grating. In an embodiment, a pattern is used to produce a laser-generated ultrasound wavefront with controlled directivity, beam profile, etc. The properties of the wavefront beam can be controlled by the shape of the initial pressure distribution. In this manner, an apodized ultrasound wavefront can be produced, for example if the intensity of the wavelet decays as the distance from its center increases. In an embodiment the ultrasound beam is shaped to direct ultrasound towards the imaging plane. In an embodiment, the ultrasound beam is shaped to direct ultrasound away from the imaging plane. In an embodiment, the ultrasound beam is shaped to reduce sidelobes, which may have been the result of a sharp cut-off of the initial pressure profile, and dithering may be used to gradualize this sharp cut-off.

FIGS. 18A and B show an example dithered wavelet pattern that can be used to produce a customized initial pressure profile for an ultrasound beam. FIG. 18A shows an acoustically absorbing mask, while FIG. 18B shows an acoustically reflective mask.

III. Optical Tomography

Measuring Fluence and Optical Properties

When the absorption of light is blocked (by the tissue or other volume) after exiting the exit port on the way to the probe features, the absorption of light by the features producing ultrasound will be reduced since less light reaches them. Since, in an embodiment, the features are codes, the amount of light reaching the features to produce a wavefront source may be used to infer the strength of light delivered, and the first order surface wave signal that gets detected can be used to infer information about the optical properties of the volume. Stated another way, as the light travels from the optical exit port through the volume, to optically absorbing features on the probe, a resultant surface wave may travel on the surface of the interface to the acoustic receivers. This produced acoustic surface wave (PASW) may be measured and used to determine information about the optical properties of the volume. In an embodiment, the skin and background tissue may be modeled as a single layer or dual layer medium with unknown optical properties. In an embodiment, using PASW codes, along with a known illumination pattern from exit ports, can be used to solve the effective unknown optical properties for a single layer or dual layer model, where each layer can be modeled with homogeneous optical properties. In an embodiment, the known illumination is determined by measurement (e.g. using an optical sensor such as a photo-diode). In an embodiment, each layer may have a layer depth or thickness parameter. In an embodiment, a tissue layer in the model may have a single value for optical scattering and single value for optical absorption for a given wavelength. In an embodiment, each layer may have an isotropy parameter. In an alternate embodiment, a tissue layer in the model may have a single value for effective optical absorption for a given wavelength. In an embodiment, the model may incorporate diffuse or collimated light propagating through the tissue layers in accordance with the optical properties. In an embodiment, the surface of the volume may reflect or absorb the light. In an embodiment, the light intensity reaching a code will depend on the optical parameters of the medium. In an embodiment, the light intensity reaching a code will be converted into a PASW component of an acoustic signal. In an embodiment, the PASW code as an acoustic wave will undergo attenuation, dispersion, geometric spreading or obey a transfer function as it travels to an acoustic receiver. In an embodiment the acoustic receivers will measure PASW components. In an embodiment, acoustic receiver has an electro-mechanical and/or directional transfer function. In an embodiment, the PASW code is calibrated using a known optical wavelength and intensity on the PASW element. In an embodiment, the PASW code yields a known output waveform in response to a known input illumination waveform such as an input pulse. In an embodiment, acoustic effects and transfer functions of PASW waves are compensated. In an embodiment, multiple PASW code elements located at multiple distances from a light source coupled to the volume may be used to determine the optical parameters of a tissue model, such as the layered model described above. Since the photons travel from the light source through the volume to the PASW element, the positioning of multiple elements will allow curve fitting to a tissue model depending on the unknown optical properties of the model to determine the unknown optical properties of the model. In an embodiment, PASW codes are wavelength dependent. In an embodiment, a first element or portion of an element produces a stronger acoustic waveform in response to a first input wavelength of light or other electromagnetic energy than a second element or portion of an element in response to a second wavelength. In an embodiment, wavelength sensitive PASW codes or elements may be used to determine the oxygen saturation, water content, hemoglobin content, melanin content, or other such molecular component.

In an embodiment, when optical parameters of the volume (e.g., optical parameter constants of a layer tissue model) are determined based on measuring the optical fluence exiting the volume (e.g., using PASW codes, or an optical sensor), these optical parameters do not only describe a best fit for the model to match the observed measurements. In addition, in an embodiment, once the parameters are known the amount of light penetrating deep into the tissue can be solved. This is particularly helpful in opto-acoustics because an unknown optical fluence profile may otherwise reduce accuracy. In an embodiment, if the energy fluence in the imaging plane is solved, it can be used towards fluence compensation in opto-acoustic imaging. An example of fluence compensation is described in U.S. patent application Ser. No. 13/793,808.

In an embodiment, the optical energy exiting the surface of the volume can be measured for an energy event used to produce a sinogram. In an embodiment, this is performed for multiple wavelengths. In an embodiment, the optical energy is measured at multiple locations on the surface. In an embodiment, the best fit solution of a fluence model representing the 3D volume that fits the combined set of measurements can be solved. In an embodiment, the result of the best fit fluence may be a set of constant parameters representing the model, a curve, or set of curves, or the solution of optical parameters and/or fluence for a 2D or 3D volume. In an embodiment, a fluence distribution curve(s) for a 2D imaging plane may be extracted from this result. In an embodiment, the fluence distribution curve(s) may be further (or already be) best fit onto a fluence model representing the imaging plane. In an embodiment, the fluence model representing the imaging plane may be a 1D function. In an embodiment, the solution of a best fit fluence model may yield fluence compensation curves. In an embodiment, the fluence compensation curves may be applied to compensate an opto-acoustic image. In an embodiment, the fluence distribution is assumed to change slowly, or be constant across multiple energy events, or for a given imaging subject; hence, the sensor readings from multiple events (e.g., a previous number of events) can be averaged or combined and used to determine the result of the best fit fluence. In an embodiment, an optical parameter measured by the system comprises an optical absorption coefficient. In an embodiment, an optical parameter measured by the system comprises an optical scattering coefficient. In an embodiment, an optical parameter measured by the system comprises an optical isotropy parameter.

The surfaces of the probe, volume, and/or coupling medium may have substantially different or the same speeds of sound. In an embodiment, codes can be constructed (such as mutually orthogonal bit-sequences) represented as feature dots on the surface of the probe, such that wavefronts from these features reach acoustic receivers (via the surface wave) at different times. In an embodiment, the positions of features are located on a grid or lattice. Interfering codes can then be decoded by separating apart the mutually orthogonal code sequences and determining their relative intensities, of course taking into account the anticipated acoustic wave attenuation along the way. CDMA or other wireless transmission techniques for separating different codes are applicable. In an embodiment, iterative reconstruction techniques are applicable to separate one coded feature from another. Accordingly, in an embodiment, each feature represents a voxel, and the point spread function (or impulse response) of the voxel due to the illumination event can be measured. In an embodiment, this may be done to produce an image representing PASW features on the surface, and their respective received intensities. In an embodiment, once a surface image is produced, the image intensities from each feature as positioned in the image can be extracted. In an embodiment, the extracted feature intensities can be used to represent the electromagnetic energy exiting the volume. In an embodiment, each PASW feature has a foreknown independent forward response (e.g. transfer matrix) that varies in amplitude in proportion to the amount of energy the feature absorbs. In an embodiment, the forward response is used to determine the point spread in an iterative reconstruction technique. In an embodiment, the forward response can be calibrated by placing the probe on the surface of a calibration volume (e.g. non-turbid medium) and illuminating each feature individually using a beam with a known electromagnetic (e.g. optical) fluence for a given wavelength, then measuring the response waveform (e.g. sinogram) from the acoustic receivers. In an embodiment, the distances of the features will not interfere with deep tissue imaging. In an embodiment, interfering codes can be removed from images and data using the technique of interframe persistent artifact removal as discussed above. In an embodiment, the technique of interframe persistent artifact removal may be applied after determining the intensities of the code, and then adaptively computing a static artifact removal frame. In an embodiment PASW wavefronts may be produced by features as described for PAB wavefronts above. In an embodiment, PAB wavefronts directed into the volume also have corresponding PASW wavefronts along the surface. In an embodiment, PASW may include elastic waves. In an embodiment, PASW includes shear waves. In an embodiment, acoustic waves include elastic waves. In an embodiment, PASW wavefronts are an alternative to optical detectors located on the surface of the probe or another system component.

PASW Sensor for Measuring Optical Properties of a Volume

Ordinary optical sensors have been used to measure the intensity of photons exiting a volume that were sent into the volume by a photon source positioned a distance away from the sensor. In certain applications, it may not be practical to place an optical or electromagnetic sensor on the surface of a probe or other device. Accordingly, a sensor is described in this section that may be applicable towards combining Diffuse Optical Tomography or Near-Infrared Spectroscopy with opto-acoustics on a single probe, or it may have use in other applications. In an embodiment, an optical or electromagnetic sensor for determining the propensity of photons to travel through a volume is provided, comprising: 1) an acoustic receiver; 2) a source of photons (or a photon exit port) configured to be coupled and delivered into a volume; 3) an optical or electromagnetically absorbing element positioned a distance away from the photon source and configured to absorb photons from the photon source that have traveled through and exited the volume such that a pressure source is produced by the photon absorption to create a wave; 4) a wave propagation medium, such as the surface of the sensor or probe, that allows a wave, such as an acoustic surface wave, to propagate from the absorbing element to the acoustic receiver; and 5) an electrical path configured to connect the acoustic receiver to an acquisition system to sample the receiver. In an embodiment, the element has a first absorption coefficient for a first wavelength, and second absorption coefficient for a second wavelength. In an embodiment, two different elements are used with different absorption coefficients. This allows the wavelength dependence of volume to be examined, and to determine spectroscopic properties of the volume. In an embodiment, the wave propagation medium is a surface that has been coated with a coating, such as a reflective coating (e.g., gold), and the coating has been applied on top of a highly acoustically absorbing medium, such as an acoustic isolator consisting of a material containing micro-bubbles. The coating can prevent or reduce optical absorption of the surface. The highly acoustically absorbing medium can prevent shear waves or other waves from travelling to the acoustic receiver from another path besides the surface or inhibit waves from the photon source that would otherwise reach the receiver. In an embodiment, multiple elements and/or multiple receivers are used in the sensor. In an embodiment, PASW component separation as described herein (without limitation) is used with the sensor or sensors. In an embodiment, the sensor is integrated on a handheld opto-acoustic probe as described herein. In an embodiment, elements are placed on top of the coating. In an embodiment, elements are coded or patterned into PASW codes and incorporated into the sensor as described herein (without limitation). In an embodiment, the absorbing element produces a directed acoustic wave, such that the acoustic wave travels preferentially towards the acoustic receiver and to a lesser extent into the volume. This preference can help to reduce a SAR component.

In an embodiment, the sensor may be used on a combined opto-acoustic probe for determining the optical properties of the tissue. In an embodiment, the probe may combine optical tomography with opto-acoustics. In an embodiment, an image or 3D volume representing the optical parameters or fluence may be output. In an embodiment, it may be overlayed on top of opto-acoustic or ultrasound imagery. In an embodiment, the determined optical fluence and properties of the medium may be used to compensate opto-acoustic images.

Those skilled in the art will recognize that the methods and systems of the present disclosure may be implemented in many manners and as such are not to be limited by the foregoing exemplary embodiments and examples. In other words, functional elements being performed by single or multiple components (or modules), in various combinations of hardware and software or firmware, and individual functions, may be distributed among software applications at either the client level or server level or both. In this regard, any number of the features of the different embodiments described herein may be combined into single or multiple embodiments, and alternate embodiments having fewer than, or more than, all of the features described herein are possible. Functionality may also be, in whole or in part, distributed among multiple components, in manners now known or to become known. Thus, myriad software/hardware/firmware combinations are possible in achieving the functions, modules, features, interfaces and preferences described herein. Moreover, the scope of the present disclosure covers conventionally known manners for carrying out the described features and functions and interfaces, as well as those variations and modifications that may be made to the hardware or software or firmware components described herein as would be understood by those skilled in the art now and hereafter.

Various modifications and alterations to the invention will become apparent to those skilled in the art without departing from the scope and spirit of this invention. It should be understood that the invention is not intended to be unduly limited by the specific embodiments and examples set forth herein, and that such embodiments and examples are presented merely to illustrate the invention, with the scope of the invention intended to be limited only by the claims attached hereto. Thus, while the invention has been particularly shown and described with reference to a preferred embodiment thereof, it will be understood by those skilled in the art that various changes in form and details may be made therein without departing from the spirit and scope of the invention.

What is claimed is:

1. A medical imaging system, comprising:
   at least one light source for delivering light energy to a volume of tissue;
   a transducer array for receiving an acoustic signal in response to the delivery of light energy, the acoustic signal comprising at least a direct acoustic return component and a secondary acoustic return component, the secondary acoustic return component comprising an acoustic response that is substantially reflected or scattered before arriving at the transducer array;
   a processing subsystem for processing the acoustic signal to separate the direct acoustic return component from the secondary acoustic return component of thereof by applying at least one of a simulation, reconstruction, point spread function, error calculation, or correction function to the acoustic signal; and,
   an output device for presenting information about at least one of the direct acoustic return component and the secondary acoustic return component.

2. The medical imaging system according to claim 1, wherein the output device comprises a display for displaying an image that utilizes the information about the direct acoustic return component, the secondary acoustic return component, or both.

3. The medical imaging system according to claim 1, wherein the output device comprises a storage device for storing the information about the direct acoustic return component, the secondary acoustic return component, or both.

4. The medical imaging system according to claim 1, wherein the processing subsystem applies a simulation function that comprises:
   a sub-module for reconstructing secondary acoustic return spatial representations from the secondary acoustic return components;
   a sub-module for reconstructing direct acoustic return spatial representations from the direct acoustic return components;
   a sub-module for simulating secondary acoustic return signals from the secondary acoustic return spatial representations; and
   a sub-module for simulating direct acoustic return signals from the direct acoustic return spatial representations.

5. The medical imaging system according to claim 4, wherein the processing subsystem is configured to apply the point spread function to a current estimate of a direct acoustic return representation and a current estimate of a secondary acoustic return representation.

6. The medical imaging system according to claim 5, wherein the point spread function is applied according to steps comprising:
   simulating the current direct acoustic return estimate to produce a direct acoustic return sinogram using the direct acoustic return simulation sub-module;
   simulating the current secondary acoustic return estimate to produce a secondary acoustic return sinogram using the direct acoustic return simulation sub-module;
   adding the direct acoustic return sinogram to the secondary acoustic return sinogram to produce an overall sinogram;
   reconstructing direct acoustic return from the overall sinogram to produce a direct acoustic return PSF representation using the direct acoustic return reconstruction sub-module; and,
   reconstructing secondary acoustic return from the overall sinogram to produce a secondary acoustic return PSF representation using the secondary acoustic return reconstruction sub-module.

7. The medical imaging system according to claim 4, wherein the processing subsystem is configured to execute a process for component separation, comprising the steps of:
   a) producing a reference representation for direct acoustic return and a reference representation for secondary acoustic return by reconstructing the recorded acoustic return signals using the direct acoustic return sub-module and the secondary acoustic return sub-module; and, b) computing at least one iteration comprising the steps of:
  i) applying a point spread function to current estimates of direct acoustic return and secondary acoustic return;
  ii) computing residuals between the reference representations and PSF representations;
  iii) multiplying the residuals by a weight to give weighted residuals;
  iv) adding the weighted residuals to the current estimates of direct acoustic return and secondary acoustic return; and,
  v) applying thresholding to produce the next estimates of direct acoustic return and secondary acoustic return.

8. The medical imaging system according to claim 4, further comprising:
  a sub-module for computing a residual between a simulated estimate of electromagnetically absorbent targets within the volume and a reference based on recorded direct acoustic return signals;
  a sub-module for computing a residual between a simulated estimate of acoustically reflective targets within the volume and a reference based on recorded secondary acoustic return signals;
  a sub-module for modifying the estimates of the targets based on computed residuals; and,
  a sub-module for outputting final estimates of spatial or signal representations of the targets.

9. The medical imaging system according to claim 4, wherein the direct acoustic return simulation sub-module and direct acoustic return reconstruction sub-module use delays based on voxel to transducer element distances, and wherein the secondary acoustic return simulation sub-module and secondary acoustic return reconstruction sub-module use delays based on wavefront source to voxel to transducer element distances.

10. The medical imaging system according to claim 1, further comprising a probe with a distal surface, wherein the acoustic impedance of at least a portion of the distal surface is acoustically mismatched to the volume of tissue and the secondary acoustic return component comprises reflections from targets in the volume by a wavefront originating proximate to the distal surface and in response to the delivery of light energy, the wavefront produced as a result of the acoustic mismatch following the light delivery.

11. The system of claim 1, wherein the processing subsystem is configured to separate the direct and secondary acoustic return components that are received during a common sample cycle.

12. The system of claim 1, wherein the processing subsystem is configured to separate the direct and secondary acoustic return components based on at least one of a time delay, propagation time, speed of sound profile, or simulation look-up table.

13. The system of claim 1, wherein the secondary acoustic return component travels from a wavefront source to a target in the volume of tissue and then from the target to the transducer array.

14. The system of claim 13, wherein the wavefront source is located proximate to a surface of the volume of tissue and generates a wavefront in response to the light energy.

15. A system, comprising:
  an energy source configured to deliver electromagnetic energy to a volume comprising one or more acoustic targets;
  a probe with an outer surface to form a coupling interface between itself and a surface of the volume;
  one or more elements on the outer surface of the probe to produce a predictable wavefront pattern originating substantially at the coupling interface as a result of the delivered energy; and,
  an acoustic receiver to receive an acoustic return comprising direct acoustic return signals and secondary acoustic return signals, the secondary acoustic return signals comprising at least a portion of the predictable wavefront pattern that is scattered by the one or more acoustic targets; and,
  a processing subsystem configured to process the acoustic signal to separate the direct acoustic return signals from the secondary acoustic return signals by applying a received wavefront resulting from the predictable wavefront pattern.

16. The system of claim 15, wherein the coupling interface is coupled using a coupling medium.

17. The opto-acoustic probe of claim 16, wherein the secondary acoustic return component is used to produce an image separate from a produced direct acoustic return image.

18. The system of claim 15, wherein the processing subsystem is configured to use the received wavefront by forming a direct acoustic return representation with a distinguishable secondary acoustic return component.

19. The opto-acoustic probe of claim 18, configured such that the distinguishable secondary acoustic return component can be recognized by computer processing without substantially distorting a produced direct acoustic return image to be perceived by a human.

20. The system of claim 15, wherein the one or more featured elements comprises an optically absorbing line source.

21. The system of claim 20, wherein the optically absorbing line source meets with other optically absorbing line sources to form a rectangle.

22. The system of claim 15, wherein the predictable wavefront pattern resulting from featured elements on the outer surface of the probe comprises a wavefront produced by an air-tissue interface surrounding the outer surface.

23. The system of claim 15, wherein the received secondary acoustic return signals are used to produce an image, which can be separately displayed or co-registered with a direct acoustic return image.

24. A method, comprising:
  placing a surface of a probe proximate to a surface of a volume;
  delivering light from a light source to the volume, wherein a portion of the light from the light source is absorbed by patterns on the surface of the probe;
  receiving acoustic signals from the volume, wherein the received acoustic signals comprise probe acoustic backscatter (PAB) components of acoustic signal resulting from scattering of wavefronts produced by the patterns on the surface of the probe in response to absorbing the portion of the light;
  processing the received acoustic signals to identify a first PAB component that resulted due to scattering by a target at a first position in the volume, wherein a first acoustic front due to the patterns on the surface of the probe targeting the first position in the volume is distinguishably different from a second acoustic front due to the patterns on the surface of the probe targeting a second position in the volume, wherein a second PAB component of a target at the second position interferes with the first PAB component and wherein prediction of acoustic fronts due to the patterns on the surface of the probe reaching positions in the volume is used to identify the first PAB component;

outputting an intensity of the first PAB component at the first position in the volume; and separating a direct acoustic return component from the acoustic signals based on the first PAB component.

25. The method of claim 24, wherein the received acoustic signals are received by at least one receiver located on the surface of the probe and the surface of the probe further comprises at least one exit port to deliver the light from the light source to the volume, wherein a portion of the light from the light source exiting the exit port is absorbed by optically absorbing targets in the volume.

26. The method of 24, further comprising forming an image of a portion of the volume, wherein the image comprises voxels and a voxel of the image is computed by computing a voxel intensity that is outputted by the step of outputting wherein the first position in the volume corresponds to the position of the voxel.

27. The method of claim 26, wherein the second position in the volume in computing the computed voxel intensity corresponds to a position in the volume that is outside of the imaged portion of the volume and thus does not correspond to a voxel in the image.

28. The method of claim 26, wherein the step of forming an image of a portion of the volume comprises performing an iterative process comprising:
  simulating received signals from a target at one position and from an interfering target at another position to produce simulated signals; and,
  reconstructing a spatial representation of the volume from the simulated signals.

29. The method of claim 28, wherein the received acoustic signals are received by an array of receivers incident with an imaging plane partitioning the volume and the method is used to suppress out-of-plane objects in the image and the portion of the volume in the image is within the imaging plane.

30. The method of claim 26, further comprising:
  receiving direct acoustic return from the volume;
  forming a direct acoustic return spatial representation of the volume from the received direct acoustic return;
  using the formed image to identify and suppress out-of-plane objects m the direct acoustic return spatial representation; and,
  displaying the direct acoustic return spatial representation on a display.

31. The method of claim 26, further comprising displaying the image on a display.

32. A method, comprising:
  placing an opto-acoustic probe comprising a distal surface into contact with a surface of a volume to form a coupling interface, wherein the distal surface comprises a detector array;
  delivering energy to the volume;
  receiving acoustic signals comprising:
    a direct component due to acoustic return signals produced within the volume; and,
    a surface component due to an acoustic wavefront propagating substantially proximate to the distal surface where the wavefront reaches elements of the detector array in a sequence, wherein the surface component varies according to at least one parameter that is dependent on properties of the coupling interface or materials proximate thereto;
  processing the acoustic signals to determine the at least one parameter;
  separating the direct component based on the at least one parameter;
  forming an image using the acoustic signals that is spatially representative of the volume, wherein formation of the image is dependent on the direct component and the at least one parameter; and,
  outputting the image to a display.

33. The method of claim 32, wherein the elements of the detector array are aligned in a row and spaced equidistantly so that the acoustic signals arrange to form a sinogram with the surface component presented substantially as a diagonal line, the step of processing further comprising a step selected from the group consisting of:
  using slope of the diagonal line to infer a speed of sound;
  using an intercept of the at least one diagonal line to infer the position of origin of a wavefront; and,
  using change of intensity of the at least one diagonal line to infer an attenuation coefficient.

34. The method of claim 32, wherein the parameter is selected from the group consisting of:
  a shear wave velocity or sound speed;
  a longitudinal wave velocity or sound speed;
  a coupling medium thickness;
  a status of whether the probe is in contact with the volume;
  a position beyond which the distal surface is not in contact with the volume;
  a thickness of an epidermal layer;
  mechanical property of the coupling interface;
  a position where a surface wavefront originates;
  a parameter for mitigating an artifact;
  an attenuation coefficient; or,
  an acoustic impedance.

35. The method of claim 32, wherein the wavefront is produced at a discontinuity of a feature of the probe.

36. The method of claim 35, wherein the discontinuity is of a property selected from the group consisting of: optical absorption and acoustic impedance.

37. The method of claim 35, wherein formation of the image comprises the step of mitigating the surface component so that an artifact from the surface component is not displayed in the image.

38. The method of claim 32, wherein a portion of the surface of the volume that is not in contact with the opto-acoustic probe is exposed to air, and the discontinuity is at a boundary where probe, air and tissue meet.

39. A computer implemented method comprising:
  receiving a plurality of acoustic return signals at a transducer array, each signal received from a position proximate to an outer surface of a volume in response to delivery of electromagnetic energy to the volume;
  utilizing one or more processors for:
    applying a pattern detection classifier to each received signal to produce a plurality of classifier output signals, each classifier output signal is representative of an indicator strength as a function of time in each received signal;
    reconstructing a spatial representation of the volume from the plurality of classifier output signals;
  receiving a direct acoustic return component, at the transducer array, from the volume in response to delivery of electromagnetic energy to the volume; and, outputting an image based on the direct acoustic return component and the reconstructed spatial representation.

40. The method of claim 39, wherein the indicator strength is tuned to acoustic signals resulting from a pattern on the surface of a probe acoustically coupled to the volume.

41. The method of claim 39, wherein the step of reconstructing a spatial representation comprises using an iterative minimization.

42. A computer implemented method for performing medical imaging, comprising:
  delivering light energy to a volume of tissue from a light source;
  receiving, at a transducer array, an acoustic signal in response to the delivery of light energy, the acoustic signal comprising at least a direct acoustic return component and a secondary acoustic return component, the secondary acoustic return component comprising an acoustic response that is substantially reflected or scattered before arriving at the transducer array;
  utilizing one or more processors to process the acoustic signal to separate the direct acoustic return component from the secondary acoustic return component of thereof by applying at least one of a simulation, reconstruction, point spread function, error calculation, or correction function to the acoustic signal; and,
  presenting information about at least one of the direct acoustic return component and the secondary acoustic return component.

43. The method according to claim 42, wherein the presenting comprises displaying an image that utilizes the information about the direct acoustic return component, the secondary acoustic return component, or both.

44. The method according to claim 42, wherein the presenting comprises storing the information about the direct acoustic return component, the secondary acoustic return component, or both.

45. The method according to claim 42, wherein the processing applies the simulation function that comprises:
  reconstructing secondary acoustic return spatial representations from the secondary acoustic return components;
  reconstructing direct acoustic return spatial representations from the direct acoustic return components;
  simulating secondary acoustic return signals from the secondary acoustic return spatial representations; and
  simulating direct acoustic return signals from the direct acoustic return spatial representations.

46. The method according to claim 42, wherein the processing comprises applying a point spread function based on estimates associated with the direct and secondary acoustic return components.

47. The method according to claim 46, wherein the point spread function is applied according to steps comprising:
  simulating a current direct acoustic return estimate to produce a direct acoustic return sinogram;
  simulating a current secondary acoustic return estimate to produce a secondary acoustic return sinogram;
  adding the direct acoustic return sinogram to the secondary acoustic return sinogram to produce an overall sinogram;
  reconstructing a direct acoustic return from the overall sinogram to produce a direct acoustic return PSF representation; and,
  reconstructing a secondary acoustic return from the overall sinogram to produce a secondary acoustic return PSF representation.

48. The method according to claim 46, wherein the process for component separation, comprising the steps of:
  a) producing a reference representation for direct acoustic return and a reference representation for secondary acoustic return by reconstructing the recorded acoustic return signals using the direct acoustic return sub-module and the secondary acoustic return sub-module; and,
  b) computing at least one iteration comprising the steps of:
    vi) applying a point spread function to current estimates of direct acoustic return and secondary acoustic return;
    vii) computing residuals between the reference representations and PSF representations;
    viii) multiplying the residuals by a weight to give weighted residuals;
    ix) adding the weighted residuals to the current estimates of direct acoustic return and secondary acoustic return; and,
    x) applying thresholding to produce the next estimates of direct acoustic return and secondary acoustic return.

49. The method according to claim 46, further comprising:
  computing a residual between a simulated estimate of electromagnetically absorbent targets within the volume and a reference based on recorded direct acoustic return signals;
  computing a residual between a simulated estimate of acoustically reflective targets within the volume and a reference based on recorded secondary acoustic return signals;
  modifying the estimates of the targets based on computed residuals; and,
  outputting final estimates of spatial or signal representations of the targets.

* * * * *